US007850960B2

(12) United States Patent
Moon et al.

(10) Patent No.: US 7,850,960 B2
(45) Date of Patent: Dec. 14, 2010

(54) METHODS FOR REGULATION OF STEM CELLS

(75) Inventors: Randall T. Moon, Kenmore, WA (US); Mickie Bhatia, London (CA); Jennifer Jean Trowbridge, Essex (CA)

(73) Assignees: University of Washington, Seattle, WA (US); Robarts Research Institue, London, Ontario (CA)

( * ) Notice: Subject to any disclaimer, the term of this patent is extended or adjusted under 35 U.S.C. 154(b) by 5 days.

(21) Appl. No.: 11/026,399

(22) Filed: Dec. 30, 2004

(65) Prior Publication Data

US 2006/0147435 A1 Jul. 6, 2006

(51) Int. Cl.
*A61K 48/00* (2006.01)
*C12N 5/08* (2006.01)
*C12N 15/87* (2006.01)

(52) U.S. Cl. ............. 424/93.21; 435/455; 435/372

(58) Field of Classification Search ............. None
See application file for complete search history.

(56) References Cited

U.S. PATENT DOCUMENTS

| | | | |
|---|---|---|---|
| 5,994,084 | A | 11/1999 | Anderton et al. |
| 6,057,117 | A | 5/2000 | Harrison et al. |
| 6,171,781 | B1 | 1/2001 | Crabtree et al. |
| 6,479,255 | B1 | 11/2002 | Rubin et al. |
| 6,608,063 | B2 | 8/2003 | Nuss et al. |
| 6,784,155 | B1 | 8/2004 | Wolpe et al. ............ 514/6 |
| 2001/0053351 | A1 | 12/2001 | Hoeflich et al. |
| 2002/0114772 | A1 | 8/2002 | Morgan et al. |
| 2004/0014209 | A1 | 1/2004 | Lassar et al. |
| 2004/0018531 | A1 | 1/2004 | Jamieson et al. |
| 2004/0038860 | A1 | 2/2004 | Allen et al. |
| 2004/0087016 | A1 | 5/2004 | Keating et al. |
| 2004/0092535 | A1 | 5/2004 | Barsanti et al. |
| 2004/0209878 | A1 | 10/2004 | Guzi et al. |
| 2004/0224887 | A1 | 11/2004 | Jessel et al. |
| 2006/0004043 | A1* | 1/2006 | Bhagwat et al. .......... 514/314 |
| 2008/0207594 | A1 | 8/2008 | Mussmann et al. |

FOREIGN PATENT DOCUMENTS

| WO | 2005/051942 A1 | 6/2005 |
|---|---|---|
| WO | 2007016485 | 2/2007 |

OTHER PUBLICATIONS

Sato et al. (Nature Medicine, Jan. 2004; 10(1): 55-63).*
Dravid et al. (Stem Cells. 2005; 23(10): 1489-1501).*
James et al. (Development. 2005. 132: 1273-1282).*
Bendall et al. (Nature. 2007. 448(7157): 1015-1021).*
Ring et al. (Diabetes. Mar. 2003; 52:588-595).*
Moon et al. (Nature Reviews Genetics. Sep. 2004; 5: 689-699).*
Sauvageau et al., "In vitro and in vivo expansion of hematopoietic stem cells," *Oncogene*, 2004, 23, 7223-7232.
Ding et al., "A role for chemistry in stem cell biology," *Nature Biotechnology*, 2004, 22(7), 833-840.

Alberdi, "Binding of Pigment Epithelium-derived Factor (PEDF) to Retinoblastoma Cells and Cerebellar Granule Neurons," *J. Biol. Chem.*, 1999, 274, 31605-31612.
Aymerich et al., "Evidence for Pigment Epithelium-Derived Factor Receptors in the Neural Retina," *Invest. Ophthalmol. Vis. Sci.*, 2001, 42(13), 3287-3293.
Barker et al., "Transplantation of 2 Partially HLA-matched Umbilical Cord Blood Units to Enhance Engraftment in Adults with Hematologic Malignancy," *Blood*, 2005, 105(3), 1343-1347.
Baron et al., "Hematopoietic Cell Transplantation: Five Decades of Progress," *Arch. Med. Res.*, 2003, 34, 528-544.
Behrens et al., "Functional Interaction of an Axin Homolog, Conductin, with β- Catenin, APC, and GSK3β," *Science*, 1998, 280, 596-599.
Berman et al., "Medulloblastoma Growth Inhibition by Hedgehog Pathway Blockade," *Science*, 2002, 297, 1559-1561.
Bhardwaj et al., "Sonic Hedgehog Induces the Proliferation of Primitive Human Hematopoietic Cells via BMP Regulation," *Nat. Immunol.*, 2001, 2(2), 172-180.
Bhatia et al., "A Newly Discovered Class of Human Hematopoietic Cells with SCID-repopulating Activity," *Nat. Med.*, 1998, 4(9), 1038-1045.
Bhatia et al., "Purification of Primitive Human Hematopoietic Cells Capable of Repopulating Immune-deficient Mice," *Proc. Natl. Acad. Sci. USA*, 1997, 94, 5320-5325.
Calvi et al., "Osteoblastic Cells Regulate the Haematopoietic Stem Cell Niche," *Nature*, 2003, 425, 841-846.
Cheng et al., "Hematopoietic Stem Cell Quiescence Maintained by $p21^{cip1/waf1}$," *Science* 2000, 287, 1804-1808.
Cline et al., "Effects of a Novel Glycogen Synthase Kinase-3 Inhibitor on Insulin-Stimulated Glucose Metabolism in Zucker Diabetic Fatty (fa/fa) Rats," *Diabetes*, 2002, 51, 2903-2910.
Cohen et al., "GSK3 Inhibitors: Development and Therapeutic Potential," *Nat. Rev. Drug Dis.*, 2004, 3, 479-487.
Cohen, "The Hormonal Control of Glycogen Metabolism in Mammalian Muscle by Multivalent Phosphorylation," *Biochem. Soc. Trans.*, 1979, 7, 459-480.
Cohen et al., "Hematopoietic Stem-cell Transplantation Using Umbilical-cord Blood," *Leuk Lymphoma*. 2003, 44(8), 1287-1299.
DasGupta et al., "Multiple Roles for Activated LEF/TCF Transcription Complexes during Hair Follicle Development and Differentiation," *Development*, 1999, 126, 4557-4568.

(Continued)

*Primary Examiner*—Scott Long
(74) *Attorney, Agent, or Firm*—Nixon Peabody LLP

(57) ABSTRACT

Methods are provided for increasing stem cells, hematopoietic progenitor/stem cells, mesenchymal progenitor/stem cells, mesodermal progenitor/stem cells, muscle progenitor/stem cells, or neural progenitor/stem cells in vivo in a mammalian subject. Methods are also provided for treating an immune related disease, a mesenchymal/mesoderm degenerative disease, or a neurodegenerative disease in a mammalian subject in need thereof.

17 Claims, 26 Drawing Sheets

OTHER PUBLICATIONS

Derksen et al., "Illegitimate WNT Signaling Promotes Proliferation of Multiple Myeloma Cells," *Proc. Natl Acad. Sci. USA*, 2004, 101(16), 6122-6127.

Devine et al., "Clinical Application of Hematopoietic Progenitor Cell Expansion: Current Status and Future Prospects," *Bone Marrow Transplant*, 2003, 31, 241-252.

Dyer et al., "Indian Hedgehog Activates Hematopoiesis and Vasculogenesis and Can Respecify Prospective Neurectodermal Cell Fate in the Mouse Embryo," *Development*, 2001, 128, 1717-1730.

Emami et al., "A Small Molecule Inhibitor of β-catenin/CREB-binding Protein Transcription," *Proc. Natl Acad. Sci. USA*, 2004, 101(34), 12682-12687.

Embi et al., "Glycogen Synthase Kinase-3 from Rabbit Skeletal Muscle," *Eur. J. Biochem.*, 1980, 107, 519-527.

Espinosa et al., "Phosphorylation by Glycogen Synthase Kinase-3β Down-regulates Notch Activity, a Link for Notch and Wnt Pathways," *J. Biol. Chem.*, 2003, 278(34), 32227-32235.

Foltz et al., "Glycogen Synthase Kinase-3β Modulates Notch Signaling and Stability," *Curr. Biol.*, 2002, 12, 1006-1011.

Frame et al., "GSK3 Takes Centre Stage More Than 20 Years after its Discovery," *Biochem J.*, 2001, 359, 1-16.

Frank-Kamenetsky et al., "Small-molecule Modulators of Hedgehog Signaling: Identification and Characterization of Smoothened Agonists and Antagonists," *J. Biology*, 2002, 1(2), 10.1-10.19.

Giles et al., "Caught up in a Wnt Storm: Wnt Signaling in Cancer," *Biochim. Biophys. Acta*, 2003, 1653, 1-24.

Giralt, "Bone Marrow Transplant in Myelodysplastic Syndromes: New Technologies, Same Questions," *Curr Hematol Rep.*, 2004, 3, 165-172.

Gluckman, "Current Status of Umbilical Cord Blood Hematopoietic Stem Cell Transplantation," *Exp. Hematol.*, 2000, 28, 1197-1205.

Goodrich et al., "Altered Neural Cell Fates and Medulloblastoma in Mouse patched Mutants," *Science*, 1997, 277, 1109-1113.

Gunther et al., "Impact of p53 Loss on Reversal and Recurrence of Conditional Wnt, induced Tumorigenesis," *Genes Dev.*, 2003, 17, 488-501.

He et al., "A Monoclonal Antibody against Wnt-1 Induces Apoptosis in Human Cancer Cells," *Neoplasia*, 2004, 6(1), 7-14.

Issack et al., "Altered Expression of Helix-Loop-Helix Transcriptional Regulators and Cyclin D1 in Wnt-1-transformed PC12 Cells," *Cell Growth Differ.*, 1998, 9, 837-845.

Jarriault et al., "Signalling Downstream of Activated Mammalian Notch," *Nature*, 1995, 377, 355-358.

Jay et al., "Identification of a Novel Population of Human Corn Blood Cells with Hematopoietic and Chondrocytic Potential," *Cell Research*, 2004, 14(4), 268-282.

Jho et al., "Wnt/β-Catenin/Tcf Signaling Induces the Transcription of Axin2, a Negative Regulator of the Signaling Pathway," *Mol. Cell Biol.*, 2002, 22(4), 1172-1183.

Jia et al., "Shaggy/GSK3 Antagonists Hedgehog Signalling by Regulating Cubitus Interruptus," *Nature*, 2002, 416, 548-552.

Karanu et al., "Human Homologues of Delta-1 and Delta-4 Function as Mitogenic Regulators or Primitive Human Hematopoietic Cells," *Blood*, 2001, 97(7), 1960-1967.

Karanu et al., "The Notch Ligand Jagged-1 Represents a Novel Growth Factor of Human Hematopoietic Stem Cells," *J. Exp. Med.*, 2000, 192(9), 1365-1372.

Kim et al., "Proof-of-Principle: Oncogenic β-Catenin is a Valid Molecular Target for the Development of Pharmacological Inhibitors," *Mol. Cancer Ther.*, 2002, 1, 1355-1359.

King, "Roughing up Smoothened: Chemical Modulators of Hedgehog Signaling," *J. Biology*, 2002, 1(2), 8.1-8.4.

Larochelle et al., "Identification of Primitive Human Hematopoietic Cells Capable of Repopulating NOD/SCID Mouse Bone Marrow: Implications for Gene Therapy," *Nat. Med.*, 1996, 292(12), 1329-1337.

Lindsell et al., "Jagged: A Mammalian Ligand that Activates Notchl" *Cell*, 1995, 80, 909-917.

Marigo et al., "Sonic Hedgehog Differentially Regulates Expression of GLI and GLI3 during Limb Development," *Dev. Biol.*, 1996, 180, 273-283.

Marigo et al., "Regulation of Patched by Sonic Hedgehog in the Developing Neural Tube," *Proc. Natl. Acad. Sci. USA*, 1996, 93, 9346-9351.

Moon et al., "Wnt and β-Catenin Signalling: Diseases and Therapies," *Nature Reviews Genetics*, 2004, 5, 689-699.

Morrison et al., "The Long-term Repopulating Subset of Hematopoietic Stem Cells is Deterministic and Isolatable by Phenotype," *Immunity*, 1994, 1, 661-673.

Moscardo et al., "Unrelated-door Cord Blood Transplantation for Adult Hematological Malignancies," *Leuk Lymphoma*, 2004, 45(1), 11-18.

Murdoch et al., "Wnt-5A Augments Repopulating Capacity and Primitive Hematopoietic Development of Human Blood Stem Cells In Vivo," *Proc. Natl Acad. Sci. USA*, 2003, 100(6), 3422-3427.

Reya et al., "A Role for Wnt Signalling in Self-renewal of Haematopoietic Stem Cells," *Nature*, 2003, 423, 409-414.

Reya, "Regulation of Hematopoietic Stem Cell Self-Renewal," *Recent Prog Horm Res.*, 2003, 58, 283-295.

Ring et al., "Selective Glycogen Synthase Kinase 3 Inhibitors Potentiate Insulin Activation of Glucose Transport and Utilization In Vitro and In Vivo," *Diabetes*, 2003, 52, 588-595.

Sato et al., "Maintenance of Pluripotency in Human and Mouse Embryonic Stem Cells Through Activation of Wnt Signaling by a Pharmacological GSK-3-specific Inhibitor," *Nat. Med.*, 2004, 10(1), 55-63.

Schuringa et al., "Constitutive Activation of STAT5A Promotes Human Hematopoietic Stem Cell Self-Renewal and Erythroid Differentiation," *J. Exp. Med.*, 2004, 200(5), 623-635.

Shih et al., "Ex Vivo Expansion of Transplantable Human Hematopoietic Stem Cells: Where Do We Stand in the Year 2000?" *J. Hematother. Stem Cell Res.*, 2000, 9, 621-628.

Srour et al., "Ex Vivo Expansion of Hematopoietic Stem and Progenitor Cells: Are We There Yet?" *J. Hematother.*, 1999, 8, 93-102.

Stecca et al., "The Therapeutic Potential of Modulators of the Hedgehog-Gli Signaling Pathway," *J. Biology*, 2002, 1, 9.1-9.4.

Tsirigotis et al., "Analysis of Ubiquitination In Vivo Using a Transgenic Mouse Model," *Biotechniques*, 2001, 31, 120-127.

Uchida et al., "Searching for Hematopoietic Stem Cells: Evidence That Thy-1.1[lo] Lin Sca-1= Cells Are the Only Stem Cells in C57BL/Ka-Thy-1.1 Bone Marrow," *J. Exp. Med.*, 1992, 175, 175-184.

Varnum-Finney et al., "Pluripotent, Cytokine-dependent, Hematopoietic Stem Cells are Immortalized by Constitutive Notch1 Signaling," *Nat. Med.*, 2000, 6(11), 1278-1281.

Veeman et al., "Zebrafish Prickle, a Modulator of Noncanonical Wnt/Fz Signaling, Regulates Gastrulation Movements," *Current Biology*, 2003, 13, 680-685.

Veeman et al., "A Second Canon: Functions and Mechanisms of β-Catenin-Independent Wnt Signaling," *Dev. Cell.*, 2003, 5, 367-377.

Vollweiler et al., "Hematopoietic Stem Cell Gene Therapy: Progress Toward Therapeutic Targets," *Bone Marrow Transplant.*, 2003, 32, 1-7.

Yan et al., "Elevated Expression of axin2 and hnkd mRNA Provides Evidence that Wnt/β-catenin Signaling is Activated in Human Colon Tumors," *Proc. Natl. Acad. Sci. USA*, 2001, 98(26), 14973-14978.

Yost et al., "The Axis-inducing Activity, Stability, and Subcellular Distribution of β-catenin is Regulated in Xenopus Embryos by Glycogen Synthase Kinase 3," *Genes Dev.*, 1996, 10, 1443-1454.

You et al., "Inhibition of Wnt-2-mediated Signaling Induces Programmed Cell Death in Non-small-cell Lung Cancer Cells," *Oncogene*, 2004, 23, 6170-6174.

Dvory-Sobol et al., "Targeting the Active Beta-catenin Pathway to Treat Cancer Cells," Mol Cancer Ther 5 (11):2861-2871 (2006).

Cuzzocrea et al., "Glycogen Synthase Kinase 3Beta Inhibition Reduces the Development of Nonseptic Shock Induced by Zymosan in Mice," Shock 27(1):97-107 (2007).

Eisinger et al., "Retinoic Acid Inhibits Beta-catenin Through Suppression of Cox-2," J Biol Chem 282 (40):29394-29400 (2007).

Parkitna et al., "Effects of GSK2Beta and Cdk5 Kinase Inhibitors on Morphine-Induced Analgesia and Tolerance in Rats," American Society for Pharmacology and Experimental Therapeutics (2006).

Bax et al., "The Structure of Phosphorylated GSK-3Beta Complexed with a Peptide, FRATtide, that Inhibits Beta-catenin Phosphorylation," Structure 9:1143-1152 (2001).

Gould et al., "Glycogen Synthase Kinase-3: A Putative Molecular Target for Lithium Mimetic Drugs," Neuropsychopharmacology 1-5 (2005).

Carmichael et al., "Glycogen Synthase Kinase -3Beta Inhibitors Prevent Cellular Polyglutamine Toxicity Caused by the Huntington's Disease Mutation," J Biol Chem 277(37):33791-33798 (2002).

Beaulieu et al., "Not Only Lithium: Regulation of Glycogen Synthase Kinase-3 by Antipsychotics and Serotonergic Drugs," International Journal of Neuropsychopharmacology 1-4 (2006).

Trowbridge et al., "Glycogen Synthase Kinase-3 is in In vivo Regulator of Hematopoietic Stem Cell Repopulation," Nature Medicine 12(1):89-98 (2006).

Topol et al., "Wnt-5a Inhibits the Canonical Wnt Pathway by Promoting GSK-3-independent Beta-catenin Degradation," J. Cell Biol. 162(5):899-908 (2003).

Anton et al., "Beta-catenin Signaling Contributes to Stemness and Regulates Early Differentiation in Murine Embryonic Stem Cells," FEBS Letters 581:5247-5254 (2007).

Jamieson et al., "Granulocyte-macrophage Progenitors as Candidate Leukemic Stem Cells in Blast-Crisis CML," N. Engl. J. Med. 351:657-667 (2004).

Frame et al., "GSK3 Takes Centre Stage More Than 20 Years After its Discovery," Biochem. J. 359:1-16 (2001).

Selenica et al., "Efficacy of Small-molecule Glycogen Synthase Kinase-3 Inhibitors in the Postnatal Rat Model of Tau Hyperphosphorylation," British Journal of Pharmacology 152:959-979 (2007).

Meijer et al., "GSK-3-selective Inhibitors Derived from Tyrian Purple Indirubins," Chemistry & Biology 10:1255-1266 (2003).

Kalia et al., "Hydrolytic Stability of Hydrazones and Oximes," Angew. Chem. Int. Ed. 47:7523-7526 (2008).

Heberling et al., "Oxygen-insensitive Enzymatic Reduction of Oximes to Imines," Biochemical Pharmacology 71:354-365 (2006).

D'Amour et al., "Genetic and Functional Differences Between Multipotent Neural and Pluripotent Embryonic Stem Cells," Proc. Nat'l. Acad. Sci. USA 100:11866-11872 (2003).

Ramalho-Santos et al., "Stemness: Transcriptional Profiling of Embryonic and Adult Stem Cells," Science 298:587-600 (2002).

Shin et al., "Whole Genome Analysis of Human Neural Stem Cells Derived from Embryonic Stem Cells and Stem and Progenitor Cells Isolated from Fetal Tissue," Stem Cells 25:1298-1306 (2007).

Gronthos et al., "Stem Cell Properties of Human Dental Pulp Stem Cells," J. Dent. Res. 81:531-535 (2002).

Pittenger et al., "Mesenchymal Stem Cells and Their Potential as Cardiac Therapeutics," Circ. Res. 95:9-20 (2004).

Pare et al., "Biological Principles for Ex vivo Adult Stem Cell Expansion," Current Topics in Developmental Biology 73:141-171 (2006).

Mussmann et al., "Inhibition of GSK3 Promotes Replication and Survival of Pancreatic Beta Cells," J. Biol. Chem. 282(16):12030-12037 (2007).

Fleming et al., "Wnt Signaling in the Niche Enforces Hematopoietic Stem Cell Quiescence and is Necessary to Preserve Self-renewal In vivo," Cell Stem Cell 2:274-283 (2008).

Suda et al., "Wnt Signaling in the Niche," Cell 132:729-730 (2008).

Uedo et al., "Biphasic Role for Wnt/Beta-catenin Signaling in Cardiac Specification in Zebrafish and Embryonic Stem Cells," Proc. Nat'l. Acad. Sci. USA 104(23):9685-9690 (2007).

Slavik et al., "Wnt Signaling Induces Differentiation of Progenitor Cells in Organotypic Keratinocyte Cultures," BMC Developmental Biology 7(9):1-8 (2007).

Matushansky et al., "A Context Dependent Role for Wnt Signaling in Tumorigenesis and Stem Cells," Cell Cycle 7 (6):720-724 (2008).

Kelly et al., "Glycogen Synthase Kinase 3Beta Inhibitor Chir025 Reduces Neuronal Death Resulting from Oxygen-glucose Deprivation, Glutamate Excitotoxicity, and Cerebral Ischemia," Experimental Neurology 188:378-386 (2004).

International Search Report for PCT/US05/45708 (Dec. 1, 2006).

Written Opinion for PCT/US2005/047508 (Jul. 3, 2007).

Extended European Search Report for EP 05855989.9 (Aug. 11, 2008).

Eldar-Finkelman, "Glycogen Synthase Kinase 3: An Emerging Therapeutic Target," Trends Mol. Med. 8 (3):126-132 (2002).

Ivanova et al., "A Stem Cell Molecular Signature," with Supporting Online Material, Science 298:601-604 (2002).

Kaku et al., "GSK-3 Inhibitors: Recent Developments and Therapeutic Potential," Current Signal Transduction Therapy 3(3):195-205 (2008) (abstract only).

Kulkarni et al., "Orally Bioavailable GSK-3 Alpha/Beta Dual Inhibitor Increases Markers of Cellular Differentiation In Vitro and Bone Mass In Vivo," J. Bone Miner. Res. 21(6):910-920 (2006).

Mohan, "Alzheimer's and Other Neurodegenerative Disease Research Tools," EMD Biosciences, Inc. pp. 1-32 (2003).

Patel et al., "Glycogen Synthase Kinase-3 in Insulin and Wnt Signalling: a Double-Edged Sword?" Biochem. Soc. Trans. 32(5):803-808 (2004).

Ramalho-Santos et al., "Stemness': Transcriptional Profiling of Embryonic and Adult Stem Cells," Science 298:597-600 (2002).

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Forward primer

<400> SEQUENCE: 1
ttcaccacca tggagaaggc                                              20

<210> SEQ ID NO 2
<211> LENGTH: 20
<212> TYPE: DNA
<213> ORGANISM: Artificial
<220> FEATURE:
<223> OTHER INFORMATION: Reverse primer

<400> SEQUENCE: 2
ggcatggact gtggtcatga                                              20

<210> SEQ ID NO 3
<211> LENGTH: 20
<212> TYPE: DNA
<213> ORGANISM: Artificial
<220> FEATURE:
<223> OTHER INFORMATION: Forward primer

<400> SEQUENCE: 3
aacctatgcc cgtttcctct                                              20
```

```
<210> SEQ ID NO 4
<211> LENGTH: 20
<212> TYPE: DNA
<213> ORGANISM: Artificial
<220> FEATURE:
<223> OTHER INFORMATION: Reverse primer

<400> SEQUENCE: 4
ctggtcaccc aacaaggagt                                                    20

<210> SEQ ID NO 5
<211> LENGTH: 20
<212> TYPE: DNA
<213> ORGANISM: Artificial
<220> FEATURE:
<223> OTHER INFORMATION: Forward primer

<400> SEQUENCE: 5
agtgcgtgca gaaggagatt                                                    20

<210> SEQ ID NO 6
<211> LENGTH: 20
<212> TYPE: DNA
<213> ORGANISM: Artificial
<220> FEATURE:
<223> OTHER INFORMATION: Reverse primer

<400> SEQUENCE: 6
cacaacttct cggcagtcaa                                                    20

<210> SEQ ID NO 7
<211> LENGTH: 20
<212> TYPE: DNA
<213> ORGANISM: Artificial
<220> FEATURE:
<223> OTHER INFORMATION: Forward primer

<400> SEQUENCE: 7
ctaccccagc cagtgtcaac                                                    20

<210> SEQ ID NO 8
<211> LENGTH: 20
<212> TYPE: DNA
<213> ORGANISM: Artificial
<220> FEATURE:
<223> OTHER INFORMATION: Reverse primer

<400> SEQUENCE: 8
atgccgggag ctatctttct                                                    20

<210> SEQ ID NO 9
<211> LENGTH: 20
<212> TYPE: DNA
<213> ORGANISM: Artificial
<220> FEATURE:
<223> OTHER INFORMATION: Forward primer

<400> SEQUENCE: 9
tgcccatcag ctactcagtg                                                    20

<210> SEQ ID NO 10
<211> LENGTH: 20
<212> TYPE: DNA
<213> ORGANISM: Artificial
<220> FEATURE:
<223> OTHER INFORMATION: Reverse primer
```

```
<400> SEQUENCE: 10
ttgttgcaga gtgaggttgc                                              20

<210> SEQ ID NO 11
<211> LENGTH: 20
<212> TYPE: DNA
<213> ORGANISM: Artificial
<220> FEATURE:
<223> OTHER INFORMATION: Forward primer

<400> SEQUENCE: 11
ctcaggcaat acgaagcaca                                              20

<210> SEQ ID NO 12
<211> LENGTH: 20
<212> TYPE: DNA
<213> ORGANISM: Artificial
<220> FEATURE:
<223> OTHER INFORMATION: Reverse primer

<400> SEQUENCE: 12
gacaaggagc cagagtccag                                              20
```

METHODS FOR REGULATION OF STEM CELLS

FIELD

The invention generally relates to methods for increasing the successful activity of stem cells, hematopoietic progenitor/stem cells, mesenchymal progenitor/stem cells, mesodermal progenitor/stem cells, muscle progenitor/stem cells, or neural progenitor/stem cells in vivo in a mammalian subject. The invention further relates to methods of treating an immune related disease, a mesenchymal/mesoderm degenerative disease, or a neurodegenerative disease by administering one or more Wnt/β-catenin signal-, Notch signal- or Hedgehog signal-promoting agents to a mammalian subject in need thereof.

BACKGROUND

Hematopoietic stems cells (HSCs) are rare cells of the hematopoietic system with the ability to self-renew and differentiate into all mature blood lineages, thereby sustaining hematopoietic homeostasis and immune function. HSC transplantation therapy has been effectively used to manage hematopoietic malignancies, bone marrow/hematopoietic failure, and immunodeficiency. Baron et al., *Arch Med Res* 34:528-44, 2003; Giralt, *Curr Hematol Rep* 3:165-72, 2004; Vollweiler et al., *Bone Marrow Transplant* 32:1-7, 2003. Despite successful utility of HSCs, several clinical limitations remain. These include availability of allogenic HSC donors and inability to harvest adequate numbers of HSCs per donor. Moscardo et al., *Leuk Lymphoma* 45:11-8, 2004. Although autologous harvests of HSCs via G-CSF mobilization to the peripheral blood have alleviated some of the clinical burden for allogenic HSC transplantation, many patients remain refractory to mobilization and subsequent HSC reconstitution. Cohena and Nagler, *Leuk Lymphoma* 44:1287-99, 2003. Ex vivo expansion of HSCs has been suggested as a means to increase the number of available HSCs for autologous or allogenic transplantation. Unfortunately, current methods of ex vivo HSC expansion have not proven to benefit transplanted recipients, and experimental evidence suggests that ex vivo culture of HSCs negatively affects their hematopoietic reconstitution ability. Devine et al., *Bone Marrow Transplant* 31:241-52, 2003; Shih et al., *J Hematother Stem Cell Res* 9:621-8, 2000; Srour et al., *J Hematother* 8:93-102, 1999.

Direct in vivo targeting of patient HSCs would provide a more physiological context to modulate HSC function as an alternative to HSC isolation and ex vivo manipulation. However, the current understanding of extrinsic regulators of HSCs has been derived from studies limited to ex vivo culture systems where HSCs are studied in suboptimal and artificial culture systems. As such, many factors implicated in regulating HSC self-renewal in vitro are not amenable to in vivo use.

Glycogen synthase kinase-3 (GSK-3) is a constitutively active serine/threonine kinase, originally identified as inactivating glycogen synthase. Frame and Cohen, *Biochem J* 359:1-16, 2001; Cohen, *Biochem Soc Trans* 7:459-80, 1979; Embi et al., *Eur J Biochem* 107:519-27, 1980. Inhibition of GSK-3 has been implicated in regulation of several pathways, including Wnt, Hedgehog, and Notch. Behrens et al., *Science* 280:596-599, 1998; Yost et al., *Genes Dev* 10: 1443-1454, 1996; Jia et al., *Nature* 416:548-552, 2002; Foltz et al., *Curr Biol* 12:1006-1011, 2002; Espinosa et al., *J Biol Chem* 278:32227-35, 2003. Important to HSCs, these same pathways have recently been associated with HSC function by either forced ectopic overexpression of key upstream regulators of these pathways, or ligand presentation in vitro. Murdoch et al., *PNAS* 100:3422-3427, 2003; Reya et al., *Nature* 423:409-14, 2003; Bhardwaj et al., *Nat Immunol* 2:172-80, 2001; Karanu et al., *J Exp Med* 192:1365-72, 2000; Karanu et al., *Blood* 97:1960-7, 2001; Cline et al., *Diabetes* 51:2903-2910, 2002; Ring et al., *Diabetes* 52:588-595, 2003.

Degenerative muscle diseases, such as muscular dystrophy (MD) include a group of genetic diseases characterized by progressive weakness and degeneration of the skeletal muscles which control movement. There is no specific treatment for any of the forms of MD. Respiratory therapy, physical therapy to prevent painful muscle contractures, orthopedic appliances used for support, and corrective orthopedic surgery may improve the quality of life in some cases. Myopathy is a neuromuscular disorder in which the primary symptom is muscle weakness due to dysfunction of muscle fiber. Treatments for the myopathies depend on the disease or condition and specific causes. Supportive and symptomatic treatment may be the only treatment available or necessary for some disorders.

Regulators of hematopoietic stem cells (HSCs), stem cells, that elicit their effects in vivo have not been identified, limiting clinical manipulation of HSCs to ex vivo systems. Regulators of muscle progenitor cells or neural progenitor cells for in vivo treatment of degenerative muscle diseases or neurodegenerative diseases have not been identified. A need exists in the art for an improved therapy involving hematopoietic stem cell for treatment of immune related disease, and for an improved therapy involving stem cells, muscle progenitor cells or neural progenitor cells for treatment of degenerative muscle diseases or neurodegenerative diseases.

SUMMARY

The present invention relates to a method for increasing the successful activity of stem cells and progenitor cells, for example, hematopoietic progenitor/stem cells (HSCs), mesenchymal progenitor/stem cells, mesodermal progenitor/stem cells, endothelial progenitor/stem cells, or ectodermal or neural progenitor/stem cells in vivo in a mammalian subject comprising interacting one or more Wnt/β-catenin signal-, Notch signal- or Hedgehog signal-promoting agents with the progenitor/stem cells in the mammalian subject and increasing the progenitor/stem cells in the mammalian subject. The progenitor/stem cells can include, but are not limited to, hematopoietic progenitor/stem cells (HSCs), stem cells, mesenchymal progenitor/stem cells, mesodermal progenitor/stem cells, endlthelial progenitor/stem cells, ectodermal progenitor/stem cells, muscle progenitor/stem cells, endodermal progenitor/stem cells or neural progenitor /stem cells The interacting of one or more Wnt/β-catenin signal-, Notch signal- or Hedgehog signal-promoting agents with progenitor/stem cells, e.g., hematopoietic progenitor/stem cells, occurs either by direct interaction of the signal promoting agents with the hematopoietic progenitor/stem cells or through an indirect interaction between a second signaling factor or cell type acting as an intermediate between the Wnt/β-catenin signal-, Notch signal- or Hedgehog signal-promoting agents and the hematopoietic progenitor/stem cells. Whether the effect on the HSC, or progenitor/stem cell, is on progenitor/stem cell proliferation, survival, cell differentiation, or engraftment into the target tissue, the net effect of activating the Wnt/β-catenin signal is an increase in the measured stem cell/progenitor cell activity. A progenitor/stem cell, e.g., an hematopoietic progenitor/stem cell, can be derived from a variety of sources, including, but not limited to, adult bone marrow, umbilical cord blood cells, or embryonic stem cells, from a mammal, e.g., a human. A method of treating immune related disease is provided comprising administering one or more Wnt/β-catenin signal-, Notch signal- or Hedgehog signal-promoting agents to a mammalian subject and interacting the agent with the hematopoietic progenitor/stem cells of the mammalian subject. A method of treating degenerative disease is provided comprising administering one or more Wnt/β-catenin signal-, Notch signal- or Hedgehog signal-promoting agents to a mammalian subject and interacting the agent with hematopoietic progenitor/stem cells, stem cells, mesenchymal progenitor cells, mesodermal progenitor cells, muscle progenitor cells, endothelial progenitor cells, or neural progenitor cells of the mammalian subject. The degenerative disease includes, but is not limited to, mesenchymal degenerative disease, mesodermal degenerative disease, muscle degenerative disease, endothelial degenerative disease, or neurodegenerative disease.

A method for increasing hematopoietic stem cells in vivo in a mammalian subject is provided which comprises interacting one or more Wnt/β-catenin signal-, Notch signal- or Hedgehog signal-promoting agents with the hematopoietic stem cells in the mammalian subject and increasing the hematopoietic stem cells in the mammalian subject compared to the hematopoietic stem cells in the mammalian subject before treatment. In one aspect, the Wnt/β-catenin signal-promoting agent is an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16. In a further aspect, the Wnt/β-catenin signal-promoting agent is an agonist of Wnt3a or Wnt8. In another aspect, the Notch signal-promoting agent is an agonist of Notch, Delta, Serrate, Jagged, Deltex, Mastermind, Enhancer of Split, Hes1, Split, Hairless, Suppressor of Hairless, or RBP-Jk. In another aspect, the Hedgehog signal-promoting agent is an agonist of Desert hedgehog, Sonic hedgehog, Indian hedgehog, Gli, Gli-1, Gli-3, Patched, or Patched1.

The method for increasing hematopoietic stem cells in vivo in a mammalian subject further provides increasing hematopoietic stem cells in the subject as a result of cell proliferation, cell homing, decreased apoptosis, self renewal, or increased cell survival. In a further aspect, the hematopoietic stem cells comprise progenitor cells of erythroid cells, granulocyte cells, macrophage cells, granulocyte-macrophage cells, B cells, T cells, and multipotent mixed lineage colony types The method for increasing hematopoietic stem cells in vivo in a mammalian subject further provides that the Wnt/β-catenin signal-, Notch signal- or Hedgehog signal-promoting agent is a polypeptide, nucleic acid, small molecule, antisense oligonucleotide, ribozyme, RNAi construct, siRNA, shRNA, or antibody. In a one aspect, the Wnt signal- or β-catenin signal-promoting agent is a polypeptide, for example, a wnt polypeptide, a dishevelled polypeptide, or a β-catenin polypeptide. In a further aspect, the Notch signal-promoting agent is a notch polypeptide, delta polypeptide, serrate polypeptide, jagged polypeptide, deltex polypeptide, mastermind polypeptide, split polypeptide, hairless polypeptide, RBP-Jk polypeptide, or hes1 polypeptide. In a further aspect, the Hedgehog signal-promoting agent is a desert hedgehog polypeptide, sonic hedgehog polypeptide, indian hedgehog polypeptide, gli polypeptide, gli-1 polypeptide, gli-3 polypeptide, patched polypeptide, or patched1 polypeptide.

The method for increasing hematopoietic stem cells in vivo in a mammalian subject further provides that the Wnt/β-catenin signal-, Notch signal- or Hedgehog signal-promoting agent is a glycogen synthase kinase (GSK) inhibitor. In a further aspect, the glycogen synthase kinase (GSK) inhibitor is a GSK-3 inhibitor or a GSK-3β inhibitor.

A method is provided for treating an immune related disease in a mammalian subject in need thereof comprising administering one or more Wnt/β-catenin signal-, Notch signal- or Hedgehog signal-promoting agents to the subject, and interacting the one or more Wnt/β-catenin signal-, Notch signal- or Hedgehog signal-promoting agents with hematopoietic stem cells, and thereby increasing in vivo hematopoietic stem cells in the subject to treat the immune related disease compared to the hematopoietic stem cells in the mammalian subject before treatment. In a further aspect, the method comprises increasing hematopoietic stem cells in the subject as a result of cell proliferation, cell homing, decreased apoptosis, self renewal, or increased cell survival. In a further aspect, the immune related disease is diabetes, graft vs. host disease, immunodeficiency disease, hematopoietic malignancy, hematopoietic failure, or hematopoietic stem cell transplantation.

A method is provided for treating an immune related disease in a mammalian subject in need thereof comprising administering hematopoietic stem cells to the subject, administering to the subject one or more Wnt/β-catenin signal-, Notch signal- or Hedgehog signal-promoting agents to contact the hematopoietic stem cells in the subject, and interacting the one or more Wnt/β-catenin signal-, Notch signal- or Hedgehog signal-promoting agents with hematopoietic stem cells, and increasing in vivo hematopoietic stem cells in the subject to treat the immune related disease compared to the hematopoietic stem cells in the mammalian subject before treatment. In a further aspect, the method comprises increasing hematopoietic stem cells in the subject as a result of cell proliferation, cell homing, decreased apoptosis, self renewal, or increased cell survival. In one aspect, the hematopoietic stem cells are neonatal cells, umbilical cord blood cells, fetal liver cells, adult cells, bone marrow cells, peripheral blood cells, or embryonic stem cells. In a further aspect, the hematopoietic stem cells are autologous or allogeneic hematopoietic stem cells. In a further aspect, the immune related disease is diabetes, graft vs. host disease, immunodeficiency disease, hematopoietic malignancy, hematopoietic failure, or hematopoietic stem cell transplantation.

A method is provided for treating a degenerative disease in a mammalian subject in need thereof comprising administering one or more Wnt/β-catenin signal-, Notch signal- or Hedgehog signal-promoting agents to the subject, and increasing in vivo one or more mesenchymal progenitor/stem cells, mesodermal progenitor/stem cells or endothelial progenitor/stem cells in the subject to treat the degenerative disease compared to the progenitor/stem cells in the mammalian subject before treatment. In a further aspect, the method comprises increasing progenitor/stem cells in the subject as a result of cell proliferation, cell homing, decreased apoptosis, self renewal, or increased cell survival.

In a further aspect, the method comprises increasing in vivo one or more mesenchymal progenitor/stem cells or mesodermal progenitor/stem cells in the subject to treat degenerative muscle disease or to treat degenerative mesenchymal disease. In one aspect, the degenerative mesenchymal disease is treated by increasing or repairing bone, chondrocytes/cartilage, skeletal muscle, endothelial cells, or adipose cells. In a further aspect, the method comprises increasing in vivo one or more endothelial progenitor/stem cells in the subject to treat degenerative endothelial disease. In one aspect, the degenerative endothelial disease is treated by increasing vascularization or increasing angiogenesis.

In one aspect, the degenerative muscle disease is muscular dystrophy, duchenne muscular dystrophy, facioscapulohumeral muscular dystrophy, myotonic muscular dystrophy, congenital myopathy, or mitochondrial myopathy. In a further aspect, the degenerative muscle disease is familial cardiomyopathy, dilated cardiomyopathy, hypertrophic cardiomyopathy, restrictive cardiomyopathy, or coronary artery disease with resultant ischemic cardiomyopathy. In a further aspect, the method comprises increasing in vivo one or more mesenchymal progenitor/stem cells or mesodermal progenitor/stem cells in the subject to treat degenerative liver disease, nephritic disease, cirrhosis, alcoholic cirrhosis, fatty liver, alcoholic hepatitis, viral hepatitis, liver carcinoma, post necrotic cirrhosis, biliary cirrhosis, hepatocellular injury or a biliary tract disorder. In a further aspect, the method comprises increasing in vivo one or more mesenchymal progenitor/stem cells or mesodermal progenitor/stem cells in the subject to treat degenerative pancreatic disease, diabetes, diabetes related disorder, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, or osteoporosis.

A method is provided for treating a degenerative disease in a mammalian subject in need thereof comprising administering one or more mesenchymal progenitor/stem cells, mesodermal progenitor/stem cells or endothelial progenitor/stem cells to the subject, administering to the subject one or more Wnt/β-catenin signaling, Notch signaling or Hedgehog signaling promoting agents to contact the progenitor/stem cells in the subject, and interacting the one or more Wnt/β-catenin signaling, Notch signaling or Hedgehog signaling promoting agents with the progenitor/stem cells, and increasing in vivo progenitor/stem cells in the subject to treat the degenerative disease compared to the progenitor/stem cells in the mammalian subject before treatment. In one aspect, the progenitor/stem cells are neonatal cells, umbilical cord blood cells, fetal liver cells, adult cells, bone marrow cells, peripheral blood cells, or embryonic stem cells. In a further aspect, the muscle progenitor cells or stem cells are autologous or allogeneic muscle progenitor cells/stem cells. In a further aspect, the method comprises increasing progenitor/stem cells in the subject as a result of cell proliferation, cell homing, decreased apoptosis, self renewal, or increased cell survival.

In a further aspect, the method comprises increasing in vivo one or more mesenchymal progenitor/stem cells or mesodermal progenitor/stem cells in the subject to treat degenerative muscle disease, muscular dystrophy, duchenne muscular dystrophy, facioscapulohumeral muscular dystrophy, myotonic muscular dystrophy, congenital myopathy, or mitochondrial myopathy. In one aspect, the degenerative muscle disease is familial cardiomyopathy, dilated cardiomyopathy, hypertrophic cardiomyopathy, restrictive cardiomyopathy, or coronary artery disease with resultant ischemic cardiomyopathy. In a further aspect, the method comprises increasing in vivo one or more mesenchymal progenitor/stem cells or mesodermal progenitor/stem cells in the subject to treat degenerative liver disease, nephritic disease, cirrhosis, alcoholic cirrhosis, fatty liver, alcoholic hepatitis, viral hepatitis, liver carcinoma, post necrotic cirrhosis, biliary cirrhosis, hepatocellular injury or a biliary tract disorder.

In a further aspect, the method comprises increasing in vivo one or more mesodermal progenitor/stem cells in the subject to treat degenerative pancreatic disease, diabetes, diabetes related disorder, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, or osteoporosis.

In a further aspect, the method comprises increasing in vivo one or more mesenchymal progenitor/stem cells in the subject to treat degenerative mesenchymal disease. In one aspect, the degenerative mesenchymal disease is treated by increasing or repairing bone, increasing or repairing chondrocytes/cartilage, increasing or repairing skeletal muscle, increasing or repairing endothelial cells, or increasing or repairing adipose cells. In a further aspect, the method comprises increasing in vivo one or more endothelial progenitor/stem cells in the subject to treat degenerative endothelial disease. In one aspect, the degenerative endothelial disease is treated by increasing vascularization or increasing angiogenesis.

A method is provided for treating a neurodegenerative disease in a mammalian subject in need thereof comprising administering one or more Wnt/β-catenin signal-, Notch signal- or Hedgehog signal-promoting agents to the subject, and increasing in vivo one or more neural progenitor/stem cells in the subject to treat the neurodegenerative disease compared to the neural progenitor/stem cells in the mammalian subject before treatment. In a further aspect, the method comprises increasing neural progenitor/stem cells in the subject as a result of cell proliferation, cell homing, decreased apoptosis, self renewal, or increased cell survival. In one aspect, the neurodegenerative disease is Alzheimer's disease, Parkinson's disease, Huntington's disease, multiple sclerosis (MS), or amyotrophic lateral sclerosis.

A method is provided for treating a neurodegenerative disease in a mammalian subject in need thereof comprising administering neural progenitor/stem cells to the subject, administering to the subject one or more Wnt/β-catenin signal-, Notch signal- or Hedgehog signal-promoting agents to contact the neural progenitor/stem cells in the subject, and interacting the one or more Wnt/β-catenin signal-, Notch signal- or Hedgehog signal-promoting agents with the neural progenitor/stem cells, and increasing in vivo neural progenitor/stem cells in the subject to treat the neurodegenerative disease compared to the neural progenitor/stem cells in the mammalian subject before treatment. In one aspect, neural progenitor/stem cells are autologous or allogeneic progenitor/stem cells. In a further aspect, the neural progenitor/stem cells are neonatal cells, umbilical cord blood cells, adult cells, bone marrow cells, peripheral blood cells, or embryonic stem cells. In a further aspect, the method comprises increasing neural progenitor/stem cells in the subject as a result of cell proliferation, cell homing, decreased apoptosis, self renewal, or increased cell survival. In one aspect, the neurodegenerative disease is Alzheimer's disease, Parkinson's disease, Huntington's disease, multiple sclerosis (MS), or amyotrophic lateral sclerosis.

A method is provided for treating leukemia disease in a mammalian subject in need thereof comprising administering one or more Wnt/β-catenin signal-, Notch signal- or Hedgehog signal-promoting agents to the subject, and decreasing in vivo proliferation of leukemic progenitor/stem cells in the subject to treat the leukemia disease compared to the leukemic progenitor/stem cells in the mammalian subject before treatment.

A method is provided for treating leukemia disease in a mammalian subject in need thereof comprising administering hematopoietic progenitor/stem cells to the subject, administering to the subject one or more Wnt/β-catenin signal-, Notch signal- or Hedgehog signal-promoting agents to contact the hematopoietic progenitor/stem cells in the subject, and interacting the one or more Wnt/β-catenin signal-, Notch signal- or Hedgehog signal-promoting agents with the hematopoietic progenitor/stem cells, and decreasing in vivo proliferation of leukemic progenitor/stem cells in the subject to treat the leukemia disease compared to the leukemic progenitor/stem cells in the mammalian subject before treatment. In one aspect, the leukemia disease is chronic myelogenous leukemia.

For the methods provided for treating an immune related disease in a mammalian subject, for treating a degenerative disease related to hematopoietic progenitor/stem cells, mesenchymal progenitor/stem cells, mesodermal progenitor/stem cells or endothelial progenitor/stem cells, for treating a neurodegenerative disease, or for treating a leukemic disease, one or more Wnt/β-catenin signaling, Notch signaling or Hedgehog signaling promoting agents are administered to the mammalian subject to contact the progenitor/stem cells in the subject. In one aspect, the Wnt signal- or β-catenin signal-promoting agent is an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt 11, Wnt14, Wnt15, or Wnt16. In a further aspect, the Notch signal-promoting agent is an agonist of Notch, Delta, Serrate, Jagged, Deltex, Mastermind, Enhancer of Split, Hes1, Split, Hairless, Suppressor of Hairless, or RBP-Jk. In a further aspect, the Hedgehog signal-promoting agent is an agonist of Desert hedgehog, Sonic hedgehog, Indian hedgehog, Gli, Gli-1, Gli-3, Patched, or Patched1.

In one aspect, the Wnt/β-catenin signal-, Notch signal- or Hedgehog signal promoting agent is a polypeptide, nucleic acid, small molecule, antisense oligonucleotide, ribozyme, RNAi construct, siRNA, shRNA, or antibody. In a further aspect, the Wnt/β-catenin signal-, Notch signal- or Hedgehog signal promoting agent is a polypeptide. The Wnt signal- or β-catenin signal-promoting agent provided in a further aspect is a wnt polypeptide, a dishevelled polypeptide, or a β-catenin polypeptide.

In a further aspect, the Wnt/β-catenin signal-, Notch signal- or Hedgehog signal promoting agent is a glycogen synthase kinase (GSK) inhibitor. In a further aspect, the glycogen synthase kinase (GSK) inhibitor is a GSK-3 inhibitor or a GSK-3β inhibitor.

A method is provided for identifying a test compound that increases hematopoietic progenitor/stem cells in a mammalian subject comprising interacting a test compound to a hematopoietic progenitor/stem cell in a cell-based assay system, assaying for an effect of the test compound on Wnt/β-catenin signaling, Notch signaling or Hedgehog signaling in the cell-based assay system and on modulating hematopoietic progenitor/stem cells, thereby identifying compounds that increase hematopoietic progenitor/stem cells in the mammalian subject compared to the hematopoietic stem cells in the mammalian subject before treatment.

A method is provided for screening drug candidates in a mammalian subject comprising administering a therapeutically effective amount of a compound to the mammalian subject wherein the compound acts as an activator of Wnt/β-catenin signaling, Notch signaling or Hedgehog signaling, and wherein the compound increases hematopoietic progenitor/stem cells in a cell-based assay system compared to the hematopoietic stem cells in the mammalian subject before treatment.

A method is provided for screening drug candidates in a mammalian subject comprising administering a therapeutically effective amount of a compound to the mammalian subject wherein the compound acts as an activator of Wnt/β-catenin signaling, Notch signaling or Hedgehog signaling, and wherein the compound increases hematopoietic progenitor/stem cells in the mammalian subject compared to the hematopoietic stem cells in the mammalian subject before treatment.

DETAILED DESCRIPTION

Figure 1A:
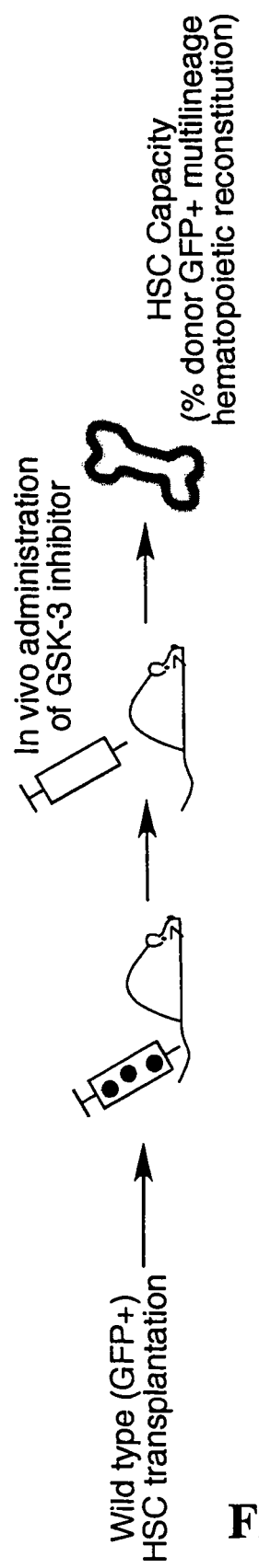
FIGS. 1a, 1b, 1c, 1d, and 1e show that in vivo administration of GSK-3 inhibitor augments wild type HSC repopulating capacity.

The invention generally relates to a method for increasing the successful activity of stem cells and progenitor cells, for example, hematopoietic progenitor/stem cells (HSCs), mesenchymal progenitor/stem cells, mesodermal progenitor/stem cells, endothelial progenitor/stem cells, or ectodermal or neural progenitor/stem cells in vivo in a mammalian subject comprising interacting one or more Wnt/β-catenin signal-, Notch signal- or Hedgehog signal-promoting agents with the progenitor/stem cells in the mammalian subject and increasing the progenitor/stem cells in the mammalian subject. The progenitor/stem cells can include, but are not limited to, hematopoietic progenitor/stem cells (HSCs), stem cells, mesenchymal progenitor/stem cells, mesodermal progenitor/stem cells, endothelial progenitor/stem cells, ectodermal progenitor/stem cells, muscle progenitor/stem cells, endodermal progenitor/stem cells or neural progenitor /stem cells The interacting of one or more Wnt/β-catenin signal-, Notch signal- or Hedgehog signal-promoting agents with progenitor/stem cells, e.g., hematopoietic progenitor/stem cells, occurs either by direct interaction of the signal promoting agents with the hematopoietic progenitor/stem cells or through an indirect interaction between a second signaling factor or cell type acting as an intermediate between the Wnt/β-catenin signal-, Notch signal- or Hedgehog signal-promoting agents and the hematopoietic progenitor/stem cells. Whether the effect on the HSC, or progenitor/stem cell, is on progenitor/stem cell proliferation, survival, cell differentiation, or engraftment into the target tissue, the net effect of activating the Wnt/β-catenin signal is an increase in the measured stem cell/progenitor cell activity. A progenitor/stem cell, e.g., an hematopoietic progenitor/stem cell, can be derived from a variety of sources, including, but not limited to, adult bone marrow, umbilical cord blood cells, or embryonic stem cells, from a mammal, e.g., a human. A method of treating immune related disease is provided comprising administering one or more Wnt/β-catenin signal-, Notch signal- or Hedgehog signal-promoting agents to a mammalian subject and interacting the agent with the hematopoietic progenitor/stem cells of the mammalian subject. A method of treating degenerative disease is provided comprising administering one or more Wnt/β-catenin signal-, Notch signal- or Hedgehog signal-promoting agents to a mammalian subject and interacting the agent with hematopoietic progenitor/stem cells, stem cells, mesenchymal progenitor cells, mesodermal progenitor cells, muscle progenitor cells, endothelial progenitor cells, or neural progenitor cells of the mammalian subject. The degenerative disease includes, but is not limited to, mesenchymal degenerative disease, mesodermal degenerative disease, muscle degenerative disease, endothelial degenerative disease, or neurodegenerative disease.

Regulators of hematopoietic progenitor/stem cells (HSCs) that elicit their effects in vivo have yet to be identified, limiting clinical manipulation of HSCs to ex vivo systems. HSC function can be augmented by administration of Wnt/β-catenin signal-, Notch signal- or Hedgehog signal-promoting agents, e.g., glycogen synthase kinase-3 (GSK-3) inhibitors, to recipient mice transplanted with either wild-type mouse reconstituting HSCs or human HSCs. Utilizing mouse reporter models and direct treatment of purified HSCs, GSK-3 inhibitors proved to enhance HSC activity and modulate gene targets of the Wnt, Hedgehog, and Notch pathways, without affecting more mature hematopoietic cells. This study establishes GSK-3 as a specific modulator of HSC activity, capable of Wnt, Hedgehog, and Notch pathway regulation. Administration of GSK-3 inhibitors of any chemical nature can provide a clinical approach to enhance HSC capacity in vivo, thereby providing an alternative to ex vivo manipulation that necessitates the removal of HSCs from their physiological environment.

The present invention demonstrates that in vivo administration of one or more Wnt/β-catenin signal-, Notch signal- or Hedgehog signal-promoting agents, e.g., GSK-3 inhibitor, increases repopulating function of transplanted wild-type mouse HSCs, and augments human neonatal and adult HSC capacity in vivo. In the present invention, the role of ATP-competitive GSK-3 inhibitors has been investigated in the regulation of mouse and human HSCs. The findings demonstrate that GSK-3 inhibitors augment HSC function in vivo and modulate Wnt, Hedgehog, and Notch targets specifically in HSCs, thereby providing a potent and unique approach to directly enhance HSC function in vivo.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Increasing hematopoietic stem cells in vivo in a mammalian subject" or "increasing hematopoietic stem cells in a mammalian subject" or "increasing the successful activity of progenitor/stem cells, or hematopoietic progenitor/stem cells in vivo in a mammalian subject" or "increasing successful activity of the HSC or progenitor/stem cell" refers to increasing an aspect of the life cycle of the progenitor/stem cell or the hematopoietic progenitor/stem cell (HSC), for example, as a result of a process, including but not limited to, cell proliferation, cell homing to the desired target tissue (e.g., transplanted HSCs are provided intravenously and become established in the bone marrow), decreased apoptosis, self renewal, or increased cell survival. An increase in hematopoietic progenitor/stem cells in vivo can be measured by a cellular assay as disclosed herein (e.g., in vivo hematopoietic stem cell repopulation assay, or hematopoeitic colony-forming unit (CFU) assay) or other cellular assay known in the art. Increased hematopoietic progenitor/stem cells in vivo in a mammalian subject or increased successful activity can be measured by comparing the fold increase in HSCs in a mammalian subject treated by administering one or more Wnt/β-catenin signal-, Notch signal- or Hedgehog signal-promoting agents to the mammalian subject compared to HSCs in a mammalian subject in the absence of such treatment, as measured by any of the cellular activity assays for HSCs or progenitor/stem cells discussed herein or known to one skilled in the art. The baseline number of HSCs in a mammalian subject is considered the the successful activity of HSCs in a mammalian subject in the absence of such treatment. The increase in HSCs in the treated mammalian subject by administering one or more Wnt/β-catenin signal-, Notch signal- or Hedgehog signal-promoting agents can be, for example, at least 1.5 fold, at least 2-fold, at least 4-fold, at least 8-fold, or at least 10-fold compared to HSCs in the mammalian subject before treatment.

"Increasing in vivo mesenchymal progenitor/stem cells or mesodermal progenitor/stem cells in a mammalian subject" or "increasing mesenchymal progenitor/stem cells or mesodermal progenitor/stem cells in a mammalian subject" or "increasing in vivo neural progenitor/stem cells in a mammalian subject" or "increasing neural progenitor/stem cells in a mammalian subject" or or "increasing the successful activity of mesenchymal progenitor/stem cells, mesodermal progenitor/stem cells or neural progenitor cells in vivo in a mammalian subject" refers to increasing an aspect of the life cycle of the mesenchymal progenitor/stem cells, mesodermal progenitor/stem cells, neural progenitor cells, muscle progenitor cells or stem cells, for example, as a result of a cellular process, including but not limited to, cell proliferation, cell homing to the desired target tissue (e.g., transplanted stem cells, muscle progenitor cells, or neural progenitor cells are provided intravenously and become established in the bone marrow, muscle, or nerve tissue), decreased apoptosis, self renewal, or increased cell survival. An increase in mesenchymal progenitor/stem cells, mesodermal progenitor/stem cells, neural progenitor cells, muscle progenitor cells or stem cells in vivo can be measured by a cellular assay as disclosed herein (e.g., in vivo hematopoietic stem cell repopulation assay, hematopoeitic colony-forming unit (CFU) assay, in vivo stem cell or progenitor cell repopulation assay, stem cell or progenitor cell colony-forming unit (CFU) assay or other cellular assay known in the art). Increased mesenchymal progenitor/stem cells, mesodermal progenitor/stem cells, neural progenitor cells, muscle progenitor cells or stem cells in vivo in a mammalian subject can be measured by comparing the fold increase in mesenchymal progenitor/stem cells, mesodermal progenitor/stem cells neural progenitor cells, muscle progenitor cells or stem cells in a mammalian subject treated by administering one or more Wnt/β-catenin signal-, Notch signal- or Hedgehog signal-promoting agents to the mammalian subject compared to the number of mesenchymal progenitor/stem cells, mesodermal progenitor/stem cells, neural progenitor cells, muscle progenitor cells or stem cells in a mammalian subject in the absence of such treatment. The increase in mesenchymal progenitor/stem cells, mesodermal progenitor/stem cells neural progenitor cells, muscle progenitor cells or stem cells in the mammalian subject treated by administering one or more Wnt/β-catenin signal-, Notch signal- or Hedgehog signal-promoting agents can be, for example, at least 1.5 fold, at least 2-fold, at least 4-fold, at least 8-fold, or at least 10 fold compared to progenitor/stem cells in the mammalian subject before treatment.

"Interacting one or more Wnt/β-catenin signal-, Notch signal- or Hedgehog signal-promoting agents with the hematopoietic stem cells in the mammalian subject" refers to either (1) direct contact between the agent and the cell or (2) an indirect interaction between the agent and the cell through an intermediary molecule or intermediary cell type. The interacting step can refer to directly contacting the hematopoietic progenitor/stem cell with the Wnt/β-catenin signal-, Notch signal- or Hedgehog signal-promoting agents to induce Wnt/β-catenin signaling, Notch signaling or Hedgehog signaling within the progenitor/stem cell, for example, through receptor/ligand interaction, intracellular signaling, transcriptional regulation of gene expression, cell-cell interaction or intercellular signaling.

Alternatively, the "interacting" step refers to an indirect interaction between a hematopoietic progenitor/stem cell and the Wnt/β-catenin signal-, Notch signal- or Hedgehog signal-promoting agents mediated through a third component, for example, through an intermediary signaling molecule, receptor, ligand, growth factor, or cell type, that affects, or is affected, by Wnt/β-catenin signaling, Notch signaling or Hedgehog signaling. For example, "interacting one or more Wnt/β-catenin signal-, Notch signal- or Hedgehog signal-promoting agents with the hematopoietic progenitor/stem cells in the mammalian subject" can occur by an indirect interaction between hematopoietic progenitor/stem cells, stem cells, muscle progenitor cells, neural progenitor cells, with the Wnt/β-catenin signal-, Notch signal- or Hedgehog signal-promoting agents. The indirect interaction can occur through intermediary signaling molecules for example, growth factors, ligands, receptors or through other cell types that transmit the intermediary signals. The intermediary signaling molecules, growth factors, transcription factors, ligands, or receptors that increase HSCs, mesenchymal progenitor/stem cells or mesodermal progenitor/stem cells neural progenitor/stem cells, muscle progenitor/stem cells or stem cells in vivo in a mammalian subject include, but are not limited to, Notch, Notch1, Jagged-1, Delta, Delta-1, Delta-4, Oct-3/4, Rex-1, Nanog, LIF-STAT2, STAT5, STAT5A, sonic hedgehog, bone morphogenetic proteins, cyclin-dependent kinase inhibitor, $p21^{Cip1/Waf1}$, HoxB4, or cytokines, e.g., SCF, Fit-3L, G-CSF, IL-3, IL-6 or IL-11. An indirect interaction between hematopoietic progenitor/stem cells and the Wnt/β-catenin signal-, Notch signal- or Hedgehog signal-promoting agents can occur by contacting hematopoietic progenitor/stem cells with a number of different growth factors or in a number of different cell types. The cell types include, but are not limited to, stromal cells in bone marrow, any cells in muscle, and all neural cells including glial cells and astrocytes.

"Wnt signal- or β-catenin signal-promoting agent" refers to an agonist of the Wnt signaling pathway, including but not limited to an agonist of one or more of Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16. "Wnt signal- or β-catenin signal-promoting agent" refers to one or more of the following polypeptides or a fragment thereof: a Dkk polypeptide, a crescent polypeptide, a cerberus polypeptide, an axin polypeptide, a Frzb polypeptide, a glycogen synthase kinase polypeptide, a T-cell factor polypeptide, or a dominant negative dishevelled polypeptide.

"Wnt/β-catenin signal-, Notch signal- or Hedgehog signal-promoting agent" further refers to agonists or antagonists of positive or negative signaling molecules, respectively, of the Wnt/β-catenin signaling, Notch signaling or Hedgehog signaling pathway. Signaling molecules of the Wnt signaling pathway include, but are not limited to, β-catenin, tumor suppressor gene product adenomatous polyposis coll (APC), axin, glycogen synthase kinase (GSK)-3β, TCF/LEF transcription factors, crescent, groucho, CBP, frizzled receptor, frizzled related proteins, LRP, LRP5, LRP6, kremin, Dvl/Dsh (disheveled), dickkopf, GSK-3 binding protein (GBP), FRAT/GBP, and any of the Wnt signaling pathway factors listed at http://www.stanford.edu/~rnusse/pathways/cell2.html.

"β-catenin signal-promoting agent" refers to agonists or antagonists of positive or negative signaling molecules, respectively, of β-catenin signaling, e.g., any agent that activates β-catenin signaling through inhibition of GSK-3 in the presence or absence of Wnt signaling. For example, activation of 13-catenin signaling in the absence of Wnt signaling can occur by activation of integrin linked kinase, activation of p53 leading to activation of Siah1, or activation of FGF signaling. "β-catenin signal-promoting agent" further refers to any signaling molecule that activates β-catenin target genes and is achieved by inhibition of GSK-3 that can have therapeutic potential. "β-catenin signal-promoting agent" further refers to any signaling molecule that activates β-catenin target genes independent of GSK-3 that can have therapeutic potential. Activation of β-catenin target genes without inhibiting GSK-3 can be achieved by inhibition (for example, by drug therapy, RNAi therapy or gene therapy) of any inhibitor of β-catenin function, including, but not limited to, APC, Axin, Chibby, ICAT, Groucho, CtBP.

"Wnt signal- or β-catenin signal-promoting agent" refers to one or more of the following: a nucleic acid comprising a nucleotide sequence that encodes a Wnt polypeptide, a polypeptide comprising an amino acid sequence of a Wnt polypeptide, a nucleic acid comprising a nucleotide sequence that encodes an activated Wnt receptor, a polypeptide comprising an amino acid sequence of an activated Wnt receptor, a small organic molecule that promotes Wnt/β-catenin signaling, Notch signaling or Hedgehog signaling, a small organic molecule that inhibits the expression or activity of a Wnt, β-catenin, Notch or Hedgehog antagonist, an antisense oligonucleotide that inhibits expression of a Wnt, β-catenin, Notch or Hedgehog antagonist, a ribozyme that inhibits expression of a Wnt, β-catenin, Notch or Hedgehog antagonist, an RNAi construct, siRNA, or shRNA that inhibits expression of a Wnt, β-catenin, Notch or Hedgehog antagonist, an antibody that binds to and inhibits the activity of a Wnt, β-catenin, Notch or Hedgehog antagonist, a nucleic acid comprising a nucleotide sequence that encodes a β-catenin polypeptide, a polypeptide comprising an amino acid sequence of a β-catenin polypeptide, a nucleic acid comprising a nucleotide sequence that encodes a Lef-1 polypeptide, a polypeptide comprising an amino acid sequence of a Lef-1 polypeptide.

"Wnt/β-catenin signal-, Notch signal- or Hedgehog signal-promoting agent" refers to one or more of the following: a nucleic acid comprising a nucleotide sequence that encodes a dominant negative GSK-3, GSK3α, or GSK3β polypeptide, a polypeptide comprising an amino acid sequence of a dominant negative GSK-3, GSK3α, or GSK3β polypeptide, a small organic molecule that binds to and inhibits the expression or activity of GSK-3, GSK3α, or GSK3β, an RNAi construct, siRNA, or shRNA that binds to and inhibits the expression and/or activity of GSK-3, GSK3α, or GSK3β, an antisense oligonucleotide that binds to and inhibits the expression of GSK-3, GSK3α, or GSK3β, an antibody that binds to and inhibits the expression and/or activity of GSK-3, GSK3α, or GSK3β, a ribozyme that binds to and inhibits the expression of GSK-3, GSK3α, or GSK3β, and any GSK-3-independent reagent that activates β-catenin target genes similar in effect to GSK-3 inhibition.

Exemplary Wnt/β-catenin signal-, Notch signal- or Hedgehog signal-promoting agents include, but are not limited to, LiCl or other GSK-3 inhibitors, as exemplified in U.S. Pat. Nos. 6,057,117 and 6,608,063; and U.S. applications 2004/0092535 and 2004/0209878; ATP-competitive, selective GSK-3 inhibitors CHIR-911 and CHIR-837 (also referred to as CT-99021 and CT-98023 respectively). Chiron Corporation (Emeryville, Calif.). These inhibitors were purified to >95% by high-performance liquid chromatography. CHIR-911 was formulated in 10% captisol solution for administration in vivo by intraperitoneal injection, with a half-maximal effective concentration [$EC_{50}$] of 766 nM and >10,000 fold selectivity for GSK-3. Ring et al., *Diabetes* 52: 588-595, 2003. CHIR-837 was formulated in DMSO for in vitro use, with an $EC_{50}$ of 375 nM and >5,000 fold selectivity for GSK-3 Cline et al., *Diabetes* 51: 2903-2910, 2002 each incorporated herein by reference in their entirety.

"Hedgehog compound" refers to a class of molecules of the hedgehog family that includes recombinant hedgehog protein, analogs, and derivatives of hedgehog proteins, and agonists and antagonists of hedgehog protein receptors and functional equivalents of the aforementioned. See, for example, PCT International Applications WO 95/18856 and WO 96/17924, each incorporated herein by reference in their entirety.

"Hedgehog agonist" refers to an agent which potentiates or recapitulates the bioactivity of hedgehog, such as to activate transcription of target genes. Preferred hedgehog agonists can be used to overcome a ptc gain-of-function and/or a smoothened loss-of-function, the latter also being referred to as smoothened agonists. "Hedgehog agonist" refers not only to any agent that may act by directly activating the normal function of the hedgehog protein, but also to any agent that activates the hedgehog signaling pathway, and thus inhibits the function of ptc.

Further hedgehog agonist proteins include, but are not limited to, TGF-β proteins, e.g., TGF-β1, bone morphogenic protein (BMP), e.g., BMP-4; tumor necrosis factor, (TNF) proteins, e.g., TNF-α; wnt family; and hedgehog proteins. Compounds may also include naturally occurring and synthetic agonists, antagonists, analogs and derivatives of the above. These molecules may interact with membrane proteins which initiate signal transduction pathways of Wnt, Hedgehog or Notch resulting in a biological response. Therefore, in addition to the above compounds, agonists and antagonists to these membrane binding proteins including those receptors, receptor agonists and receptor antagonists associated with hedgehog binding receptors and hedgehog signalling transduction pathways such as smoothened, patched and gli may have utility in regulating hematopoiesis and vascular growth.

Methods for treating disease in a mammalian subject or methods for increasing hematopoietic stem cells in vivo in a mammalian subject are provided by administering a therapeutic composition, for example, a polypeptide, nucleic acid, small molecule, antisense oligonucleotide, ribozyme, RNAi construct, siRNA, shRNA, or antibody, to the mammalian subject. For example, the therapeutic composition can be one or more small molecule modulators of Hedgehog signaling. The therapeutic composition can be a GSK-3 inhibitor. Furthermore, therapeutic efficacy of the Hedgehog pathway antagonist, cyclopamine, has been studied in preclinical models of medulloblastoma, a common malignant brain tumor in children. Berman et al., *Science* 297: 1559-1561, 2002. Therapeutic efficacy of the Hedgehog pathway agonists have been studied for treatment of traumatic and chronic degenerative conditions. Hedgehog pathway agonists have been shown to target the protein Smoothened. Both antagonists and agonists of the Hedgehog pathway have been shown to target the protein Smoothened. Therapeutic efficacy of a Hedgehog pathway agonist, SAG, a chlorobenzothiophene-containing Hedgehog pathway agonist, binds to Smoothened protein in a manner that antagonizes cylcopamine action. King, *Journal of Biology* 1:8, 2002; Stecca et al., *Journal of Biology* 1:9, 2002; Frank-Kamenetsky, et al., *Journal of Biology* 1:10, 2002; Chen et al., *Proc. Natl. Acad. Sci USA* 99: 14071-14076, 2002, each incorporated herein by reference in their entirety.

The present invention is directed to methods for increasing non-terminally differentiated cells in vivo, e.g., progenitor cells or stem cells, by activating the Wnt/β-catenin signaling, Notch signaling or Hedgehog signaling pathway in a progenitor/stem cell such that the differentiation of the progenitor/stem cell is inhibited without destroying the ability of the cell to proliferate. "precursor cells" or "progenitor/stem cell" shall mean any non-terminally differentiated cells. The present invention is also directed to methods for increasing non-terminally differentiated cells in vivo, e.g., progenitor cells or stem cells, by activating the Wnt/β-catenin signaling, Notch signaling or Hedgehog signaling pathway in the cells such that the differentiation of the progenitor/stem cell is inhibited without affecting the mitotic activity of the cells. Further, the progenitor/stem cells can be isolated from a cell population, if desired, before or after Wnt/β-catenin signaling, Notch signaling or Hedgehog signaling pathway activation.

Activation of Notch pathway is preferably achieved by contacting the cell with a Notch ligand, e.g., in soluble form or recombinantly expressed on a cell surface or immobilized on a solid surface, or by introducing into the cell a recombinant nucleic acid expressing a dominant active Notch mutant or an activating Notch ligand, or other molecule that activates the Notch pathway. Agonists of the Notch pathway are able to activate the Notch pathway at the level of protein-protein interaction or protein-DNA interaction. Agonists of Notch include but are not limited to proteins comprising the portions of toporythmic proteins such as Delta or Serrate or Jagged (Lindsell et al., *Cell* 80: 909-917, 1995) that mediate binding to Notch, and nucleic acids encoding the foregoing (which can be administered to express their encoded products in vivo) and proteins, nucleic acids, small molecules, or derivatives thereof that regulate activity or gene expression of these proteins. In a further embodiment, the agonist is a protein or derivative or fragment thereof comprising a functionally active fragment such as a fragment of a Notch ligand that mediates binding to a Notch protein. In another embodiment, the agonist is a human protein or portion thereof (e.g., human Delta). In another embodiment the agonist is Deltex or Suppressor of Hairless or a nucleic acid encoding the foregoing (which can be administered to express its encoded product in vivo).

The Notch pathway is a signal transducing pathway comprising elements which interact, genetically and/or molecularly, with the Notch receptor protein. For example, elements which interact with the Notch protein on both a molecular and genetic basis are, for example, and not by way of limitation, Delta, Serrate and Deltex. Elements which interact with the Notch protein genetically are, for example, and not by way of limitation, Mastermind, Hairless and Suppressor of Hairless.

"Adult" refers to tissues and cells derived from or within an animal subject at any time after birth. "Embryonic" refers to tissues and cells derived from or within an animal subject at any time prior to birth.

"Blood development" refers to hematopoiesis and vascular growth. "Vascular growth" refers to at least one of vasculogenesis and angiogenesis and includes formation of capillaries, arteries, veins or lymphatic vessels.

"Hematopoiesis" refers to the process of production of progenitor/stem cells from which many cell types are derived. "Hematopoietic stem cell" refers to a multipotential precursor from which all classes of blood cell are derived; in addition, mesenchymal progenitor/stem cells, mesodermal progenitor/stem cells, endothelial progenitor/stem cells, and ectodermal or neural progenitor/stem cells can be derived from hematopoietic stem cell. "Definitive blood cells" refers to blood cells of the fetal or adult organism. "Primitive blood cells" refers to a transient population of blood cells forming during blood development in the embryo.

"Progenitor cells" or "stem cells" refers to undifferentiated cells that are more restricted in their potential to give rise to differentiated cell types compared with a stem cell. The progenitor cell or stem cell includes, but is not limited to, hematopoietic progenitor/stem cell, mesenchymal progenitor/stem cells, mesodermal progenitor/stem cells, epithelial progenitor/stem cell, kidney progenitor/stem cell, neural progenitor/stem cell, skin progenitor/stem cell, osteoblast progenitor/stem cell, chondrocyte progenitor/stem cell, liver progenitor/stem cell, or muscle progenitor/stem cell.

"Committed" refers to cells destined to differentiate along a specific lineage instead of retaining multipotency.

"Synergistic effect" refers to two or more compounds where little or no biological effect is observed with the compounds alone but together the compounds have a potent biological effect.

Human hematopoietic progenitor/stem cells (HSCs) have been identified in bone marrow (BM), peripheral blood and umbilical cord blood (CB). The functional capacity of the cells derived from these tissues can differentiate to a hematopoietic cell fate. In addition, marrow-derived stromal cells were found to differentiate along the osteogenic lineage. Further studies indicated that multipotent mesenchymal progenitor/stem cells (MSCs) reside within the BM, and were capable of giving rise to adipose, bone, cartilage, skeletal muscle and endothelial cell lineages. These combined findings have led to the current notion that BM is therefore a source of both MSCs as well as HSCs. Similar to BM, human HSCs can also be found in umbilical CB and peripheral blood, however, studies aimed at isolating mesenchymal stem/progenitor cells from these alternative hematopoietic sources have provided mixed results. Cells from pre-term CB displayed mesenchymal properties while more recent studies reported a lack of MSCs from full term CB. Similarly, reports have demonstrated the presence or absence of mesenchymal precursors from peripheral blood. Jay et al. *Cell Research* 14: 268-282, 2004, incorporated herein by reference in its entirety.

Human umbilical cord blood (CB) contains a combination of primitive cells and mature cells that have committed to the various hematopoietic lineages. Studies have focused on the characterization and clinical utility of progenitor/stem cells from CB partly due to the ease of obtaining this abundant cell source and the decreased immunogenicity of these cells upon allogenic transplantation. For hematopoietic cell fate, progenitors capable of multi-lineage hematopoiesis reside among cellular subsets of uncommitted CB cells that do not express specific hematopoietic lineage markers. These mature CB cells can be removed based on the surface expression of proteins associated with various hematopoietic lineages to derive a remaining subset of primitive cells referred to as the lineage depleted (Lin$^-$) fraction. Candidate human HSCs have been shown to exclusively reside in the Lin$^-$ fraction and can be further enriched to Lin$^-$ subsets expressing CD34 but devoid of CD38 (Lin$^-$CD34$^+$CD38$^-$). Subsequent studies identified additional subpopulations of Lin$^-$ cells possessing hematopoietic progenitor function that was devoid of both CD34 and CD38 (Lin$^-$CD34$^-$CD38$^-$), indicating that CD34 may not be unique to the human HSC phenotype. This series of studies illustrates the heterogeneity of the Lin-CD34$^-$ population in human CB and suggests that additional subpopulations may remain to be identified within the Lin-population.

A population of cells in human CB devoid of the hematopoietic cell fate marker, CD45 has been identified. Functional analysis of the Lin–CD45–CD34– cells revealed that similar to CD45$^-$CD34$^-$ cells from BM, these cells possess chondrocytic differentiation potential and hence share properties of mesenchymal progenitors. However, unlike BM-derived mesenchymal progenitor/stem cells, CB derived Lin$^-$CD45$^-$CD34$^-$ cells possess unique de novo multi-lineage hematopoietic progenitor capacity. The functional potential displayed by this novel population suggests that Lin$^-$CD45$^-$CD34$^-$ cells derived from human CB are potential therapeutic targets for cellular therapies for osteogenic as well as hematopoietic deficiencies and represent a population of human cells with unique developmental potential. Jay et al. *Cell Research* 14: 268-282, 2004, incorporated herein by reference in its entirety.

Embryonic stem cells (ESCs), for example, mammalian or human embryonic stem cells (hESCs), can be used to derive progenitor/stem cells including but not limited to, hematopoietic progenitor/stem cell, mesenchymal progenitor/stem cell, mesodermal progenitor/stem cell, endothelial progenitor/stem cell, or ectodermal or neural progenitor/stem cell. A subpopulation of primitive endothelial-like cells have been identified that are derived from human embryonic stem cells (hESCs) that express PECAM-1, Flk-1, and VE-cadherin, but not CD45 (CD45negPFV cells), and that are uniquely responsible for endothelial and hematopoietic development. Human hematopoiesis and endothelial maturation can originate from a subset of embryonic endothelial cells that possesses hemangioblastic properties.

Therapeutic targets of corrective progenitor/stem cell gene therapy include, but are not limited to, allogeneic or autologous hematopoietic progenitor/stem cell transplantation for treatment of chronic myeloid leukemia, acute myeloid leukemia, non-Hodgkin's lymphoma, multiple myeloma, chronic lymphocytic leukemia, Hodgkin's disease, myelodysplastic syndrome.

A method of treating an immune related disease is provided wherein the disease is an immunodeficiency disease, for example, primary immunodeficiency, such as ADA-deficient SCID, X-linked SCID, common variable immunodeficiency, chronic granulomatous disease (CGD), X-linked agammaglobulinemia, Wiskott-Aldrich syndrome; hemoglobinopathy, such as sickle cell anemia, β-thalassemia; other single-gene disorders, such as Hurler's disease, Gaucher's disease, hemophilia A, hemophilia B, α-1 antitrypsin deficiency; or stem cell defects, such as Fanconi anemia.

A method of treating a disease or conditions using methods of the present invention, include but are not limited to the following disease states. The gene and genetic perturbation are provided in parentheses. Schizophrenia (WNT1 Elevated); Tetra-amelia (WNT3 LOF); Intersex (WNT4 GOF); Kidney damage (WNT4 Elevated); Polycystic kidney disease (WNT4 Variable); Leukaemia (WNT5αLOF; reduced); Metastasis (WNT5αElevated); Osteoarthritis (sFRP3 SNP; reduced); FEVR (FZ4 LOF); Familial exudative vitreoretinopathy (LRP5, low bone mass LOF); High bone mass (LRP5 GOF); Lung cancer (DSHIDVL Elevated); Cancer (APC LOF); Cancer (AXIN LOF); Cancer (AXIN2, tooth agenesis LOF); Cancer (β-catenin GOF); Aggressive fibromatosis (β-catenin Elevated); Pulmonary fibrosis (β-catenin Elevated); Alzheimer's disease; Cardiovascular disease (Abbreviations: APC, adenomatous polyposis coli; DSHIDVL, Dishevelled; FZ, Frizzled; GOF, gain of function; LOF, loss of function; LRP, LDL-receptor-related protein; sFRP, secreted Frizzled-related protein.) Moon et al., *Nature Reviews Genetics* 5: 689-699, 2004, incorporated by reference in its entirety.

Inhibitors of WNT/β-catenin signalling can be used for treatment of cancers. WNT/β-catenin signalling seems to be involved in cancer progression, and not just initiation. Kim, et al., *Mol. Cancer Ther.* 1: 1355-1359, 2002; Gunther, et al., *Genes Dev.* 17: 488-501, 2003; Derksen, et al. *Proc. Natl Acad. Sci. USA* 101: 6122-6127, 2004. Approaches to cancer treatment include, but are not limited to, small-molecule inhibitors that block interaction of β-catenin with TCF86 or CREB binding protein (CBP) (Emami, K. H. et al. *Proc. Natl Acad. Sci. USA,* 2004), siRNAs (Giles, et al., *Biochim. Biophys. Acta,* 1653: 1-24, 2003) and the therapeutic use of antibodies against WNTs. He, et al. *Neoplasia* 6, 7-14 (2004); You, et al., *Oncogene* 21 Jun. 2004 [epub ahead of print], each incorporated by reference in their entirety.

Other potential therapeutic inhibitors of β-catenin signalling include agents that have no obvious link to the β-catenin pathway, such as extracellular calcium, non-steroidal anti-inflammatory drugs, including exisulind, sulindac and aspirin, and the tyrosine kinase inhibitor ST1571/Gleevac96. Conversely, activators of β-catenin signalling will probably be useful in treating osteoporosis and Alzheimer's disease, and might include activators of LRP5 as well as inhibitors of GSK3. Moon et al., *Nature Reviews Genetics* 5: 689-699, 2004, each incorporated by reference in their entirety.

A method of treating a degenerative muscle disease is provided wherein the disease is a muscular dystrophy or myopathy. Muscular dystrophy (MD) refers to a group of genetic diseases characterized by progressive weakness and degeneration of the skeletal muscles which control movement. There are many forms of muscular dystrophy, some noticeable at birth (congenital muscular dystrophy), others in adolescence (Becker MD). The 3 most common types are Duchenne, facioscapulohumeral, and myotonic. These three types differ in terms of pattern of inheritance, age of onset, rate of progression, and distribution of weakness. Duchenne muscular dystrophy primarily affects boys and is the result of mutations in the gene that regulates dystrophin—a protein involved in maintaining the integrity of muscle fiber. Onset is between 3-5 years and progresses rapidly. Facioscapulohumeral muscular dystrophy appears in adolescence and causes progressive weakness in facial muscles and certain muscles in the arms and legs. It progresses slowly and can vary in symptoms from mild to disabling. Myotonic muscular dystrophy varies in the age of onset and is characterized by myotonia (prolonged muscle spasm) in the fingers and facial muscles; a floppy-footed, high-stepping gait; cataracts; cardiac abnormalities; and endocrine disturbances.

"Myopathy" refers to neuromuscular disorders in which the primary symptom is muscle weakness due to dysfunction of muscle fiber. Other symptoms of myopathy can include include muscle cramps, stiffness, and spasm. Myopathies can be inherited (such as the muscular dystrophies) or acquired (such as common muscle cramps). Congenital myopathy is characterized by developmental delays in motor skills; skeletal and facial abnormalities are occasionally evident at birth. Muscular dystrophy is characterized by progressive weakness in voluntary muscles; sometimes evident at birth. Mitochondrial myopathy is caused by genetic abnormalities in mitochondria, cellular structures that control energy; include Kearns-Sayre syndrome, MELAS and MERRF. Glycogen storage diseases of muscle is caused by mutations in genes controlling enzymes that metabolize glycogen and glucose (blood sugar); include Pompe's, Andersen's and Cori's diseases. Myoglobinuria is caused by disorders in the metabolism of a fuel (myoglobin) necessary for muscle work; include McArdle, Tarui, and DiMauro diseases. Dermatomyositis is an inflammatory myopathy of skin and muscle. Myositis ossificans is characterized by bone growing in muscle tissue. Familial periodic paralysis is characterized by episodes of weakness in the arms and legs. Polymyositis, inclusion body myositis, and related myopathies are inflammatory myopathies of skeletal muscle. Neuromyotonia is characterized by alternating episodes of twitching and stiffness, and stiff-man syndrome is characterized by episodes of rigidity and reflex spasms. Common muscle cramps and stiffness, and tetany is characterized by prolonged spasms of the arms and legs Cardiomyopathy refers to a disease of the myocardium associated with ventricular dysfunction as defined by the World Health Organization. Dilated cardiomyopathy is characterized by dilatation and impaired contractility of the left (or right) ventricle. Presentation is usually with heart failure. Arrhythmia, thromboembolism, and sudden death are common. Hypertrophic cardiomyopathy is characterized by left (or right) ventricular hypertrophy, which is usually asymmetric and involves the interventricular septum. Typically, left ventricular volume is reduced. Systolic gradients are sometimes present. Typical presentations include dyspnea, arrhythmia, and sudden death. Restrictive cardiomyopathy is characterized by restrictive filling of the left (or right) ventricle with normal or near normal ventricular contractility and wall thickness. Presentations are usually with heart failure. The cardiomyopathies are not the only causes of the heart failure syndrome. In western countries, coronary artery disease with resultant ischemic cardiomyopathy remains the primary cause of the heart failure syndrome.

A method of treating a neurodegenerative disease is provided wherein the disease is a central nervous system disorder or peripheral nervous system disorder. Central nervous system disorders encompass numerous afflictions such as neurodegenerative diseases (e.g., Alzheimer's disease and Parkinson's disease), acute brain injury (e.g., stroke, head injury, cerebral palsy) and a large number of CNS dysfunctions (e.g., depression, epilepsy, and schizophrenia). These diseases, which include Alzheimer's disease, multiple sclerosis (MS), Huntington's disease, amyotrophic lateral sclerosis, and Parkinson's disease, have been linked to the degeneration of neural cells in particular locations of the CNS, leading to the inability of these cells or the brain region to carry out their intended function.

"Activators," "inhibitors," and "modulators" of Wnt/β-catenin signaling, Notch signaling or Hedgehog signaling are used to refer to activating, or modulating molecules, respectively, identified using in vitro and in vivo assays for Wnt/β-catenin signal-, Notch signal- or Hedgehog signal-promoting agents, e.g., ligands, agonists, antagonists, and their homologs and mimetics. "Modulator" includes inhibitors and activators. Inhibitors are agents that, e.g., bind to, partially or totally block stimulation, decrease, prevent, delay activation, inactivate, desensitize, or down regulate the activity of Wnt/β-catenin signaling, Notch signaling or Hedgehog signaling, e.g., antagonists. Activators are agents that, e.g., bind to, stimulate, increase, open, activate, facilitate, enhance activation, sensitize or up regulate the activity of Wnt/β-catenin signaling, Notch signaling or Hedgehog signaling, e.g., agonists. Modulators include agents that, e.g., alter the interaction of Wnt, β-catenin, Notch, or Hedgehog with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring Wnt, β-catenin, Notch, or Hedgehog ligands, e.g., Wnt, β-catenin, Notch, or Hedgehog polypeptides with altered activity, as well as naturally occurring and synthetic ligands, antagonists, agonists, small chemical molecules and the like. Such assays for inhibitors and activators include, e.g., applying putative modulator compounds to a cell expressing Wnt, β-catenin, Notch, or Hedgehog and then determining the functional effects on Wnt/β-catenin signaling, Notch signaling or Hedgehog signaling, as described herein. Samples or assays comprising Wnt/β-catenin signaling, Notch signaling or Hedgehog signaling that are treated with a potential activator, inhibitor, or modulator are compared to control samples without the inhibitor, activator, or modulator to examine the extent of inhibition. Control samples (untreated with activators, inhibitors, or modulators) can be assigned a relative Wnt, β-catenin, Notch, or Hedgehog activity value of 100%. Inhibition of Wnt/β-catenin signaling, Notch signaling or Hedgehog signaling is achieved when the Wnt, β-catenin, Notch, or Hedgehog activity value relative to the control is about 80%, optionally 50% or 25-0%. Activation of Wnt/β-catenin signaling, Notch signaling or Hedgehog signaling is achieved when the Wnt, β-catenin, Notch, or Hedgehog activity value relative to the control is 110%, optionally 150%, optionally 200-500%, or 1000-3000% higher. Activation of Wnt/β-catenin signaling, Notch signaling or Hedgehog signaling can be measured in a cellular assay for increasing hematopoietic progenitor/stem cells in vivo in a mammalian subject or increasing mesenchymal progenitor/stem cells, mesodermal progenitor/stem cells, neural progenitor/stem cells, muscle progenitor/stem cells or stem cells in vivo in a mammalian subject, as described herein.

"Agonist" is used in the broadest sense and includes any molecule that mimics or enhances a biological activity of Wnt, β-catenin, Notch, or Hedgehog polypeptides, or Wnt/β-catenin signaling, Notch signaling or Hedgehog signaling. Suitable agonist molecules specifically include agonist antibodies or antibody fragments, fragments or amino acid sequence variants of native Wnt, β-catenin, Notch, or Hedgehog polypeptides, peptides, antisense oligonucleotides, small organic molecules, and the like. Methods for identifying agonists of Wnt, β-catenin, Notch, or Hedgehog polypeptides can comprise contacting a Wnt, β-catenin, Notch, or Hedgehog polypeptide with a candidate agonist molecule and measuring a detectable change in one or more biological activities normally associated with the Wnt/β-catenin signaling, Notch signaling or Hedgehog signaling, e.g., Wnt binding to the Frizzled receptor, or intracellular accumulation of β-catenin.

"Antagonist" is used in the broadest sense, and includes any molecule that partially or fully blocks, inhibits, or neutralizes an inhibitor of a biological activity of a Wnt, β-catenin, Notch, or Hedgehog polypeptide, or Wnt/β-catenin signaling, Notch signaling or Hedgehog signaling. Suitable antagonist molecules specifically include antagonist antibodies or antibody fragments, fragments or amino acid sequence variants of native polypeptides, peptides, antisense oligonucleotides, small organic molecules, and the like. Methods for identifying antagonists of an inhibitor of a biological activity of a Wnt, β-catenin, Notch, or Hedgehog polypeptide, or of Wnt- or β-catenin-signaling can comprise contacting Wnt, β-catenin, Notch, or Hedgehog polypeptides, or Wnt- or β-catenin-signaling polypeptides with a candidate antagonist molecule and measuring a detectable change in one or more biological activities normally associated with Wnt/β-catenin signaling, Notch signaling or Hedgehog signaling.

"Signaling in cells" refers to the interaction of a ligand, such as an endogenous or exogenous ligand, e.g., Notch signal-promoting or Hedgehog signal-promoting, or Wnt signal-promoting or β-catenin signal-promoting agents, with receptors, such as Frizzled receptor, resulting in cell signaling to produce a response, for example, increasing expression of β-catenin target genes resulting in increased hematopoietic progenitor/stem cells in vivo in a mammalian subject.

"Endogenous" refers a protein, nucleic acid, lipid or other component produced within the body or within cells or organs of the body of a mammalian subject or originating within cells or organs of the body of a mammalian subject.

"Exogenous" refers a protein, nucleic acid, lipid, or other component originating outside the body of a mammalian subject.

"Test compound" refers to a nucleic acid, DNA, RNA, protein, polypeptide, or small chemical entity that is determined to effect an increase or decrease in a gene expression as a result of signaling through the Wnt/β-catenin signaling, Notch signaling or Hedgehog signaling pathways. The test compound can be an antisense RNA, ribozyme, polypeptide, or small molecular chemical entity. "Test compound" can be any small chemical compound, or a biological entity, such as a protein, sugar, nucleic acid or lipid. Typically, test compounds will be small chemical molecules and polypeptides. A "test compound specific for Wnt/β-catenin signaling, Notch signaling or Hedgehog signaling" is determined to be a modulator of Notch signaling or Hedgehog signaling or Wnt signaling or β-catenin signaling, for example, resulting in Wnt binding to the Frizzled receptor, or intracellular accumulation of β-catenin.

"Cell-based assays" include Wnt/β-catenin signaling, Notch signaling or Hedgehog signaling assays, for example, radioligand or fluorescent ligand binding assays for Wnt, β-catenin, Notch, or Hedgehog to cells, plasma membranes, detergent-solubilized plasma membrane proteins, immobilized collagen (Alberdi, *J Biol Chem.* 274:31605-12, 1999; Meyer et al., 2002); Wnt, β-catenin, Notch, or Hedgehog-affinity column chromatography (Alberdi, *J Biol Chem.* 274: 31605-12, 1999; Aymerich et al., *Invest Ophthalmol Vis Sci.* 42:3287-93, 2001); Wnt, β-catenin, Notch, or Hedgehog blot using a radio- or fluorosceinated-ligand (Aymerich et al., *Invest Ophthalmol Vis Sci.* 42:3287-93, 2001; Meyer et al., 2002); Size-exclusion ultrafiltration (Alberdi et al., 1998, *Biochem.*; Meyer et al., 2002); or ELISA. Cellular assay to measure increasing hematopoietic progenitor/stem cells in vivo in a mammalian subject or increasing neural progenitor cells, muscle progenitor cells or stem cells in vivo in a mammalian subject, as described herein, include, but are not limited to, in vivo HSC repopulation assay or hematopoeitic colony-forming unit (CFU) assays. Multilineage donor HSC reconstitution was examined by flow cytometry for surface markers representing primitive (c-Kit+Sca-1+), myeloid (CD45+CD11b+), erythroid (CD45−Ter119+), B cell (CD45+B220+), and T cell (CD45+CD3+) lineages indicating multilineage donor HSC reconstitution. Exemplary Wnt/β-catenin signaling, Notch signaling or Hedgehog signaling activity assays of the present invention are: Assays for Wnt-regulated target gene Axin2 quantified by real-time PCR; Yan et al., *Proc Natl Acad Sci USA* 98:14973-8, 2001; Jho et al., *Mol Cell Biol* 22:1172-83, 2002. Wnt-regulated target gene CyclinD1 quantified by real-time PCR; Issack and Ziff, *Cell Growth Differ* 9:837-45, 1998. Notch regulated target gene, Hes1, quantified by real-time PCR; Jarriault et al., *Nature* 377:355-8, 1995. Hedgehog regulated target genes, Gli3 and Patched1 (Ptc1), quantified by real-time PCR. Marigo et al., 180 1:1996; Marigo and Tabin, *Proc Natl Acad Sci USA* 93:9346-9351, 1996, each incorporated by reference in their entirety. Further cell based assays include but are not limited to, luciferase, green fluorescent protein (GFP), or β-galactosidase reporter screens for β-catenin responsive genes, for example using TOPFLASH reporter. See, for example, Veeman M. et al., Current Biology, 13: 680-685, 2003; Veeman M. et al., *Dev Cell.* 5: 367-377, 2003, each incorporated by reference in their entirety.

In one aspect, a method of screening drug candidates for Wnt/β-catenin signal-, Notch signal- or Hedgehog signal-promoting agents is provided and comprise, for example, a β-catenin-responsive gene reporter assay in which a reporter DNA construct consists of TCF or LEF binding sites upstream of a minimal promoter, and drives expression of luciferase, GFP, or β-galactosidase. Luciferase, GFP, or β-galactosidase is used as a surrogate to demonstrate increased activity of β-catenin signaling, as measured by the reporter protein fluorescence or enzymatic means. Further methods of screening drug candidates for Wnt signal- or β-catenin signal-promoting agents involve an assay to measure Wnt binding to the Frizzled receptor, or intracellular accumulation of β-catenin. Wnt binding to the Frizzled receptor or intracellular accumulation of β-catenin can be assayed by either immobilizing the ligand or the receptor. For example, the assay can include immobilizing Frizzled receptor fused to a His tag onto Ni-activated NTA resin beads. Wnt can be added in an appropriate buffer and the beads incubated for a period of time at a given temperature. After washes to remove unbound material, the bound protein can be released with, for example, SDS, buffers with a high pH, and the like and analyzed. For example, the Wnt signal- or β-catenin signal-promoting agent promotes Wnt binding to the Frizzled receptor or intracellular accumulation of β-catenin.

"Interacting" refers to mixing a test compound, e.g., one or more Wnt/β-catenin signal-, Notch signal- or Hedgehog signal-promoting agents, in a soluble form into an assay system, for example, a cell-based assay system, such that an effect upon receptor-mediated signaling or intracellular signaling can be measured. For example, the "interacting" step can occur directly by contacting the hematopoietic progenitor/stem cell, stem cell, muscle progenitor cell, or neural progenitor cell and the one or more Wnt/β-catenin signal-, Notch signal- or Hedgehog signal-promoting agents to induce Wnt/β-catenin signaling, Notch signaling or Hedgehog signaling within the stem cell or progenitor cell. Alternatively, the "interacting" step can occur indirectly between a hematopoietic progenitor/stem cell, stem cell, muscle progenitor cell, or neural progenitor cell and the Wnt/β-catenin signal-, Notch signal- or Hedgehog signal-promoting agents, for example, through an intermediary signaling molecule, receptor, ligand, growth factor, or cell type, that affects, or is affected by, Wnt/β-catenin signaling, Notch signaling or Hedgehog signaling.

"Signaling responsiveness" or "effective to activate signaling" or "stimulating a cell-based assay system" refers to the ability of Wnt/β-catenin signal-, Notch signal- or Hedgehog signal-promoting agent to enhance an immune response, to increase hematopoietic progenitor/stem cells, stem cells, mesenchymal progenitor/stem cells, mesodermal progenitor/stem cells muscle progenitor cells, or neural progenitor cells in vivo in a mammalian subject, or treating an immune related disease or a degenerative muscle disease or neurodegenerative disease in a mammalian subject.

"Detecting an effect" refers to an effect measured in a cell-based assay system. For example, the effect detected can be Wnt/β-catenin signaling, Notch signaling or Hedgehog signaling in an assay system, for example, Wnt, β-catenin, Notch, or Hedgehog cellular assay, Frizzled receptor binding assay, Axin2 assay, or CyclinD1 assay, or β-catenin-responsive gene reporter assay. See, for example, Veeman M. et al., *Current Biology,* 13: 680-685, 2003; Veeman M. et al., *Dev Cell.* 5: 367-377, 2003, each incorporated by reference in their entirety.

"Assay being indicative of modulation" refers to results of a cell-based assay system indicating that cell activation by Wnt/β-catenin signal-, Notch signal- or Hedgehog signal-promoting agents are indicated to treat an immune related disease in a mammalian subject by increasing hematopoietic progenitor/stem cells, stem cells, muscle progenitor cells, or neural progenitor cells in vivo in a mammalian subject or treating a degenerative muscle disease or neurodegenerative disease in a mammalian subject by increasing progenitor/stem cells, muscle progenitor cells, or neural progenitor cells.

"Biological activity" and "biologically active" with regard to Wnt/β-catenin signal-, Notch signal- or Hedgehog signal-promoting agents of the present invention refer to the ability of the ligand molecule to specifically bind to and signal through a native or recombinant Wnt, β-catenin, Notch, or Hedgehog, or to block the ability of an inhibitor of native or recombinant Wnt, β-catenin, Notch, or Hedgehog polypeptides to participate in signal transduction. Thus, the (native and variant) Wnt/β-catenin signal-, Notch signal- or Hedgehog signal-promoting agents of the present invention include agonists of a native or recombinant Wnt, β-catenin, Notch, or Hedgehog polypeptides and receptors or ligands thereof. Preferred biological activities of the Wnt/β-catenin signal-, Notch signal- or Hedgehog signal-promoting agents of the present invention include the ability to induce or inhibit, for example, enhancing an immune response, or increasing hematopoietic progenitor/stem cells, stem cells, muscle progenitor cells, or neural progenitor cells in vivo in a mammalian subject or treating a degenerative muscle disease or neurodegenerative disease in a mammalian subject. Accordingly, the administration of the compounds or agents of the present invention can prevent or delay, to alleviate, or to arrest or inhibit development of the symptoms or conditions associated with immune related disease, a degenerative muscle disease or neurodegenerative disease in a mammalian subject.

"Signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., an immune response described above.

"High affinity" for a ligand refers to an equilibrium association constant (Ka) of at least about $10^3 M^{-1}$, at least about $10^4 M^{-1}$, at least about $10^5 M^{-1}$, at least about $10^6 M^{-1}$, at least about $10^7 M^{-1}$, at least about $10^8 M^{-1}$, at least about $10^9 M^{-1}$, at least about $10^{10} M^{-1}$, at least about $10^{11} M^{-1}$, or at least about $10^{12} M^{-1}$ or greater, e.g., up to $10^{13} M^{-1}$ or $10^{14} M^{-1}$ or greater. However, "high affinity" binding can vary for other ligands.

"$K_a$", as used herein, is intended to refer to the equilibrium association constant of a particular ligand-receptor interaction, e.g., antibody-antigen interaction. This constant has units of 1/M.

"$K_d$", as used herein, is intended to refer to the equilibrium dissociation constant of a particular ligand-receptor interaction. This constant has units of M.

"$k_a$", as used herein, is intended to refer to the kinetic association constant of a particular ligand-receptor interaction. This constant has units of 1/Ms.

"$k_d$", as used herein, is intended to refer to the kinetic dissociation constant of a particular ligand-receptor interaction. This constant has units of 1/s.

"Particular ligand-receptor interactions" refers to the experimental conditions under which the equilibrium and kinetic constants are measured.

"Isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$)

The ability of a molecule to bind to Wnt, β-catenin, Notch, or Hedgehog can be determined, for example, by the ability of the putative ligand to modulate Wnt binding to the Frizzled receptor, by measuring intracellular accumulation of β-catenin, Axin2 assay, or CyclinD1 assay. Specificity of binding can be determined by comparing binding in the presence or absence of the putative ligand.

"Control sequences" or "regulatory sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

"Sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

"Cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny cannot be precisely identical in DNA content, due to deliberate or inadvertent mutations. Mutant progeny that have the same function or biological activity as screened for in the originally transformed cell are included. Where distinct designations are intended, it will be clear from the context.

"Receptor" denotes a cell-associated protein, for example Frizzled receptor, that binds to a bioactive molecule termed a "ligand." This interaction mediates the effect of the ligand on the cell. Receptors can be membrane bound, cytosolic or nuclear; monomeric (e.g., Frizzled receptor, thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors, for example Frizzled receptor, are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

"Treatment" or "treating" refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination. Accordingly, "treatment" or "treating" includes the administration of the compounds or agents of the present invention to inhibit or enhance an immune response, or treat immune related disease, diabetes, graft vs. host disease, immunodeficiency disease, hematopoietic malignancy, hematopoietic failure, hematopoietic progenitor/stem cell transplantation, or a muscle degenerative disease. It also includes the administration of the compounds of the present invention to enhance an immune response in a subject toward infection with a pathogen. Accordingly, "treatment" or "treating" includes the administration of the compounds or agents of the present invention to prevent or delay, to alleviate, or to arrest or inhibit development of the symptoms or conditions associated with immune related disease, diabetes, graft vs. host disease, immunodeficiency disease, hematopoietic malignancy, hematopoietic failure, hematopoietic progenitor/stem cell transplantation, a muscle degenerative disease, or other disorders. "Therapeutic effect" refers to the reduction, elimination, or prevention of the disease, symptoms of the disease, or side effects of the disease in the subject.

"Concomitant administration" of a known drug with a compound of the present invention means administration of the drug and the compound at such time that both the known drug and the compound will have a therapeutic effect or diagnostic effect. Such concomitant administration can involve concurrent (i.e. at the same time), prior, or subsequent administration of the drug with respect to the administration of a compound of the present invention. A person of ordinary skill in the art, would have no difficulty determining the appropriate timing, sequence and dosages of administration for particular drugs and compounds of the present invention.

"Subject", "mammalian subject" or "patient" refers to any mammalian patient or subject to which the compositions of the invention can be administered. "Mammal" or "mammalian" refers to human patients and non-human primates, as well as experimental animals such as rabbits, rats, and mice, and other animals. In an exemplary embodiment, of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that can be associated with the targeted or suspected disease or condition. These and other routine methods allow the clinician to select patients in need of therapy using the methods and formulations of the invention.

By "solid phase" is meant a non-aqueous matrix to which a reagent of interest (e.g., Wnt, β-catenin, or Frizzled receptor, or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g.,an affinity chromatography column). This term also includes a discontinuous solid phase of discrete particles, such as those described in U.S. Pat. No. 4,275,149.

"Specifically (or selectively) binds" to an antibody refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

"Specifically bind(s)" or "bind(s) specifically" when referring to a peptide refers to a peptide molecule which has intermediate or high binding affinity, exclusively or predominately, to a target molecule. The phrase "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically affect Wnt signaling, β-catenin signaling, or Frizzled receptor proteins. Typically a specific or selective reaction will be at least twice background signal or noise and more typically more than 10 times background. Specific binding between a monovalent peptide and Wnt signaling, β-catenin signaling; or Frizzled receptor proteins means a binding affinity of at least $10^3$ M$^-$, and preferably $10^5$, $10^6$, $10^7$, $10^8$, $10^9$ or $10^{10}$ M$^-$. The binding affinity of Wnt to the Frizzled receptor is between about $10^6$ M$^{-1}$ to about $10^{10}$ M$^-$.

The present invention is based on the discovery that in vivo administration of one or more Wnt/β-catenin signal-, Notch signal- or Hedgehog signal-promoting agents, e.g., GSK-3 inhibitor, increases repopulating function of transplanted wild-type mouse HSCs, and augments human neonatal and adult HSC capacity in vivo. In the present invention, the role of ATP-competitive GSK-3 inhibitors has been investigated in the regulation of mouse and human HSCs. The findings demonstrate that GSK-3 inhibitors augment HSC function in vivo and modulate Wnt, Hedgehog, and Notch targets specifically in HSCs, thereby providing a potent and unique approach to directly enhance HSC function in vivo.

This invention relies on routine techniques in the field of recombinant genetics. Basic texts disclosing the general methods of use in this invention include Sambrook et al., *Molecular Cloning, A Laboratory Manual,* 2nd ed., 1989; Kriegler, *Gene Transfer and Expression: A Laboratory Manual,* 1990; and Ausubel et al., eds., *Current Protocols in Molecular Biology,* 1994.

Wnt, β-catenin, Notch, or Hedgehog nucleic acids, polymorphic variants, orthologs, and alleles that are substantially identical to sequences provided herein can be isolated using Wnt, β-catenin, Notch, or Hedgehog nucleic acid probes and oligonucleotides under stringent hybridization conditions, by screening libraries. Alternatively, expression libraries can be used to clone Wnt, β-catenin, Notch, or Hedgehog receptor protein, polymorphic variants, orthologs, and alleles by detecting expressed homologs immunologically with antisera or purified antibodies made against human Wnt, β-catenin, Notch, or Hedgehog portions thereof.

Identification of Compounds for Treatment and Prophylaxis of Disease (A) Identification of Bioactive Agents Identifying bioactive agents that modulate Wnt/β-catenin signaling, Notch signaling or Hedgehog signaling, the information is used in a wide variety of ways. In one method, one of several cellular assays, e.g., Wnt/β-catenin signaling, Notch signaling or Hedgehog signaling assay, can be used in conjunction with high throughput screening techniques, to allow monitoring for antagonists or agonists of Wnt/β-catenin signaling, Notch signaling or Hedgehog signaling after treatment with a candidate agent, Zlokarnik, et al., *Science* 279:84-8, 1998; and Heid et al., Genome Res. 6:986, 1996; each incorporated herein by reference in their entirety. In one method, the candidate agents are added to cells.

"Candidate bioactive agent" or "drug candidate" or grammatical equivalents as used herein describes any molecule, e.g., protein, oligopeptide, small organic molecule, polysaccharide, polynucleotide, to be tested for bioactive agents that are capable of directly or indirectly altering the activity of Wnt/β-catenin signaling, Notch signaling or Hedgehog signaling. In one methods, the bioactive agents modulate Wnt/β-catenin signaling, Notch signaling or Hedgehog signaling. In a further embodiment of the method, the candidate agents induce an antagonist or agonist effect in a Wnt/β-catenin signaling, Notch signaling or Hedgehog signaling assay, as further described below. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In some embodiments, the candidate bioactive agents are proteins. By "protein" herein is meant at least two covalently attached amino acids, which includes proteins, polypeptides, oligopeptides and peptides. The protein can be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the methods herein. "Amino acid" also includes imino acid residues such as proline and hydroxyproline. The side chains can be in either the (R) or the (S) configuration. In further embodiments, the amino acids are in the (S) or (L)-configuration. If non-naturally occurring side chains are used, non-amino acid substituents can be used, for example to prevent or retard in vivo degradations.

In one method, the candidate bioactive agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and mammalian proteins, and human proteins.

In some methods, the candidate bioactive agents are peptides of from about 5 to about 30 amino acids, typically from about 5 to about 20 amino acids, and typically from about 7 to about 15 being. The peptides can be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In some methods, the library can be fully randomized, with no sequence preferences or constants at any position. In other methods, the library can be biased. Some positions within the sequence are either held constant, or are selected from a limited number of possibilities. For example, in some methods, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, or to purines. In other methods, the candidate bioactive agents are nucleic acids, as defined above.

As described above generally for proteins, nucleic acid candidate bioactive agents can be naturally occurring nucleic acids, random nucleic acids, or "biased" random nucleic acids. For example, digests of procaryotic or eucaryotic genomes can be used as is outlined above for proteins.

In some methods, the candidate bioactive agents are organic chemical moieties.

(B) Drug Screening Methods

Several different drug screening methods can be accomplished to identify drugs or bioactive agents that act as Wnt/β-catenin signal-, Notch signal- or Hedgehog signal-promoting agents. One such method is the screening of candidate agents that can act as agonists of Wnt/β-catenin signaling, Notch signaling or Hedgehog signaling, thus generating the associated phenotype. Similarly, candidate agents that can act as an agonist to Wnt/β-catenin signaling, Notch signaling or Hedgehog signaling, as shown herein, are expected to result in the immunostimulant phenotype, upon challenge with a pathogen. Thus, in some methods, candidate agents can be determined that mimic or alter Wnt/β-catenin signaling, Notch signaling or Hedgehog signaling.

In other methods, screening can be done to alter the biological function of Wnt/β-catenin signaling, Notch signaling or Hedgehog signaling. Again, having identified the importance of a Wnt binding to the Frizzled receptor, or intracellular accumulation of β-catenin, screening for agents that bind and/or modulate the biological activity of the Wnt/β-catenin signaling, Notch signaling or Hedgehog signaling can be performed as outlined below.

Thus, screening of candidate agents that modulate Wnt/β-catenin signaling, Notch signaling or Hedgehog signaling either at the level of gene expression or protein level can be accomplished.

In some methods, a candidate agent can be administered in any one of several cellular assays, e.g., Wnt/β-catenin signaling, Notch signaling or Hedgehog signaling assay. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e., a peptide) can be put into a viral construct such as a retroviral construct and added to the cell, such that expression of the peptide agent is accomplished; see PCT US97/01019, incorporated herein by reference in its entirety.

Once the candidate agent has been administered to the cells, the cells can be washed if desired and are allowed to incubate under physiological conditions for some period of time. The cells are then harvested and a new gene expression profile is generated, as outlined herein.

For example, Wnt/β-catenin signal-, Notch signal- or Hedgehog signal-promoting agents can be screened for agents that produce an immune-stimulating phenotype. A change in a binding assay or cellular assay indicates that the agent has an effect on Wnt/β-catenin signaling, Notch signaling or Hedgehog signaling activity. In one method, an immunosuppressive or immune-stimulating profile is induced or maintained, before, during, and/or after stimulation with ligand. By defining such a signature for inhibiting or enhancing an immune response, or treating autoimmune disease, neoplastic disease, systemic lupus erthymatosus, or allogeneic tissue rejection, screens for new drugs that mimic the an immunosuppressive or immune-stimulating phenotype can be devised. With this approach, the drug target need not be known and need not be represented in the original expression screening platform, nor does the level of transcript for the target protein need to change. In some methods, the agent acts as an agonist or antagonist in one of several cellular or binding assays, e.g., Wnt/β-catenin signaling, Notch signaling or Hedgehog signaling assay.

In some methods, screens can be done on individual genes and gene products. After having identified a cellular or binding assay as indicative of inhibition or enhancement of an immune response, or treatment of autoimmune disease, neoplastic disease, systemic lupus erthymatosus, or allogeneic tissue rejection, screening of modulators of cellular or binding assay can be completed.

Thus, in some methods, screening for modulators of cellular or binding assay can be completed. This will be done as outlined above, but in general a few cellular or binding assay are evaluated. In some methods, screens are designed to first find candidate agents that can affect a cellular activity or binding assay, and then these agents can be used in other assays that evaluate the ability of the candidate agent to modulate Wnt/β-catenin signaling, Notch signaling or Hedgehog signaling.

In general, purified or isolated gene product can be used for binding assays; that is, the gene products of Wnt/β-catenin signaling, Notch signaling or Hedgehog signaling are made. Using the nucleic acids of the methods and compositions herein which encode Wnt, β-catenin, Notch, or Hedgehog polypeptides, or compounds of Wnt- or β-catenin-signaling, a variety of expression vectors can be made. The expression vectors can be either self-replicating extrachromosomal vectors or vectors which integrate into a host genome. Generally, these expression vectors include transcriptional and translational regulatory nucleic acid operably linked to the nucleic acid encoding a Wnt signaling or β-catenin protein. "Control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express Wnt/β-catenin signal-, Notch signal- or Hedgehog signal-promoting protein; for example, transcriptional and translational regulatory nucleic acid sequences from *Bacillus* are used to express the protein in *Bacillus*. Numerous types of appropriate expression vectors, and suitable regulatory sequences are known in the art for a variety of host cells.

In general, the transcriptional and translational regulatory sequences can include, but are not limited to, promoter sequences, ribosomal binding sites, transcriptional start and stop sequences, translational start and stop sequences, and enhancer or activator sequences. In one method, the regulatory sequences include a promoter and transcriptional start and stop sequences.

Promoter sequences encode either constitutive or inducible promoters. The promoters can be either naturally occurring promoters or hybrid promoters. Hybrid promoters, which combine elements of more than one promoter, are also known in the art, and are useful in the methods herein.

In addition, the expression vector can comprise additional elements. For example, the expression vector can have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and typically two homologous sequences which flank the expression construct. The integrating vector can be directed to a specific locus in the host cell by selecting the appropriate homologous sequence for inclusion in the vector. Constructs for integrating vectors are well known in the art. Methods to effect homologous recombination are described in PCT US93/03868 and PCT US98/05223, each incorporated herein by reference in their entirety.

In some methods, the expression vector contains a selectable marker gene to allow the selection of transformed host cells. Selection genes are well known in the art and will vary with the host cell used.

One expression vector system is a retroviral vector system such as is generally described in PCT/US97/01019 and PCT/US97/01048, each incorporated herein by reference in their entirety.

The Wnt/β-catenin signal-, Notch signal- or Hedgehog signal-promoting proteins of the present methods and compositions are produced by culturing a host cell transformed with an expression vector containing nucleic acid encoding Wnt/β-catenin signal-, Notch signal- or Hedgehog signal-promoting polypeptide, under the appropriate conditions to induce or cause expression of the protein. The conditions appropriate for Wnt/β-catenin signal-, Notch signal- or Hedgehog signal-promoting polypeptide expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In some methods, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are Drosophila melanogaster cells, *Saccharomyces cerevisiae* and other yeasts, *E. coli, Bacillus subtilis*, SF9 cells, C129 cells, 293 cells, *Neurospora*, BHK, CHO, COS, and HeLa cells. In some methods, hematopoietic progenitor/stem cells or neural progenitor cells, muscle progenitor cells are host cells as provided herein, which for example, include non-recombinant cell lines, such as primary cell lines. In addition, purified primary hematopoietic stem cells or neural progenitor cells, muscle progenitor cells for TNF assay derived from either transgenic or non-transgenic strains can also be used. The host cell can alternatively be an cell type known to have immunodeficiency disorder.

In one method, the Wnt/β-catenin signal-, Notch signal- or Hedgehog signal-promoting proteins are expressed in mammalian cells. Mammalian expression systems can include retroviral systems. A mammalian promoter is any DNA sequence capable of binding mammalian RNA polymerase and initiating the downstream (3') transcription of a coding sequence for Wnt/β-catenin signal-, Notch signal- or Hedgehog signal-promoting protein into niRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some methods, Wnt/β-catenin signal-, Notch signal- or Hedgehog signal-promoting proteins are expressed in bacterial systems which are well known in the art.

In other methods, Wnt/β-catenin signal-, Notch signal- or Hedgehog signal-promoting proteins can be produced in insect cells. Expression vectors for the transformation of insect cells, and in particular, baculovirus-based expression vectors, are well known in the art.

In some methods, Wnt/β-catenin signal-, Notch signal- or Hedgehog signal-promoting proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

A Wnt/β-catenin signal-, Notch signal- or Hedgehog signal-promoting protein can also be made as a fusion protein, using techniques well known in the art. For example, for the creation of monoclonal antibodies, if the desired epitope is small, the protein can be fused to a carrier protein to form an immunogen. Alternatively, Wnt/β-catenin signal-, Notch signal- or Hedgehog signal-promoting protein can be made as a fusion protein to increase expression. For example, when a protein is a shorter peptide, the nucleic acid encoding the peptide can be linked to other nucleic acid for expression purposes. Similarly, Wnt/β-catenin signal-, Notch signal- or Hedgehog signal-promoting proteins of the methods and compositions herein can be linked to protein labels, such as green fluorescent protein (GFP), red fluorescent protein (RFP), yellow fluorescent protein (YFP), and blue fluorescent protein (BFP).

In one embodiment, the proteins are recombinant. A "recombinant protein" is a protein made using recombinant techniques, i.e., through the expression of a recombinant nucleic acid as depicted above. A recombinant protein is distinguished from naturally occurring protein by at least one or more characteristics. For example, the protein can be isolated or purified away from some or all of the proteins and compounds with which it is normally associated in its wild type host, and thus can be substantially pure. For example, an isolated protein is unaccompanied by at least some of the material with which it is normally associated in its natural state, typically constituting at least about 0.5%, typically at least about 5% by weight of the total protein in a given sample. A substantially pure protein comprises at least about 75% by weight of the total protein, at least about 80%, and typically at least about 90%. The definition includes the production of Wnt/β-catenin signal-, Notch signal- or Hedgehog signal-promoting protein from one organism in a different organism or host cell. Alternatively, the protein can be made at a significantly higher concentration than is normally seen, through the use of a inducible promoter or high expression promoter, such that the protein is made at increased concentration levels. Alternatively, the protein can be in a form not normally found in nature, as in the addition of an epitope tag or amino acid substitutions, insertions and deletions, as discussed below.

In some methods, when the Wnt/β-catenin signal-, Notch signal- or Hedgehog signal-promoting protein is to be used to generate antibodies, the protein must share at least one epitope or determinant with the full length transcription product of the nucleic acids. By "epitope" or "determinant" herein is meant a portion of a protein which will bind an antibody. Thus, in most instances, antibodies made to a smaller protein should be able to bind to the full length protein. In one embodiment, the epitope is unique; that is, antibodies generated to a unique epitope show little or no cross-reactivity.

In some methods, the antibodies provided herein can be capable of reducing or eliminating the biological function of a Wnt/β-catenin signal-, Notch signal- or Hedgehog signal-promoting protein, as is described below. The addition of antibodies (either polyclonal or monoclonal) to the protein (or cells containing the protein) can reduce or eliminate the protein's activity. Generally, at least a 25% decrease in activity is observed, with typically at least about 50% and typically about a 95-100% decrease being observed.

In addition, the proteins can be variant proteins, comprising one more amino acid substitutions, insertions and deletions.

In one method, a Wnt/β-catenin signal-, Notch signal- or Hedgehog signal-promoting protein is purified or isolated after expression. Proteins can be isolated or purified in a variety of ways. Standard purification methods include electrophoretic, molecular, immunological and chromatographic techniques, including ion exchange, hydrophobic, affinity, and reverse-phase HPLC chromatography, and chromatofocusing. For example, a Wnt/β-catenin signal-, Notch signal- or Hedgehog signal-promoting protein can be purified using a standard anti-Wnt, anti-β-catenin, anti-Notch, or anti-Hedgehog protein antibody column. Ultrafiltration and diafiltration techniques, in conjunction with protein concentration, are also useful. For general guidance in suitable purification techniques, see Scopes, *Protein Purification*, Springer-Verlag, NY, 1982, incorporated herein by reference in its entirety. The degree of purification necessary will vary depending on the use of the protein. In some instances no purification will be necessary.

Once the gene product of the Wnt/β-catenin signal-, Notch signal- or Hedgehog signal-promoting gene is made, binding assays can be done. These methods comprise combining a Wnt/β-catenin signal-, Notch signal- or Hedgehog signal-promoting protein and a candidate bioactive agent, and determining the binding of the candidate agent to the Wnt/β-catenin signal-, Notch signal- or Hedgehog signal-promoting protein. Methods utilize a human Wnt/β-catenin signal-, Notch signal- or Hedgehog signal-promoting protein, although other mammalian proteins can also be used, including rodents (mice, rats, hamsters, guinea pigs), farm animals (cows, sheep, pigs, horses) and primates. These latter methods can be used for the development of animal models of human disease. In some methods, variant or derivative Wnt/β-catenin signal-, Notch signal- or Hedgehog signal-promoting proteins can be used, including deletion Wnt/β-catenin signal-, Notch signal- or Hedgehog signal-promoting proteins as outlined above.

The assays herein utilize Wnt/β-catenin signal-, Notch signal- or Hedgehog signal-promoting proteins as defined herein. In some assays, portions of proteins can be utilized. In other assays, portions having different activities can be used. In addition, the assays described herein can utilize either isolated Wnt/β-catenin signal-, Notch signal- or Hedgehog signal-promoting proteins or cells comprising the Wnt/β-catenin signal-, Notch signal- or Hedgehog signal-promoting proteins. In some methods, the protein or the candidate agent is non-diffusably bound to an insoluble support having isolated sample receiving areas (e.g., a microtiter plate or an array). The insoluble supports can be made of any composition to which the compositions can be bound, is readily separated from soluble material, and is otherwise compatible with the overall method of screening. The surface of such supports can be solid or porous and of any convenient shape. Examples of suitable insoluble supports include microtiter plates, arrays, membranes and beads. These are typically made of glass, plastic (e.g., polystyrene), polysaccharides, nylon or nitrocellulose, and teflon™. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods described herein, maintains the activity of the composition and is nondiffusable. Methods of binding include the use of antibodies (which do not sterically block either the ligand binding site or activation sequence when the protein is bound to the support), direct binding to ionic supports, chemical crosslinking, or by the synthesis of the protein or agent on the surface. Following binding of the protein or agent, excess unbound material is removed by washing. The sample receiving areas can then be blocked through incubation with bovine serum albumin (BSA), casein or other innocuous protein or other moiety. Also included in the methods and compositions herein are screening assays wherein solid supports are not used.

In other methods, the Wnt/β-catenin signal-, Notch signal- or Hedgehog signal-promoting protein is bound to the support, and a candidate bioactive agent is added to the assay. Alternatively, the candidate agent is bound to the support and the protein is added. Novel binding agents include specific antibodies, non-natural binding agents identified in screens of chemical libraries, and peptide analogs. Of particular interest are screening assays for agents that have a low toxicity for human cells. A wide variety of assays can be used for this purpose, including labeled in vitro protein-protein binding assays, electrophoretic mobility shift assays, immunoassays for protein binding, functional assays (such as phosphorylation assays) and the like.

The determination of the binding of the candidate bioactive agent to a Wnt/β-catenin signal-, Notch signal- or Hedgehog signal-promoting protein can be done in a number of ways. In some methods, the candidate bioactive agent is labeled, and binding determined directly. For example, this can be done by attaching all or a portion of a Wnt/β-catenin signal-, Notch signal- or Hedgehog signal-promoting protein to a solid support, adding a labeled candidate agent (for example a fluorescent label), washing off excess reagent, and determining whether the label is present on the solid support. Various blocking and washing steps can be utilized.

By "labeled" herein is meant that the compound is either directly or indirectly labeled with a label which provides a detectable signal, e.g., radioisotope, fluorescers, enzyme, antibodies, particles such as magnetic particles, chemiluminescers, or specific binding molecules. Specific binding molecules include pairs, such as biotin and streptavidin, digoxin and antidigoxin. For the specific binding members, the complementary member would normally be labeled with a molecule which provides for detection, in accordance with known procedures, as outlined above. The label can directly or indirectly provide a detectable signal.

In some methods, only one of the components is labeled. For example, the proteins (or proteinaceous candidate agents) can be labeled at tyrosine positions using $^{125}$I, or with fluorophores. Alternatively, more than one component can be labeled with different labels; using $^{125}$I for the proteins, for example, and a fluorophor for the candidate agents.

In other methods, the binding of the candidate bioactive agent is determined through the use of competitive binding assays. In this method, the competitor is a binding moiety known to bind to the target molecule such as an antibody, peptide, binding partner, or ligand. Under certain circumstances, there can be competitive binding as between the bioactive agent and the binding moiety, with the binding moiety displacing the bioactive agent. This assay can be used to determine candidate agents which interfere with binding between proteins and the competitor.

In some methods, the candidate bioactive agent is labeled. Either the candidate bioactive agent, or the competitor, or both, is added first to the protein for a time sufficient to allow binding, if present. Incubations can be performed at any temperature which facilitates optimal activity, typically between about 4° C. and 40° C. Incubation periods are selected for optimum activity, but can also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In other methods, the competitor is added first, followed by the candidate bioactive agent. Displacement of the competitor is an indication that the candidate bioactive agent is binding to the Wnt/β-catenin signal-, Notch signal- or Hedgehog signal-promoting protein and thus is capable of binding to, and potentially modulating, the activity of the protein. In this method, either component can be labeled. For example, if the competitor is labeled, the presence of label in the wash solution indicates displacement by the agent. Alternatively, if the candidate bioactive agent is labeled, the presence of the label on the support indicates displacement.

In other methods, the candidate bioactive agent is added first, with incubation and washing, followed by the competitor. The absence of binding by the competitor can indicate that the bioactive agent is bound to the Wnt/β-catenin signal-, Notch signal- or Hedgehog signal-promoting protein with a higher affinity. Thus, if the candidate bioactive agent is labeled, the presence of the label on the support, coupled with a lack of competitor binding, can indicate that the candidate agent is capable of binding to the protein.

Competitive binding methods can also be run as differential screens. These methods can comprise a Wnt/β-catenin signal-, Notch signal- or Hedgehog signal-promoting protein and a competitor in a first sample. A second sample comprises a candidate bioactive agent, a Wnt/β-catenin signal-, Notch signal- or Hedgehog signal-promoting protein and a competitor. The binding of the competitor is determined for both samples, and a change, or difference in binding between the two samples indicates the presence of an agent capable of binding to the Wnt/β-catenin signal-, Notch signal- or Hedgehog signal-promoting protein and potentially modulating its activity. If the binding of the competitor is different in the second sample relative to the first sample, the agent is capable of binding to the protein.

Other methods utilize differential screening to identify drug candidates that bind to the native Wnt/β-catenin signal-, Notch signal- or Hedgehog signal-promoting protein, but cannot bind to modified proteins. The structure of the protein can be modeled, and used in rational drug design to synthesize agents that interact with that site. Drug candidates that affect Wnt/β-catenin signaling, Notch signaling or Hedgehog signaling bioactivity are also identified by screening drugs for the ability to either enhance or reduce the activity of the protein.

In some methods, screening for agents that modulate the activity of proteins are performed. In general, this will be done on the basis of the known biological activity of the Wnt/β-catenin signal-, Notch signal- or Hedgehog signal-promoting protein. In these methods, a candidate bioactive agent is added to a sample of the protein, as above, and an alteration in the biological activity of the protein is determined. "Modulating the activity" includes an increase in activity, a decrease in activity, or a change in the type or kind of activity present. Thus, in these methods, the candidate agent should both bind to a Wnt/β-catenin signal-, Notch signal- or Hedgehog signal-promoting polypeptide (although this may not be necessary), and alter its biological or biochemical activity as defined herein. The methods include both in vitro screening methods, as are generally outlined above, and in vivo screening of cells for alterations in the presence, distribution, activity or amount of the protein.

Some methods comprise combining a Wnt/β-catenin signal-, Notch signal- or Hedgehog signal-promoting polypeptide sample and a candidate bioactive agent, then evaluating the effect on Wnt/β-catenin signaling, Notch signaling or Hedgehog signaling activity to inhibit or enhance an immune response. By "Wnt/β-catenin signaling, Notch signaling or Hedgehog signaling activity" or grammatical equivalents herein is meant one of Wnt/β-catenin signaling, Notch signaling or Hedgehog signaling biological activities, including, but not limited to, its ability to affect immune activation or inhibition. One activity herein is the capability to bind to a target gene, or modulate Wnt/β-catenin signaling, Notch signaling or Hedgehog signaling, for example, wherein Wnt/β-catenin signaling, Notch signaling or Hedgehog signaling is induced or maintained.

In other methods, the activity of the Wnt/β-catenin signal-, Notch signal- or Hedgehog signal-promoting protein is increased; in other methods, the activity of the Wnt/β-catenin signal-, Notch signal- or Hedgehog signal-promoting protein is decreased. Thus, bioactive agents that are antagonists are useful in some methods, and bioactive agents that are agonists are useful in other methods.

Methods for screening for bioactive agents capable of modulating the activity of a Wnt/β-catenin signal-, Notch signal- or Hedgehog signal-promoting protein are provided. These methods comprise adding a candidate bioactive agent, as defined above, to a cell comprising proteins. Cell types include almost any cell. The cells contain a recombinant nucleic acid that encodes a Wnt/β-catenin signal-, Notch signal- or Hedgehog signal-promoting protein. In one method, a library of candidate agents are tested on a plurality of cells. The effect of the candidate agent on Wnt/β-catenin signaling, Notch signaling or Hedgehog signaling activity is then evaluated.

Positive controls and negative controls can be used in the assays. All control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins (e.g., albumin and detergents) which can be used to facilitate optimal protein-protein binding and/or reduce non-specific or background interactions. Reagents that otherwise improve the efficiency of the assay, (such as protease inhibitors, nuclease inhibitors, anti-microbial agents) can also be used. The mixture of components can be added in any order that provides for the requisite binding.

The components provided herein for the assays provided herein can also be combined to form kits. The kits can be based on the use of the protein and/or the nucleic acid encoding the Wnt/β-catenin signal-, Notch signal- or Hedgehog signal-promoting proteins. Assays regarding the use of nucleic acids are further described below.

(C) Animal Models

In one method, nucleic acids which encode Wnt/β-catenin signal-, Notch signal- or Hedgehog signal-promoting proteins or their modified forms can also be used to generate either transgenic animals, including "knock-in" and "knock out" animals which, in turn, are useful in the development and screening of therapeutically useful reagents. A non-human transgenic animal (e.g., a mouse or rat) is an animal having cells that contain a transgene, which transgene is introduced into the animal or an ancestor of the animal at a prenatal, e.g., an embryonic stage. A transgene is a DNA which is integrated into the genome of a cell from which a transgenic animal develops, and can include both the addition of all or part of a gene or the deletion of all or part of a gene. In some methods, cDNA encoding a Wnt/β-catenin signal-, Notch signal- or Hedgehog signal-promoting protein can be used to clone genomic DNA encoding a Wnt/β-catenin signal-, Notch signal- or Hedgehog signal-promoting protein in accordance with established techniques and the genomic sequences used to generate transgenic animals that contain cells which either express (or overexpress) or suppress the desired DNA. Methods for generating transgenic animals, particularly animals such as mice or rats, have become conventional in the art and are described, for example, in U.S. Pat. Nos. 4,736,866 and 4,870,009, each incorporated herein by reference in their entirety. Typically, particular cells would be targeted for a Wnt/β-catenin signal-, Notch signal- or Hedgehog signal-promoting protein transgene incorporation with tissue-specific enhancers. Transgenic animals that include a copy of a transgene encoding a Wnt/β-catenin signal-, Notch signal- or Hedgehog signal-promoting protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet, an animal is treated with the reagent and a reduced incidence of the pathological condition, compared to untreated animals bearing the transgene, would indicate a potential therapeutic intervention for the pathological condition. Similarly, non-human homologues of a Wnt/β-catenin signal-, Notch signal- or Hedgehog signal-promoting protein can be used to construct a transgenic animal comprising a protein "knock out" animal which has a defective or altered gene encoding a Wnt/β-catenin signal-, Notch signal- or Hedgehog signal-promoting protein as a result of homologous recombination between the endogenous gene encoding a Wnt/β-catenin signal-, Notch signal- or Hedgehog signal-promoting protein and altered genomic DNA encoding the protein introduced into an embryonic cell of the animal. For example, cDNA encoding a Wnt/β-catenin signal-, Notch signal- or Hedgehog signal-promoting protein can be used to clone genomic DNA encoding the protein in accordance with established techniques. A portion of the genomic DNA encoding a Wnt/β-catenin signal-, Notch signal- or Hedgehog signal-promoting protein can be deleted or replaced with another gene, such as a gene encoding a selectable marker which can be used to monitor integration. Typically, several kilobases of unaltered flanking DNA (both at the 5' and 3' ends) are included in the vector (see, e.g., Thomas and Capecchi, *Cell* 51:503, 1987, incorporated herein by reference in its entirety, for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell* 69:915, 1992, incorporated herein by reference in its entirety). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of a Wnt/β-catenin signal-, Notch signal- or Hedgehog signal-promoting polypeptide.

Animal models for Wnt/β-catenin signaling, Notch signaling or Hedgehog signaling related disorders, or having a particular state of Wnt/β-catenin signaling, Notch signaling or Hedgehog signaling activity can include, for example, genetic models. For example, such animal models for immune related disease can include GFP/FVB mouse, (Tsirigotis et al., *Biotechniques* 31:120-126, 128, 130, 2001); C57BL/6 mouse, Tg(Fos-lacZ)34Efu (TOP-gal) mouse, (DasGupta and Fuchs, *Development* 126:4557-4568, 1999); Ptc-1$^{+/-lacZ}$ mouse (Goodrich et al., *Science* 277:1109-1113, 1997); and NOD/LtSz-scid/scid (NOD/SCID) mouse. Each incorporated herein by reference in their entirety. Other models can include studies involving transplant rejection.

Animal models exhibiting Wnt/β-catenin signaling, Notch signaling or Hedgehog signaling related disorder-like symptoms can be engineered by utilizing, for example, Wnt/β-catenin signal-, Notch signal- or Hedgehog signal-promoting polypeptide sequences in conjunction with techniques for producing transgenic animals that are well known to those of skill in the art. For example, gene sequences can be introduced into, and overexpressed in, the genome of the animal of interest, or, if endogenous target gene sequences are present, they can either be overexpressed or, alternatively, can be disrupted in order to underexpress or inactivate target gene expression.

In order to overexpress a target gene sequence, the coding portion of the target gene sequence can be ligated to a regulatory sequence which is capable of driving gene expression in the animal and cell type of interest. Such regulatory regions will be well known to those of skill in the art, and can be utilized in the absence of undue experimentation.

For underexpression of an endogenous target gene sequence, such a sequence can be isolated and engineered such that when reintroduced into the genome of the animal of interest, the endogenous target gene alleles will be inactivated. The engineered target gene sequence is introduced via gene targeting such that the endogenous target sequence is disrupted upon integration of the engineered target sequence into the animal's genome.

Animals of any species, including, but not limited to, mice, rats, rabbits, guinea pigs, pigs, micro-pigs, goats, and non-human primates, e.g., baboons, monkeys, and chimpanzees can be used to generate animal models of Wnt/β-catenin signaling, Notch signaling or Hedgehog signaling related disorders or being a perpetually desired state of the Wnt/β-catenin signaling, Notch signaling or Hedgehog signaling.

(D) Nucleic Acid Based Therapeutics

Nucleic acids encoding Wnt/β-catenin signal-, Notch signal- or Hedgehog signal-promoting polypeptides, antagonists or agonists can also be used in gene therapy. Broadly speaking, a gene therapy vector is an exogenous polynucleotide which produces a medically useful phenotypic effect upon the mammalian cell(s) into which it is transferred. A vector can or can not have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA. Vectors used in gene therapy can be viral or nonviral. Viral vectors are usually introduced into a patient as components of a virus. Nonviral vectors, typically dsDNA, can be transferred as naked DNA or associated with a transfer-enhancing vehicle, such as a receptor-recognition protein, lipoamine, or cationic lipid.

Viral vectors, such as retroviruses, adenoviruses, adenoassociated viruses and herpes viruses, are often made up of two components, a modified viral genome and a coat structure surrounding it (see generally Smith et al., *Ann. Rev. Microbiol.* 49:807-838, 1995, incorporated herein by reference in its entirety), although sometimes viral vectors are introduced in naked form or coated with proteins other than viral proteins. Most current vectors have coat structures similar to a wildtype virus. This structure packages and protects the viral nucleic acid and provides the means to bind and enter target cells. However, the viral nucleic acid in a vector designed for gene therapy is changed in many ways. The goals of these changes are to disable growth of the virus in target cells while maintaining its ability to grow in vector form in available packaging or helper cells, to provide space within the viral genome for insertion of exogenous DNA sequences, and to incorporate new sequences that encode and enable appropriate expression of the gene of interest. Thus, vector nucleic acids generally comprise two components: essential cis-acting viral sequences for replication and packaging in a helper line and the transcription unit for the exogenous gene. Other viral functions are expressed in trans in a specific packaging or helper cell line.

Nonviral nucleic acid vectors used in gene therapy include plasmids, RNAs, antisense oligonucleotides (e.g., methylphosphonate or phosphorothiolate), polyamide nucleic acids, interfering RNA (RNAi), hairpin RNA, and yeast artificial chromosomes (YACs). Such vectors typically include an expression cassette for expressing a protein or RNA. The promoter in such an expression cassette can be constitutive, cell type-specific, stage-specific, and/or modulatable (e.g., by hormones such as glucocorticoids; MMTV promoter). Transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Gene therapy vectors can be delivered in vivo by administration to an individual patient, typically by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Modulating Signaling in Wnt/β-Catenin Signaling, Notch Signaling or Hedgehog Signaling Pathway (A) Assays for Modulators of Wnt/β-Catenin Signaling, Notch Signaling or Hedgehog Signaling In numerous embodiments of this invention, the level of Wnt/β-catenin signaling, Notch signaling or Hedgehog signaling will be modulated in a cell by administering to the cell, in vivo or in vitro, any of a large number of Wnt/β-catenin signal-, Notch signal- or Hedgehog signal-promoting molecules, e.g., polypeptides, antibodies, amino acids, nucleotides, lipids, carbohydrates, or any organic or inorganic molecule.

To identify molecules capable of modulating Wnt/β-catenin signaling, Notch signaling or Hedgehog signaling, assays will be performed to detect the effect of various compounds on Wnt/β-catenin signaling, Notch signaling or Hedgehog signaling activity in a cell. Wnt/β-catenin signaling, Notch signaling or Hedgehog signaling can be assessed using a variety of in vitro and in vivo assays to determine functional, chemical, and physical effects, e.g., measuring the binding of Wnt, β-catenin, Notch or Hedgehog to other molecules (e.g., radioactive binding to Wnt, β-catenin, Notch or Hedgehog), measuring protein and/or RNA levels of Wnt/β-catenin signaling, Notch signaling or Hedgehog signaling that provides an immunosuppressive or immune-stimulating response, or measuring other aspects of pathway signaling, e.g., phosphorylation levels, transcription levels, receptor activity, ligand binding and the like. Such assays can be used to test for both activators and inhibitors of Wnt/β-catenin signaling, Notch signaling or Hedgehog signaling. Modulators thus identified are useful for, e.g., many diagnostic and therapeutic applications.

The Wnt/β-catenin signaling, Notch signaling or Hedgehog signaling in the assay will typically be a recombinant or naturally occurring polypeptide or a conservatively modified variant thereof. Alternatively, the Wnt/β-catenin signaling, Notch signaling or Hedgehog signaling in the assay will be derived from a eukaryote and include an amino acid subsequence having amino acid sequence identity to the naturally occurring Wnt/β-catenin signaling, Notch signaling or Hedgehog signaling. Generally, the amino acid sequence identity will be at least 70%, optionally at least 75%, 85%, or 86%, 87%, 88%, 89%, 90%, 91%, 92%, 93%, 94%, 95%, 96%, 97%, 98% or greater. Optionally, the polypeptide of the assays will comprise a domain of a Wnt/β-catenin signal-, Notch signal- or Hedgehog signal-promoting polypeptide. In certain embodiments, a domain of Wnt, β-catenin, Notch, or Hedgehog protein is bound to a solid substrate and used, e.g., to isolate any molecules that can bind to and/or modulate their activity. In certain embodiments, a domain of a Wnt/β-catenin signal-, Notch signal- or Hedgehog signal-promoting polypeptide, e.g., an N-terminal domain, a C-terminal domain, is fused to a heterologous polypeptide, thereby forming a chimeric polypeptide. Such chimeric polypeptides are also useful, e.g., in assays to identify modulators of an Wnt/β-catenin signaling, Notch signaling or Hedgehog signaling.

"Identical" or percent "identity," in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding a collectin described herein or amino acid sequence of a collectin described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.*, 1981, 2:482, by the homology alignment algorithm of Needleman & Wunsch, *J. Mol. Biol.*, 1970, 48:443, by the search for similarity method of Pearson & Lipman, *Proc. Nat'l. Acad. Sci. USA*, 1988, 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology, Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.*, 1977, 25:3389-3402 and Altschul et al., *J. Mol. Biol.*, 1990, 215:403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 1989, 89:10915) alignments (B) of 50, expectation (E) of 10, M=5, N=-4, and a comparison of both strands.

"Polypeptide", "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a kinase domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., Ausubel et al, supra.

For PCR, a temperature of about 36° C. is typical for low stringency amplification, although annealing temperatures can vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. PCR Protocols, A Guide to Methods and Applications, Academic Press, Inc. N.Y. (1990).

Samples or assays that are treated with a potential Wnt/β-catenin signaling, Notch signaling or Hedgehog signaling inhibitor or activator are compared to control samples without the test compound, to examine the extent of modulation. Control samples (untreated with activators or inhibitors) are assigned a relative activity value of 100. Inhibition of Wnt/β-catenin signaling, Notch signaling or Hedgehog signaling is achieved when the Wnt/β-catenin signaling, Notch signaling or Hedgehog signaling activity value relative to the control is about 90%, optionally about 50%, optionally about 25-0%. Activation of a Wnt/β-catenin signaling, Notch signaling or Hedgehog signaling is achieved when the Wnt/β-catenin signaling, Notch signaling or Hedgehog signaling activity value relative to the control is about 110%, optionally about 150%, 200-500%, or about 1000-2000%.

The effects of the test compounds upon the function of the polypeptides can be measured by examining any of the parameters described above. Any suitable physiological change that affects Wnt/β-catenin signaling, Notch signaling or Hedgehog signaling activity can be used to assess the influence of a test compound on the polypeptides of this invention. When the functional consequences are determined using intact cells or animals, one can also measure a variety of effects such as changes in cell growth or changes in cell-cell interactions.

Modulators of Wnt/β-catenin signaling, Notch signaling or Hedgehog signaling that act by modulating gene expression can also be identified. For example, a host cell containing a Wnt signaling or β-catenin protein of interest is contacted with a test compound for a sufficient time to effect any interactions, and then the level of gene expression is measured. The amount of time to effect such interactions can be empirically determined, such as by running a time course and measuring the level of transcription as a function of time. The amount of transcription can be measured using any method known to those of skill in the art to be suitable. For example, mRNA expression of the protein of interest can be detected using Northern blots or by detecting their polypeptide products using immunoassays.

(B) Assays for Wnt/β-catenin signaling, Notch Signaling or Hedgehog Signaling Compounds In certain embodiments, assays will be performed to identify molecules that physically interact with Wnt, β-catenin, Notch or Hedgehog. Such molecules can be any type of molecule, including polypeptides, polynucleotides, amino acids, nucleotides, carbohydrates, lipids, or any other organic or inorganic molecule. Such molecules can represent molecules that normally interact with Wnt, β-catenin, Notch or Hedgehog or can be synthetic or other molecules that are capable of interacting with Wnt, β-catenin, Notch or Hedgehog and that can potentially be used as lead compounds to identify classes of molecules that can interact with and/or modulate Wnt/β-catenin signaling, Notch signaling or Hedgehog signaling. Such assays can represent physical binding assays, such as affinity chromatography, immunoprecipitation, two-hybrid screens, or other binding assays, or can represent genetic assays.

In any of the binding or functional assays described herein, in vivo or in vitro, Wnt/β-catenin signaling, Notch signaling or Hedgehog signaling, or any derivative, variation, homolog, or fragment of Wnt signaling or β-catenin, can be used. Preferably, the Wnt/β-catenin signaling, Notch signaling or Hedgehog signaling protein has at least about 85% identity to the amino acid sequence of the naturally occurring Wnt/β-catenin signaling, Notch signaling or Hedgehog signaling protein. In numerous embodiments, a fragment of a Wnt, β-catenin, Notch or Hedgehog protein is used. Such fragments can be used alone, in combination with other Wnt/β-catenin signaling, Notch signaling or Hedgehog signaling protein fragments, or in combination with sequences from heterologous proteins, e.g., the fragments can be fused to a heterologous polypeptides, thereby forming a chimeric polypeptide.

Compounds that interact with Wnt/β-catenin signaling, Notch signaling or Hedgehog signaling can be isolated based on an ability to specifically bind to a Wnt, β-catenin, Notch or Hedgehog or fragment thereof. In numerous embodiments, the Wnt, β-catenin, Notch or Hedgehog or protein fragment will be attached to a solid support. In one embodiment, affinity columns are made using the Wnt, β-catenin, Notch or Hedgehog polypeptide, and physically-interacting molecules are identified. It will be apparent to one of skill that chromatographic techniques can be performed at any scale and using equipment from many different manufactures (e.g., Pharmacia Biotechnology). In addition, molecules that interact with Wnt, β-catenin, Notch or Hedgehog in vivo can be identified by co-immunoprecipitation or other methods, i.e., immunoprecipitating Wnt, β-catenin, Notch or Hedgehog using anti-Wnt or anti-β-catenin antibodies from a cell or cell extract, and identifying compounds, e.g., proteins, that are precipitated along with the Wnt, β-catenin, Notch or Hedgehog. Such methods are well known to those of skill in the art and are taught, e.g., in Ausubel et al., 1994; Sambrook et al., *Molecular Cloning: A Laboratory Manual*, Cold Spring Harbor Press, NY., 1989; and Harlow and Lane, *Antibodies: A Laboratory Manual*, Cold Spring Harbor Press, NY., 1989.

(C) Increasing Wnt, β-Catenin, Notch or Hedgehog Protein Activity Levels in Cells In certain embodiments, this invention provides methods of treating neoplastic disease, allogeneic tissue rejection, or graft vs. host disease by increasing Wnt, β-catenin, Notch or Hedgehog, or Wnt/β-catenin signaling, Notch signaling or Hedgehog signaling or protein levels in a cell. Typically, such methods are used to increase a reduced level of Wnt, β-catenin, Notch or Hedgehog protein, e.g., a reduced level in a hematopoietic stem cell or muscle progenitor cell, and can be performed in any of a number of ways, e.g., increasing the copy number of Wnt, β-catenin, Notch or Hedgehog genes or increasing the level of Wnt, β-catenin, Notch or Hedgehog mRNA, protein, or protein activity in a cell. Preferably, the level of protein activity is increased to a level typical of a normal cell, but the level can be increased to any level that is sufficient to increase Wnt/β-catenin signaling, Notch signaling or Hedgehog signaling in an hematopoietic stem cell or muscle progenitor cell, including to levels above or below those typical of normal cells. Preferably, such methods involve the use of activators of Wnt/β-catenin signaling, Notch signaling or Hedgehog signaling, where an "activator of Wnt/β-catenin signaling, Notch signaling or Hedgehog signaling" is a molecule that acts to increase Wnt, β-catenin, Notch or Hedgehog gene polynucleotide levels, polypeptide levels and/or protein activity. Such activators can include, but are not limited to, small molecule activators of Wnt/β-catenin signaling, Notch signaling or Hedgehog signaling.

In preferred embodiments, Wnt, β-catenin, Notch or Hedgehog protein levels or Wnt/β-catenin signaling, Notch signaling or Hedgehog signaling will be increased so as to increase hematopoietic stem cells, stem cells, muscle progenitor cells, or neural progenitor cells in vivo in a mammalian subject or to treat a immune related disease, degenerative muscle disease, or neurodegenerative disease in a mammalian subject as a result of decreased Wnt/β-catenin signaling, Notch signaling or Hedgehog signaling levels. The proliferation of a cell refers to the rate at which the cell or population of cells divides, or to the extent to which the cell or population of cells divides or increases in number. Proliferation can reflect any of a number of factors, including the rate of cell growth and division and the rate of cell death. Without being bound by the following offered theory, it is suggested that the amplification and/or overexpression of the Wnt/β-catenin signaling, Notch signaling or Hedgehog signaling in hematopoietic stem cells, stem cells, muscle progenitor cells, or neural progenitor cells to treat immune related disease or a degenerative muscle disease or neurodegenerative disease in a mammalian subject. Inhibition or activation of immune activity via Wnt, β-catenin, Notch or Hedgehog protein can act to treat immune related disease or a degenerative muscle disease or neurodegenerative disease in a mammalian subject. The ability of any of the present compounds to affect Wnt/β-catenin signaling, Notch signaling or Hedgehog signaling activity can be determined based on any of a number of factors, including, but not limited to, a level of Wnt, β-catenin, Notch or Hedgehog polynucleotide, e.g., mRNA or gDNA, the level of Wnt, β-catenin, Notch or Hedgehog polypeptide, the degree of binding of a compound to a Wnt, β-catenin, Notch or Hedgehog polynucleotide or polypeptide, Wnt, β-catenin, Notch or Hedgehog protein intracellular localization, or any functional properties of Wnt, β-catenin, Notch or Hedgehog protein, such as the ability of Wnt, β-catenin, Notch or Hedgehog protein activity to enhance an immune response, or treat immune related disease or a degenerative muscle disease or neurodegenerative disease in a mammalian subject.

(D) Regulators of Wnt, β-catenin, Notch or Hedgehog Polynucleotides

In certain embodiments, Wnt/β-catenin signaling, Notch signaling or Hedgehog signaling activity is regulated by the use of antisense polynucleotide, i.e., a nucleic acid complementary to, and which can preferably hybridize specifically to, a coding mRNA nucleic acid sequence, e.g., Wnt/β-catenin signaling, Notch signaling or Hedgehog signaling mRNA, or a subsequence thereof. Binding of the antisense polynucleotide to the mRNA reduces the translation and/or stability of the Wnt/β-catenin signaling, Notch signaling or Hedgehog signaling mRNA.

In the context of this invention, antisense polynucleotides can comprise naturally-occurring nucleotides, or synthetic species formed from naturally-occurring subunits or their close homologs. Antisense polynucleotides can also have altered sugar moieties or inter-sugar linkages. Exemplary among these are the phosphorothioate and other sulfur containing species which are known for use in the art. All such analogs are comprehended by this invention so long as they function effectively to hybridize with Wnt/β-catenin signaling, Notch signaling or Hedgehog signaling mRNA.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

In addition to antisense polynucleotides, ribozymes can be used to target and inhibit transcription of Wnt/β-catenin signaling, Notch signaling or Hedgehog signaling protein. A ribozyme is an RNA molecule that catalytically cleaves other RNA molecules. Different kinds of ribozymes have been described, including group I ribozymes, hammerhead ribozymes, hairpin ribozymes, RNAse P, and axhead ribozymes (see, e.g., Castanotto et al., *Adv. in Pharmacology* 25: 289-317, 1994 for a general review of the properties of different ribozymes).

The general features of hairpin ribozymes are described, e.g., in Hampel et al., *Nucl. Acids Res.*, 18: 299-304, 1990; Hampel et al., European Patent Publication No. 0 360 257, 1990; U.S. Pat. No. 5,254,678. Methods of preparing are well known to those of skill in the art (see, e.g., Wong-Staal et al., WO 94/26877; Ojwang et al., *Proc. Natl. Acad. Sci. USA*, 90: 6340-6344, 1993; Yamada et al., *Human Gene Therapy* 1: 39-45, 1994; Leavitt et al., *Proc. Natl. Acad. Sci. USA*, 92: 699-703, 1995; Leavitt et al., *Human Gene Therapy* 5: 1151-120, 1994; and Yamada et al., *Virology* 205: 121-126, 1994).

Wnt/β-catenin signaling, Notch signaling or Hedgehog signaling protein activity can also be increased by the addition of an activator or inhibitor of the Wnt, β-catenin, Notch or Hedgehog protein. This can be accomplished in any of a number of ways, including by providing a dominant negative Wnt/β-catenin signaling, Notch signaling or Hedgehog signaling polypeptide, e.g., a form of Wnt/β-catenin signaling, Notch signaling or Hedgehog signaling protein that itself has no activity and which, when present in the same cell as a functional Wnt/β-catenin signaling, Notch signaling or Hedgehog signaling protein, reduces or eliminates the Wnt/β-catenin signaling, Notch signaling or Hedgehog signaling protein activity of the functional Wnt/β-catenin signaling, Notch signaling or Hedgehog signaling protein. Design of dominant negative forms is well known to those of skill and is described, e.g., in Herskowitz, *Nature* 329:219-22, 1987. Also, inactive polypeptide variants (muteins) can be used, e.g., by screening for the ability to inhibit Wnt/β-catenin signaling, Notch signaling or Hedgehog signaling protein activity. Methods of making muteins are well known to those of skill (see, e.g., U.S. Pat. Nos. 5,486,463; 5,422,260; 5,116,943; 4,752,585; and 4,518,504). In addition, any small molecule, e.g., any peptide, amino acid, nucleotide, lipid, carbohydrate, or any other organic or inorganic molecule can be screened for the ability to bind to or inhibit Wnt/β-catenin signaling, Notch signaling or Hedgehog signaling protein activity, as described below.

(E) Modulators and Binding Compounds

The compounds tested as modulators of a Wnt/β-catenin signaling, Notch signaling or Hedgehog signaling protein can be any small chemical compound, or a biological entity, such as a protein, sugar, nucleic acid or lipid. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses)

that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487-493, 1991; and Houghton et al., *Nature* 354: 84-88, 1991). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913, 1993), vinylogous polypeptides (Hagihara et al., *J. Amer. Chem. Soc.* 114:6568, 1992), nonpeptidal peptidomimetics with glucose scaffolding (Hirschmann et al., *J. Amer. Chem. Soc.* 114:9217-9218, 1992), analogous organic syntheses of small compound libraries (Chen et al., *J. Amer. Chem. Soc.* 116:2661, 1994), oligocarbamates (Cho et al., *Science* 261:1303, 1993), and/or peptidyl phosphonates (Campbell et al., *J. Org. Chem.* 59:658, 1994), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology* 14:309-314, 1996; and PCT/US96/10287), carbohydrate libraries (see, e.g., Liang et al., *Science,* 274: 1520-1522, 1996; and U.S. Patent No. 5,593,853), small organic molecule libraries (see, e.g., benzodiazepines, Baum, *C&EN*, page 33, Jan. 18, 1993; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md., etc.).

(F) Solid State and Soluble High Throughput Assays

In one embodiment, the invention provides soluble assays using molecules such as an N-terminal or C-terminal domain either alone or covalently linked to a heterologous protein to create a chimeric molecule. In another embodiment, the invention provides solid phase based iin vitro assays in a high throughput format, where a domain, chimeric molecule, Wnt/ β-catenin signaling, Notch signaling or Hedgehog signaling protein, or cell or tissue expressing a Wnt/β-catenin signaling, Notch signaling or Hedgehog signaling protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154, 1993 (describing solid phase synthesis of, e.g., peptides); Geysen et al., *J. Immun. Meth.* 102:259-274, 1987 (describing synthesis of solid phase components on pins); Frank & Doring, *Tetrahedron* 44:6031-6040, 1988 (describing synthesis of various peptide sequences on cellulose disks); Fodor et al., *Science* 251: 767-777, 1991; Sheldon et al., *Clinical Chemistry* 39:718-719, 1993; and Kozal et al., *Nature Medicine* 2:753-759, 1996 (all describing arrays of biopolymers fixed to solid substrates). Nonchemical approaches for fixing tag binders to substrates include other common methods, such as heat, cross-linking by UV radiation, and the like.

(G) Rational Drug Design Assays

Yet another assay for compounds that modulate Wnt/β-catenin signaling, Notch signaling or Hedgehog signaling protein activity involves computer assisted drug design, in which a computer system is used to generate a three-dimensional structure of a Wnt/β-catenin signaling, Notch signaling or Hedgehog signaling protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding a Wnt/β-catenin signaling, Notch signaling or Hedgehog signaling polypeptide into the computer system. The nucleotide sequence encoding the polypeptide, or the amino acid sequence thereof, and conservatively modified versions thereof, of the naturally occurring gene sequence. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the Wnt/β-catenin signaling, Notch signaling or Hedgehog signaling protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of Wnt/β-catenin signaling, Notch signaling or Hedgehog signaling genes. Such mutations can be associated with disease states or genetic traits. GeneChip™ and related technology can also be used to screen for mutations, polymorphic variants, alleles and interspecies homologs. Once the variants are identified, diagnostic assays can be used to identify patients having such mutated genes. Identification of the mutated Wnt/β-catenin signaling, Notch signaling or Hedgehog signaling genes involves receiving input of a first nucleic acid or amino acid sequence of the naturally occurring Wnt/β-catenin signaling, Notch signaling or Hedgehog signaling induced gene, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various Wnt/β-catenin signaling, Notch signaling or Hedgehog signaling genes, and mutations associated with disease states and genetic traits.

Diagnostic Methods

In addition to assays, the creation of animal models, and nucleic acid based therepeutics, identification of important genes allows the use of these genes in diagnosis (e.g., diagnosis of cell states and abnormal cell conditions). Disorders based on mutant or variant Wnt/β-catenin signaling, Notch signaling or Hedgehog signaling genes can be determined. Methods for identifying cells containing variant Wnt/β-catenin signaling, Notch signaling or Hedgehog signaling genes comprising determining all or part of the sequence of at least one endogeneous genes in a cell are provided. As will be appreciated by those in the art, this can be done using any number of sequencing techniques. Methods of identifying the genotype of an individual comprising determining all or part of the sequence of at least one Wnt/β-catenin signaling, Notch signaling or Hedgehog signaling gene of the individual are also provided. This is generally done in at least one tissue of the individual, and can include the evaluation of a number of tissues or different samples of the same tissue. The method can include comparing the sequence of the sequenced mutant Wnt gene or β-catenin gene to a known Wnt gene or β-catenin gene, i.e., a wild-type gene.

The sequence of all or part of the Wnt/β-catenin signaling, Notch signaling or Hedgehog signaling gene can then be compared to the sequence of a known Wnt/β-catenin signaling, Notch signaling or Hedgehog signaling gene to determine if any differences exist. This can be done using any number of known sequence identity programs, such as Bestfit, and others outlined herein. In some methods, the presence of a difference in the sequence between the Wnt/β-catenin signaling, Notch signaling or Hedgehog signaling gene of the patient and the known Wnt/β-catenin signaling, Notch signaling or Hedgehog signaling gene is indicative of a disease state or a propensity for a disease state, as outlined herein.

Similarly, diagnosis of hematopoietic stem cell or muscle progenitor cell states can be done using the methods and compositions herein. By evaluating the gene expression profile of hematopoietic stem cells or neural progenitor cells, muscle progenitor cells from a patient, the hematopoietic stem cell or muscle progenitor cell state can be determined. This is particularly useful to verify the action of a drug, for example an immunosuppressive drug. Other methods comprise administering the drug to a patient and removing a cell sample, particularly of hematopoietic stem cells or neural progenitor cells, muscle progenitor cells, from the patient. The gene expression profile of the cell is then evaluated, as outlined herein, for example by comparing it to the expression profile from an equivalent sample from a healthy individual. In this manner, both the efficacy (i.e., whether the correct expression profile is being generated from the drug) and the dose (is the dosage correct to result in the correct expression profile) can be verified.

The present discovery relating to the role of Wnt/β-catenin signaling, Notch signaling or Hedgehog signaling in enhancing an immune response, or e.g., treating immune related disease, degenerative muscle disease or neurodegenerative disease in a mammalian subject. In one method, the Wnt/β-catenin signaling, Notch signaling or Hedgehog signaling proteins, and particularly Wnt/β-catenin signaling, Notch signaling or Hedgehog signaling protein fragments, are useful in the study or treatment of conditions which are mediated by various disease states, i.e., to diagnose, treat or prevent immune-mediated disorders. Thus, "immune-mediated disorders" or "disease states" can include conditions involving, for example, inhibition or enhancement of an immune response, autoimmune disease, neoplastic disease, systemic lupus erthymatosus, or allogeneic tissue rejection.

Methods of modulating immune-regulatory states in cells or organisms are provided. Some methods comprise administering to a cell an anti-Wnt signaling promoting protein antibody or anti-β-catenin signal-promoting protein antibody or other agent identified herein or by the methods provided herein, that reduces or eliminates the biological activity of the endogeneous Wnt/β-catenin signaling, Notch signaling or Hedgehog signaling protein. Alternatively, the methods comprise administering to a cell or organism a recombinant nucleic acid encoding a Wnt/β-catenin signal-, Notch signal- or Hedgehog signal-promoting protein or modulator including anti-sense nucleic acids. As will be appreciated by those in the art, this can be accomplished in any number of ways. In some methods, the activity Wnt/β-catenin signaling, Notch signaling or Hedgehog signaling is increased by increasing the amount or activity of Wnt/β-catenin signal-, Notch signal- or Hedgehog signal-promoting protein in the cell, for example by overexpressing the endogeneous Wnt/β-catenin signal-, Notch signal- or Hedgehog signal-promoting protein or by administering a Wnt/β-catenin signal-, Notch signal- or Hedgehog signal-promoting gene, using known gene therapy techniques, for example. In one method, the gene therapy techniques include the incorporation of the exogenous gene using enhanced homologous recombination (EHR), for example as described in PCT/US93/03868, hereby incorporated by reference in its entirety.

Methods for diagnosing a hematopoietic stem cell or muscle progenitor cell activity related condition in an individual are provided. The methods comprise measuring the activity of Wnt/β-catenin signal-, Notch signal- or Hedgehog signal-promoting protein in a tissue from the individual or patient, which can include a measurement of the amount or specific activity of the protein. This activity is compared to the activity of Wnt/β-catenin signal-, Notch signal- or Hedgehog signal-promoting protein from either an unaffected second individual or from an unaffected tissue from the first individual. When these activities are different, the first individual can be at risk for a hematopoietic stem cell or muscle progenitor cell activity mediated disorder.

Furthermore, nucleotide sequences encoding a Wnt/β-catenin signal-, Notch signal- or Hedgehog signal-promoting protein can also be used to construct hybridization probes for mapping the gene which encodes that Wnt/β-catenin signal-, Notch signal- or Hedgehog signal-promoting protein and for the genetic analysis of individuals with genetic disorders. The nucleotide sequences provided herein can be mapped to a chromosome and specific regions of a chromosome using known techniques, such as in situ hybridization, linkage analysis against known chromosomal markers, and hybridization screening with libraries.

Antibodies

"Antibody" is used in the broadest sense and specifically covers polyclonal antibodies, monoclonal antibodies, antibody compositions with polyepitopic specificity, bispecific antibodies, diabodies, and single-chain molecules, as well as antibody fragments (e.g., Fab, F(ab')$_2$, and Fv), so long as they exhibit the desired biological activity. Antibodies can be labeled/conjugated to toxic or non-toxic moieties. Toxic moieties include, for example, bacterial toxins, viral toxins, radioisotopes, and the like. Antibodies can be labeled for use in biological assays (e.g., radioisotope labels, fluorescent labels) to aid in detection of the antibody. Antibodies can also be labeled/conjugated for diagnostic or therapeutic purposes, e.g., with radioactive isotopes that deliver radiation directly to a desired site for applications such as radioimmunotherapy (Garmestani. et al., *Nucl Med Biol,* 28:409, 2001), imaging techniques and radioimmunoguided surgery or labels that allow for iin vivo imaging or detection of specific antibody/antigen complexes. Antibodies can also be conjugated with toxins to provide an immunotoxin (see, Kreitman, *RJ Adv Drug Del Rev,* 31:53, 1998).

"Monoclonal antibody" refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., *Nature,* 256: 495, 1975, or can be made by recombinant DNA methods (see, e.g., U.S. Pat. No. 4,816,567, Cabilly et al.). The "monoclonal antibodies" can also be isolated from phage antibody libraries using the techniques described in Clackson et al., 624-628, 1991, and Marks et al., *J. Mol. Biol.,* 222:581-597, 1991, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. (Cabilly et al., supra; Morrison et al., *Proc. Natl. Acad. Sci. USA*, 81:6851-6855, 1984).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature* 321:522-525, 1986; Reichmann et al., *Nature* 332:323-329, 1988; and Presta, *Curr. Op. Struct. Biol.* 2:593-596, 1992. The humanized antibody includes a Primatized™ antibody wherein the antigen-binding region of the antibody is derived from an antibody produced by immunizing macaque monkeys with the antigen of interest.

Amino acids from the variable regions of the mature heavy and light chains of immunoglobulins are designated Hx and Lx respectively, where x is a number designating the position of an amino acids according to the scheme of Kabat et al., 1987 and 1991, Sequences of Proteins of Immunological Interest (National Institutes of Health, Bethesda, Md). Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody "Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g., 8 to 14 days).

"Neutralizing antibody" refers to an antibody which is able to block or significantly reduce an effector function of wild type or mutant Wnt/β-catenin signal-, Notch signal- or Hedgehog signal-promoting. For example, a neutralizing antibody can inhibit or reduce Wnt, β-catenin, Notch, or Hedgehog activation by an agonist antibody, as determined, for example, in a Wnt/β-catenin signaling, Notch signaling or Hedgehog signaling assay, or other assays taught herein or known in the art.

In some methods, the Wnt/β-catenin signal-, Notch signal- or Hedgehog signal-promoting proteins can be used to generate polyclonal and monoclonal antibodies to Wnt/β-catenin signal-, Notch signal- or Hedgehog signal-promoting proteins, which are useful as described herein. A number of immunogens are used to produce antibodies that specifically bind Wnt/β-catenin signal-, Notch signal- or Hedgehog signal-promoting polypeptides. Full-length Wnt/β-catenin signal-, Notch signal- or Hedgehog signal-promoting polypeptides are suitable immunogens. Typically, the immunogen of interest is a peptide of at least about 3 amino acids, more typically the peptide is at least 5 amino acids in length, the fragment is at least 10 amino acids in length and typically the fragment is at least 15 amino acids in length. The peptides can be coupled to a carrier protein (e.g., as a fusion protein), or are recombinantly expressed in an immunization vector. Antigenic determinants on peptides to which antibodies bind are typically 3 to 10 amino acids in length. Naturally occurring polypeptides are also used either in pure or impure form. Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

These antibodies find use in a number of applications. For example, the Wnt/β-catenin signal-, Notch signal- or Hedgehog signal-promoting antibodies can be coupled to standard affinity chromatography columns and used to purify Wnt/β-catenin signal-, Notch signal- or Hedgehog signal-promoting proteins as further described below. The antibodies can also be used as blocking polypeptides, as outlined above, since they will specifically bind to the Wnt/β-catenin signal-, Notch signal- or Hedgehog signal-promoting protein.

The anti-Wnt protein or anti-β-catenin protein antibodies can comprise polyclonal antibodies. Methods for producing polyclonal antibodies are known to those of skill in the art. In brief, an immunogen, for example, a purified polypeptide, a polypeptide coupled to an appropriate carrier (e.g., GST and keyhole limpet hemocyanin), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan, *Current Protocols in Immunology*, Wiley/Greene, NY, 1991; and Harlow and Lane, supra, each incorporated herein by reference in their entirety.

Antibodies, including binding fragments and single chain recombinant versions thereof, against predetermined fragments of Wnt/β-catenin signal-, Notch signal- or Hedgehog signal-promoting proteins are raised by immunizing animals, e.g., with conjugates of the fragments with carrier proteins as described above.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, allogeneic tissue rejection, or, in cases of autoimmunity or pathological inflammation, normal human cells or tissues.

Other suitable techniques involve selection of libraries of recombinant antibodies in phage or similar vectors, for example, single chain Fv (scFv) libraries. See, Huse et al., *Science* 246:1275-1281, 1989; and Ward, et al., *Nature* 341: 544-546, 1989, each incorporated herein by reference in their entirety.

The protocol described by Huse is rendered more efficient in combination with phage-display technology. See, e.g., Dower et al., WO 91/17271; McCafferty et al., WO 92/01047; and U.S. Pat. Nos. 5,871,907; 5,858,657; 5,837,242; 5,733,743; and 5,565,332, each incorporated herein by reference in their entirety. In these methods, libraries of phage are produced in which members (display packages) display different antibodies on their outer surfaces. Antibodies are usually displayed as Fv or Fab fragments. Phage displaying antibodies with a desired specificity can be selected by affinity enrichment to the antigen or fragment thereof. Phage display combined with immunized transgenic non-human animals expressing human immunoglobulin genes can be used to obtain antigen specific antibodies even when the immune response to the antigen is weak.

Also, recombinant immunoglobulins can be produced. See, U.S. Pat. No. 4,816,567; and Queen et al., *Proc. Natl Acad. Sci. USA* 86:10029-10033, 1989, each incorporated herein by reference in their entirety.

Briefly, nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host useful for expressing antibodies. Other microbial hosts suitable for use include bacilli, such as Bacillus subtilus, and other enterobacteriaceae, such as *Salmonella, Serratia*, and various *Pseudomonas* species. In these procaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, can also be used for expression. *Saccharomyces* is one host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies (See Winnacker, *From Genes to Clones*, VCH Publishers, N.Y., 1987, incorporated herein by reference in its entirety). Eukaryotic cells are useful because a number of suitable host cell lines capable of secreting intact antibodies have been developed. Suitable host cells for expressing nucleic acids encoding the immunoglobulins include: monkey kidney CV1 line transformed by SV40 (COS-7, ATCC CRL 1651); human embryonic kidney line (293) (Graham et al., *J. Gen. Virol.* 36:59, 197-7); baby hamster kidney cells (BHK, ATCC CCL 10); Chinese hamster ovary-cells-DHFR (CHO, Urlaub and Chasin, *Proc. Natl. Acad. Sci. U.S.A.* 77:4216, 1980); mouse sertoli cells (TM4, Mather, *Biol. Reprod.* 23:243-251, 1980); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., *Annals N.Y. Acad. Sci.* 383:44-46, 1982); baculovirus cells. Each citation is incorporated herein by reference in their entirety The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. See generally Sambrook et al., *Molecular Cloning: A Laboratory Manual*, Cold Spring Harbor Press, 2d ed., 1989, incorporated herein by reference in its entirety.

Once expressed, the whole antibodies, their dimers, individual light and heavy chains, or other immunoglobulin forms can be purified according to standard procedures of the art, including ammonium sulfate precipitation, affinity columns, column chromatography, gel electrophoresis and the like. See generally Scopes, *Protein Purification*, Springer-Verlag, N.Y., 1982, incorporated herein by reference in its entirety. Substantially pure immunoglobulins are of at least about 90 to 95% homogeneity, and are typically 98 to 99% homogeneity or more.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Thus, an antibody used for detecting an analyte can be directly labeled with a detectable moiety, or can be indirectly labeled by, for example, binding to the antibody a secondary antibody that is, itself directly or indirectly labeled.

Antibodies are also used for affinity chromatography in isolating Wnt/β-catenin signal-, Notch signal- or Hedgehog signal-promoting proteins. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified Wnt/β-catenin signal-, Notch signal- or Hedgehog signal-promoting polypeptides are released.

Effective Dosages

Effective doses of a composition of Wnt/β-catenin signal-, Notch signal- or Hedgehog signal-promoting agent for the treatment of disease, e.g., immune related disease, degenerative muscle disease or neurodegenerative disease, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with a Wnt/β-catenin signal-, Notch signal- or Hedgehog signal-promoting agent, the dosage ranges from about 0.0001 to 100 mg/kg, and more usually 0.01 to 5 mg/kg, of the host body weight. For example dosages can be 1 mg/kg body weight, 10 mg/kg body weight or 30 mg/kg body weight, or within the range of 1-30 mg/kg body weight. An exemplary treatment dosage with a GSK-3 inhibitor is 30mg/kg body weight. An exemplary treatment regime entails administration once per every two weeks or once a month or once every 3 to 6 months. In some methods, two or more Wnt/β-catenin signal-, Notch signal- or Hedgehog signal-promoting agents are administered simultaneously, in which case the dosage of each Wnt/β-catenin signal-, Notch signal- or Hedgehog signal-promoting agent administered falls within the ranges indicated. Multiple administrations of Wnt/β-catenin signal-, Notch signal- or Hedgehog signal-promoting agent can occur. Intervals between single dosages can be weekly, monthly or yearly. Intervals can also be irregular as indicated by measuring blood levels of the Wnt/β-catenin signal-, Notch signal- or Hedgehog signal-promoting agent in the patient. In some methods, dosage is adjusted to achieve a plasma enriched Wnt/β-catenin signal-, Notch signal- or Hedgehog signal-promoting agent of 1-1000 µg/ml and in some methods 25-300 µg/ml. Alternatively, a Wnt/β-catenin signal-, Notch signal- or Hedgehog signal-promoting agent can be administered as a sustained release formulation, in which case less frequent administration is required. Dosage and frequency vary depending on the half-life of the Wnt/β-catenin signal-, Notch signal- or Hedgehog signal-promoting agent in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Compositions of a Wnt/β-catenin signal-, Notch signal- or Hedgehog signal-promoting agent for the treatment of disease, e.g., immune related disease, degenerative muscle disease or neurodegenerative disease, can be administered by intravesicular, intrathecal, parenteral, topical, intravenous, oral, inhalants, subcutaneous, intraarterial, intracranial, intraperitoneal, intranasal or intramuscular means. As a prophylactic/adjuvant or for treatment of disease, Wnt/β-catenin signal-, Notch signal- or Hedgehog signal-promoting agents target an immune related disease, diabetes, graft vs. host disease, immunodeficiency disease, hematopoietic malignancy, hematopoietic failure, hematopoietic stem cell transplantation, or a muscle degenerative disease and/or therapeutic treatment. The most typical route of administration of an immunogenic agent is subcutaneous or intravenous although other routes can be equally effective. The next most common route is intramuscular injection. This type of injection is most typically performed in the arm or leg muscles. In some methods, agents are injected directly into a particular tissue where deposits have accumulated, for example injection into the bone marrow. Intramuscular injection on intravenous infusion are preferred for administration of a Wnt/β-catenin signal-, Notch signal- or Hedgehog signal-promoting agent.

Agents of the invention can optionally be administered in combination with other agents that are at least partly effective in treating various diseases including immune related disease, degenerative muscle disease or neurodegenerative disease.

Formulation

Compositions of a Wnt/β-catenin signal-, Notch signal- or Hedgehog signal-promoting agent for the treatment of disease, e.g., immune related disease, degenerative muscle disease or neurodegenerative disease.

Compositions of a Wnt/β-catenin signal-, Notch signal- or Hedgehog signal-promoting agent for the treatment of disease, e.g., immune related disease, degenerative muscle disease or neurodegenerative disease, are often administered as pharmaceutical compositions comprising an active therapeutic agent, i.e., and a variety of other pharmaceutically acceptable components. See, e.g., Alfonso R Gennaro (ed), *Remington: The Science and Practice of Pharmacy*, (Formerly Remington's Pharmaceutical Sciences) 20th ed., Lippincott, Williams & Wilkins, 2003, incorporated herein by reference in its entirety. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Wnt/β-catenin signal-, Notch signal- or Hedgehog signal-promoting agent can be administered in the form of a depot injection or implant preparation which can be formulated in such a manner as to permit a sustained release of the active ingredient. An exemplary composition comprises an Wnt/β-catenin signal-, Notch signal- or Hedgehog signal-promoting agent at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science, 249: 1527, 1990; Hanes, *Advanced Drug Delivery Reviews,* 28: 97-119, 1997, incorporated herein by reference in their entirety. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn, et al., *Nature,* 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul, et al., *Eur. J. Immunol.,* 25: 3521-24, 1995; Cevc, et al., *Biochem. Biophys. Acta.,* 1368: 201-15, 1998, incorporated herein by reference in their entirety.

The pharmaceutical compositions generally comprise a composition of the enriched Wnt/β-catenin signal-, Notch signal- or Hedgehog signal-promoting agent in a form suitable for administration to a patient. The pharmaceutical compositions are generally formulated as sterile, substantially isotonic and in full compliance with all Good Manufacturing Practice (GMP) regulations of the U.S. Food and Drug Administration.

Toxicity

Preferably, a therapeutically effective dose of a composition of the Wnt/β-catenin signal-, Notch signal- or Hedgehog signal-promoting agent described herein will provide therapeutic benefit without causing substantial toxicity.

Toxicity of the Wnt/β-catenin signal-, Notch signal- or Hedgehog signal-promoting agent described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the Wnt/β-catenin signal-, Notch signal- or Hedgehog signal-promoting agent described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl, et al., *The Pharmacological Basis Of Therapeutics,* Ch. 1, 1975), incorporated herein by reference in its entirety.

Kits

Also within the scope of the invention are kits comprising the compositions (e.g., a Wnt/β-catenin signal-, Notch signal- or Hedgehog signal-promoting agent) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

Other embodiments and uses will be apparent to one skilled in the art in light of the present disclosures.

EXEMPLARY EMBODIMENTS

EXAMPLE 1

Figure 1B:
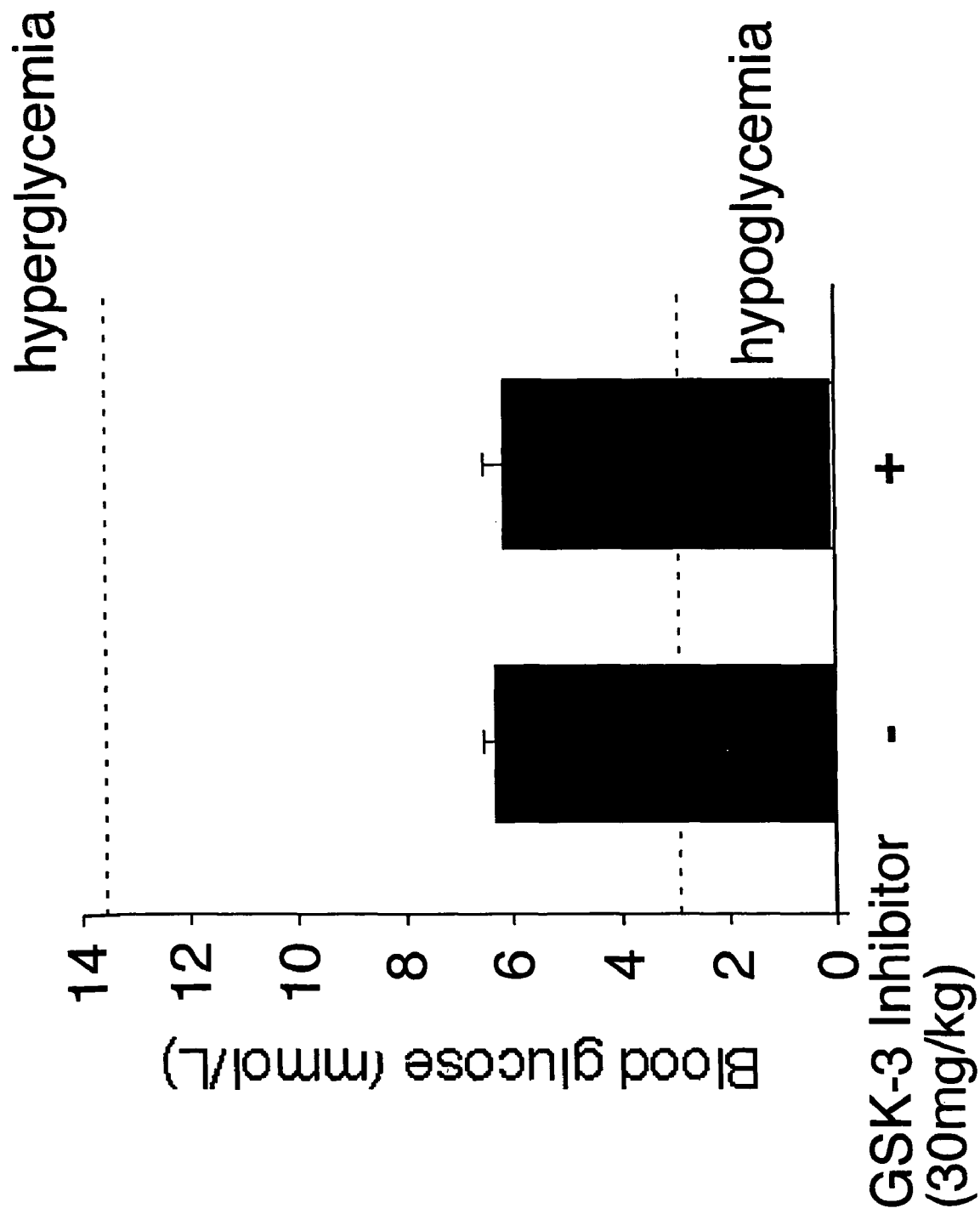

Administration of GSK-3 Inhibitor to HSC Transplanted Recipients Augments Donor HSC Function In Vivo HSCs possess multi-lineage hematopoietic in vivo repopulation capacity upon intravenous transplant into recipient mice. Morrison and Weissman, *Immunity* 1:661-73, 1994. As illustrated in FIG. 1*a*, HSCs were isolated from wild-type GFP/FVB mice, and transplanted into recipient mice treated with or without GSK-3 inhibitor, and HSC activity was evaluated by donor (GFP+) multilineage repopulation of recipients. As in vivo administration of GSK-3 inhibitor (CHIR-911) has been demonstrated to enhance glucose disposal in rodent models of type 2 diabetes, an optimized dose of 30 mg/kg of GSK-3 inhibitor was identified to allow peripheral tissue distribution of the inhibitor, while maintaining a normoglycemic state in transplanted recipients (FIG. 1*b*). Ring et al., *Diabetes* 52:588-595, 2003; Cline et al., *Diabetes* 51:2903-2910, 2002.

Figure 1C:
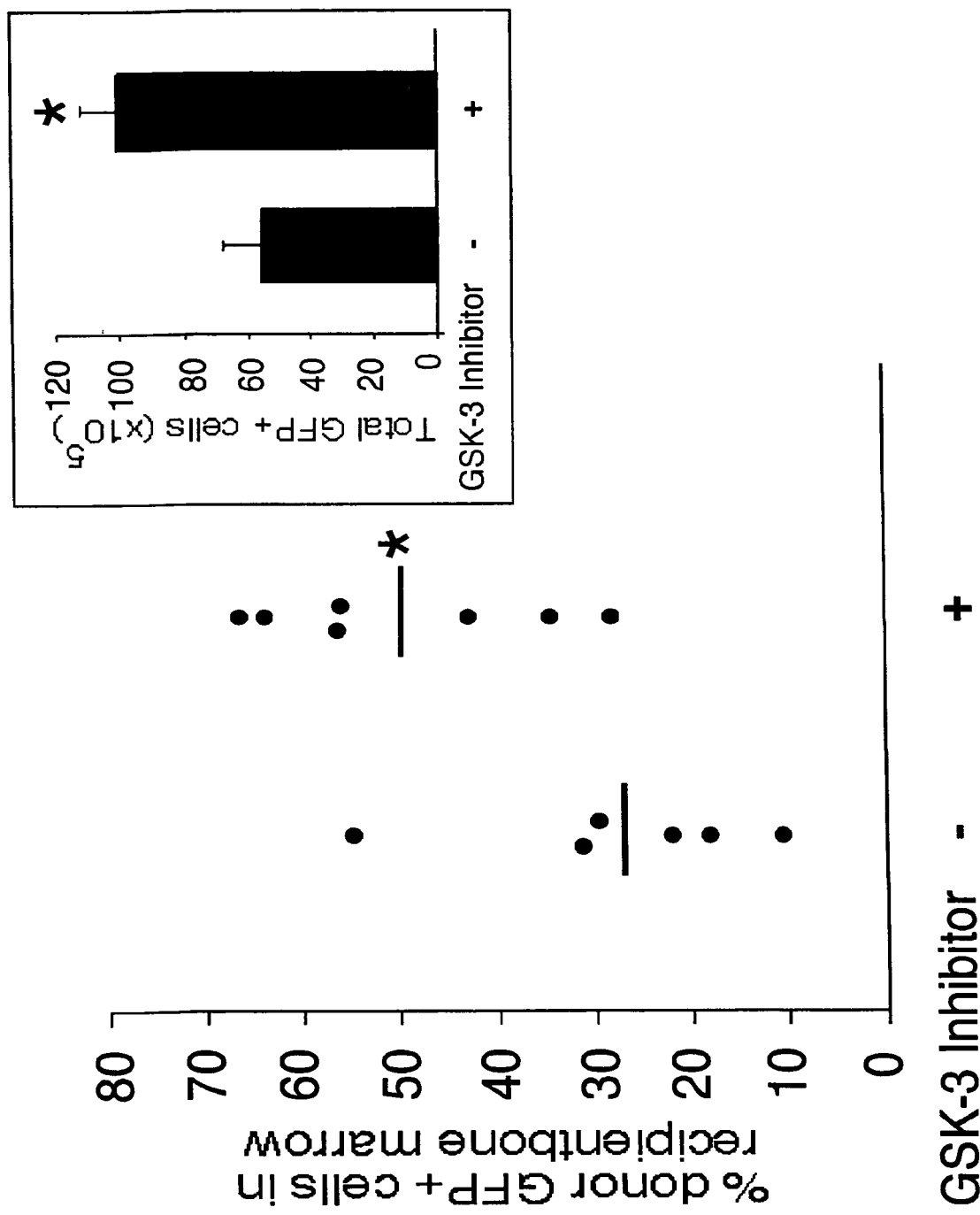
Figure 1D:
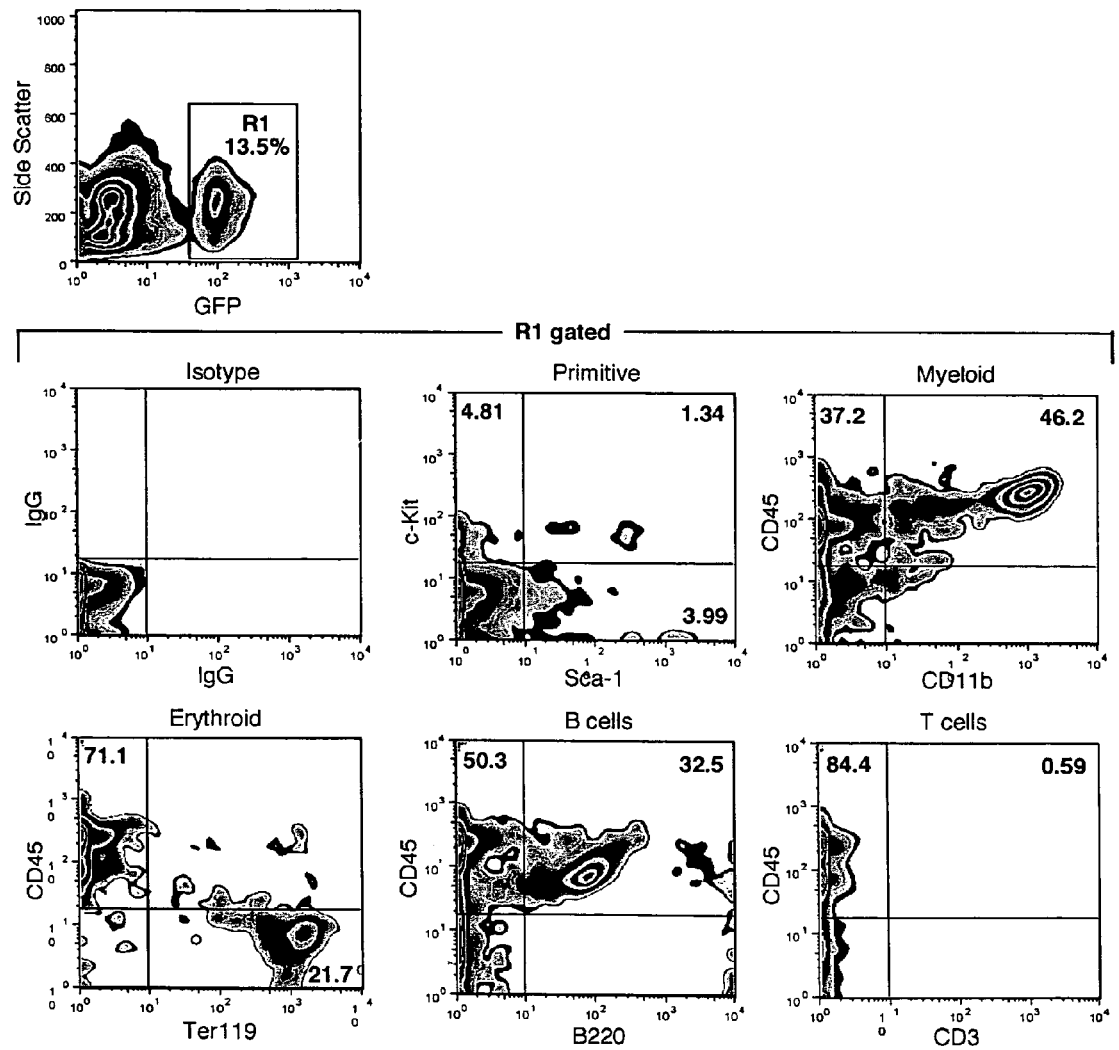
Figure 1E:
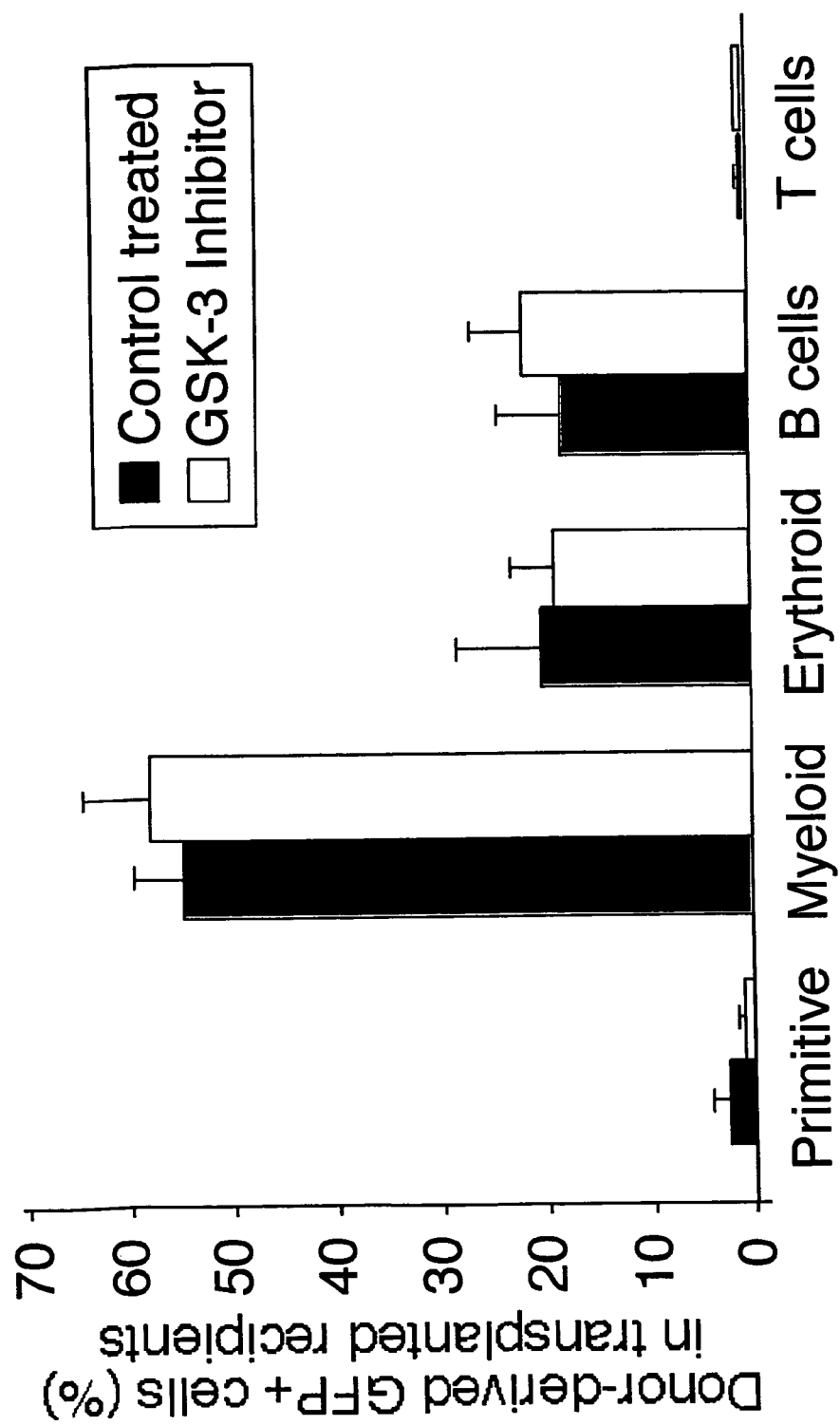

Functional capacity of donor HSC repopulation was increased by more than 22.5% in mice treated with GSK-3 inhibitor (FIG. 1*c*). The total number of donor GFP+ cells in recipient mice was also greater following administration of GSK-3 inhibitor in vivo (FIG. 1*c*, inset), indicative of robust enhancement of HSC proliferative reconstitution. Donor-derived GFP+ cells resulting from transplanted HSCs (FIG. 1*d*, gated R1) were examined by flow cytometry for surface markers representing primitive (c-Kit+Sca-1+), myeloid (CD45+CD11b+), erythroid (CD45-Ter119+), B cell (CD45+B220+), and T cell (CD45+CD3+) lineages indicating multilineage donor HSC reconstitution. Recipients treated with or without GSK-3 inhibitor contained similar multilineage donor-derived cells indicative of HSC function (FIG. 1d, representative). The developmental program of HSCs was not affected by GSK-3 inhibitor, as observed by the similar frequency of reconstituting cell types in GSK-3 inhibitor treated mice compared to control treated recipients (FIG. 1e). These results demonstrate that in vivo administration of GSK-3 inhibitor to HSC transplanted recipients is capable of robust augmentation of transplanted HSC function.

FIG. 1 shows that in vivo administration of GSK-3 inhibitor augments wild type HSC repopulating capacity. (a) Schematic illustration of experimental design to test effects of in vivo administration of GSK-3 inhibitor CHIR-911 on the multilineage repopulating capacity of GFP/FVB HSCs in recipient mice. (b) Blood glucose levels in peripheral blood of recipient mice following 5-week in vivo administration of 30 mg/kg GSK-3 inhibitor or vehicle control. Error bars represent SEM (n=6). (c) Percentage of GFP+ donor-derived cells in the bone marrow of recipient mice treated in vivo with GSK-3 inhibitor or vehicle control. Each symbol (●) represents the percentage of donor-derived cells in a single transplanted mouse. Horizontal lines represent average level of HSC repopulation for each treatment (n=7)*p<0.05. (d) Representative analysis of multilineage differentiation of GFP+ HSCs. Repopulating donor-derived GFP+ cells were gated (R1) and analyzed for presence of surface markers representing primitive (c-kit+sca-1+), myeloid (CD45+CD11b+), erythroid (CD45-Ter119+), B cell (CD45+B220+), and T cell (CD45+CD3+) lineages. (e) Average frequency of donor-derived GFP+ primitive, myeloid, erythroid, B cells and T cells in recipient mice after in vivo administration of GSK-3 inhibitor or vehicle control. Error bars represent SEM (n=6).

EXAMPLE 2

Administration of GSK-3 Inhibitor Increases Human Neonatal and Adult HSC Capacity In Vivo Effects of GSK-3 inhibitor on human HSCs were examined utilizing an established pre-clinical in vivo model of human HSC function. Intravenous transplantation of a unique subset of primitive human hematopoietic cells has been shown to repopulate and sustain human hematopoietic reconstitution in the bone marrow of immune deficient NOD/SCID recipient mice. This reconstituting population of human hematopoietic cells is operationally defined as Scid-Repopulating Cells (SRCs), and accordingly represents candidate human HSCs. Larochelle et al., Nat Med 2:1329-37, 1996; Bhatia et al., Proc Natl Acad Sci USA 94:5320-5325, 1997; Bhatia et al., Nat Med 4:1038-45, 1998.

Figure 2A:
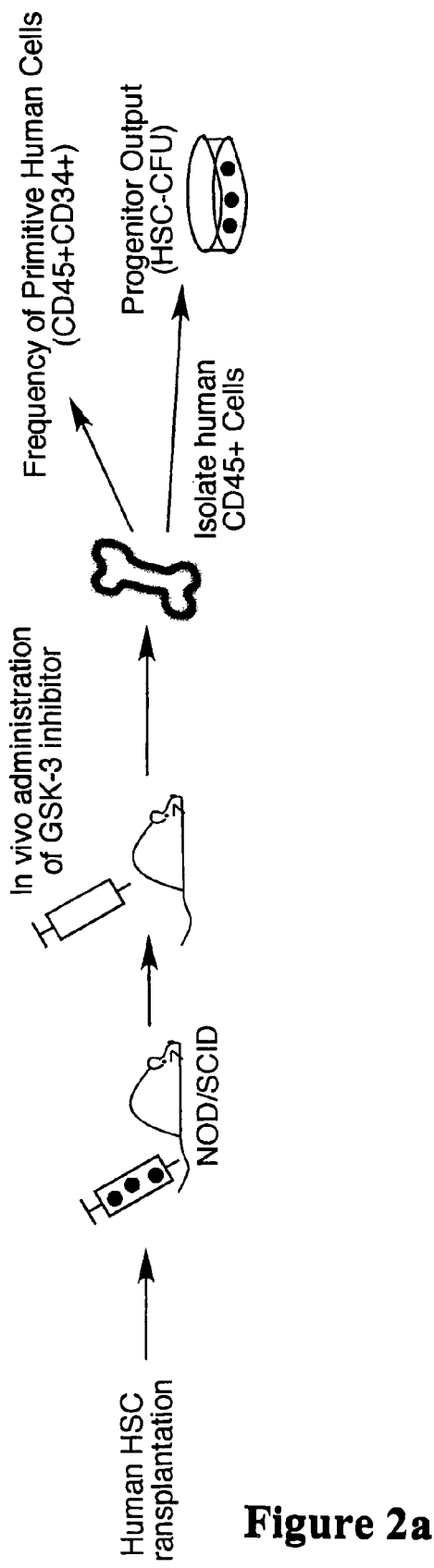
FIGS. 2a, 2b, 2c, 2d, and 2e show that in vivo administration of GSK-3 inhibitor augments human neonatal and adult HSC capacity.
Figure 2B:
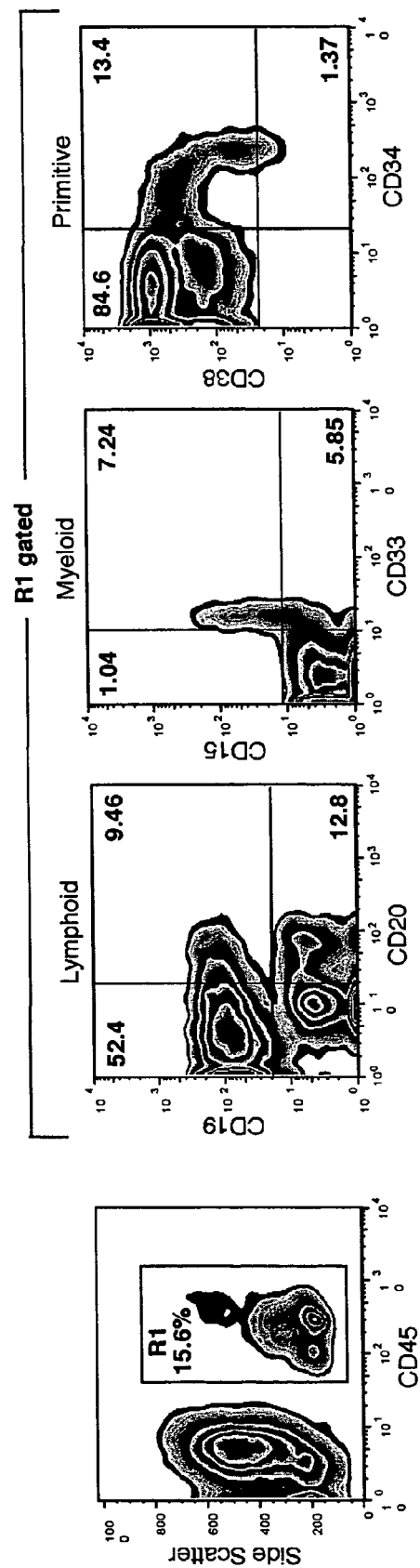

Primitive lineage-depleted (Lin-) neonatal umbilical cord blood (CB) cells, or adult mobilized peripheral blood (M-PB) mononuclear cells, were transplanted into sublethally irradiated recipients administered 30 mg/kg GSK-3 inhibitor or vehicle (FIG. 2a). Human multilineage repopulating capacity of transplanted HSCs was examined by flow cytometry for surface markers representing human lymphoid (CD19, CD20), myeloid (CD15, CD33), and primitive (CD34, CD38), hematopoietic subsets. All reconstituted recipients were found to contain multilineage human donor-derived cells indicative of human HSC function (FIG. 2b).

Figure 2C:
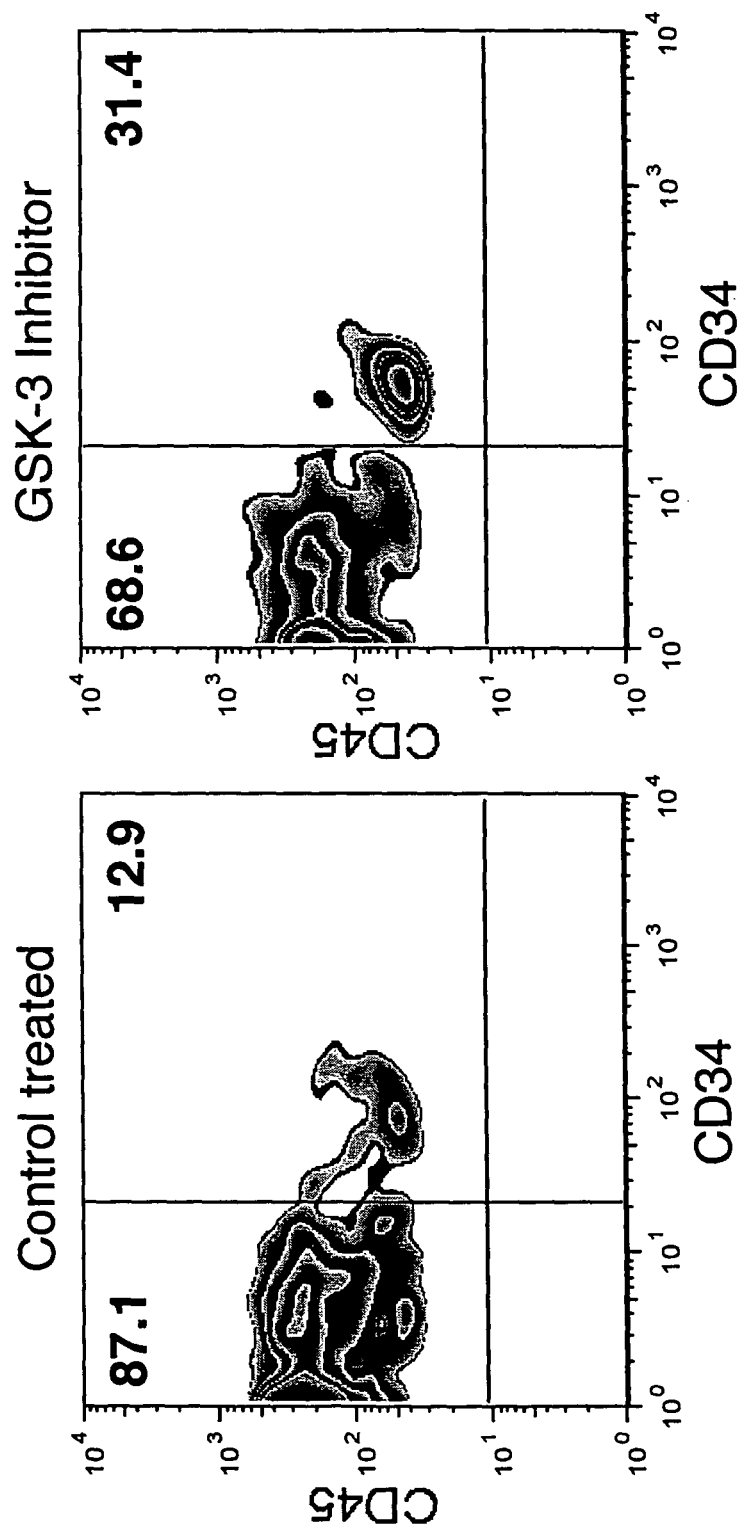
Figure 2D:
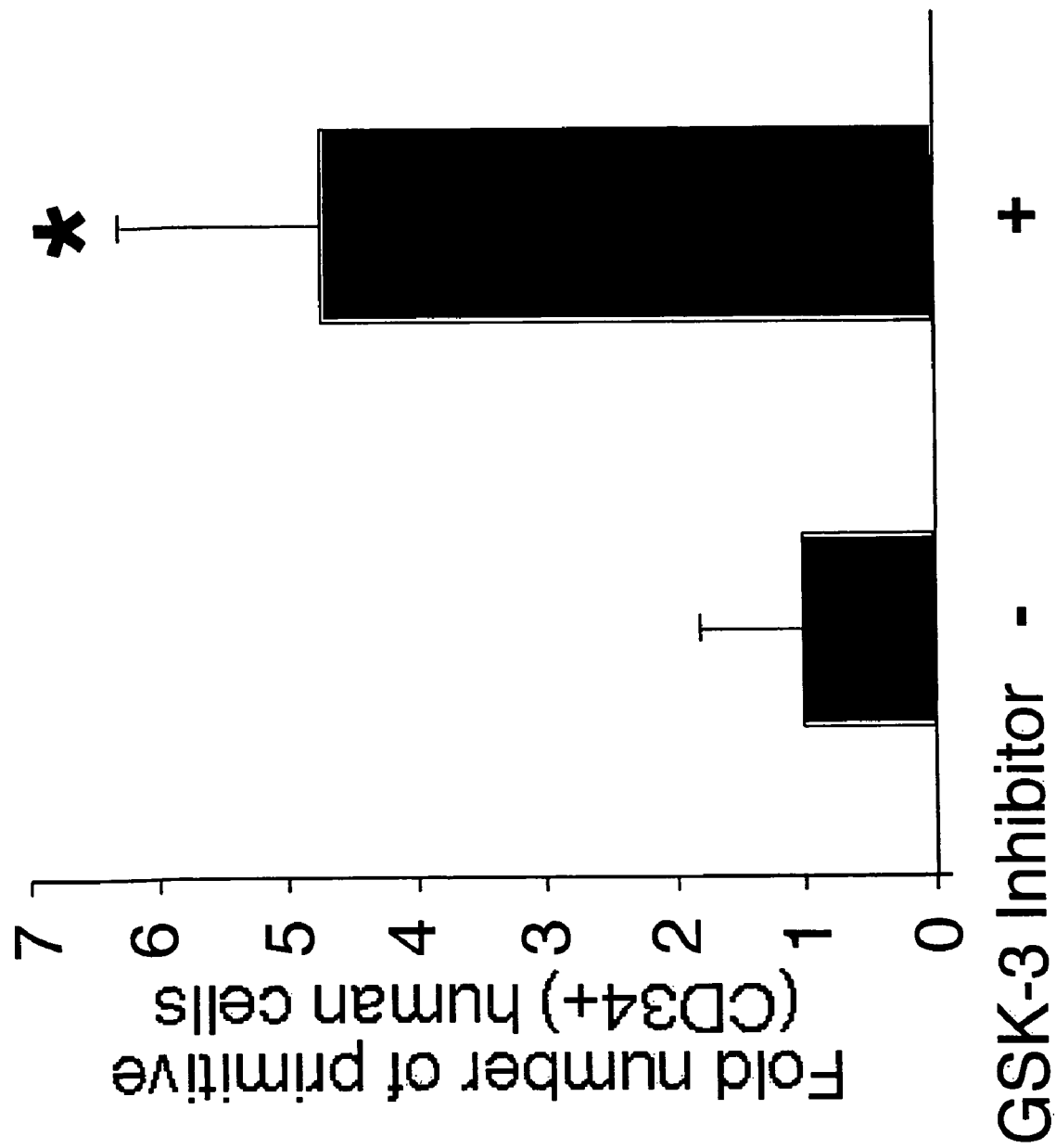
Figure 2E:
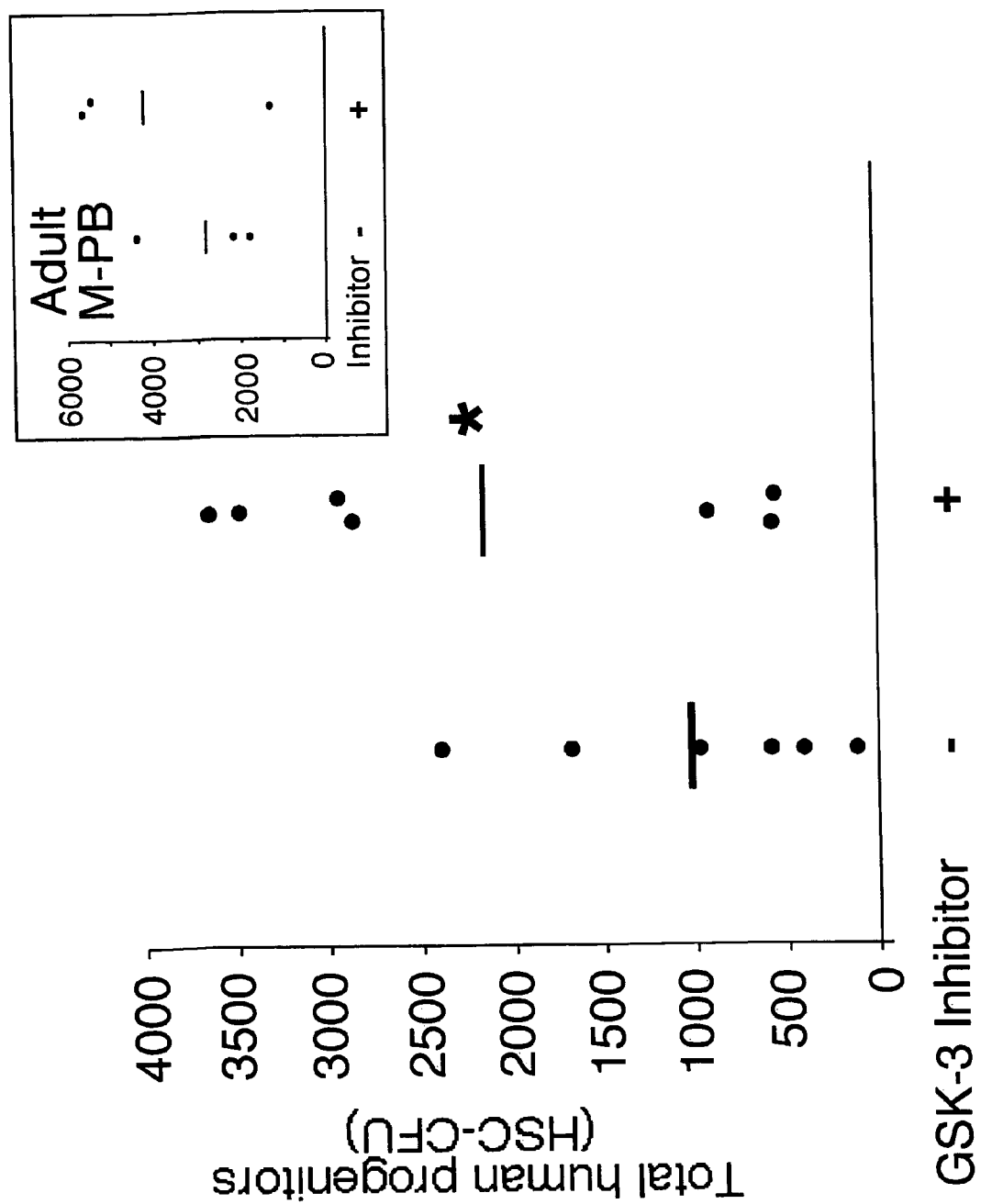

Administration of GSK-3 inhibitor increased the frequency (FIG. 2c) and total number (FIG. 2d) of primitive human hematopoietic cells (CD45+CD34+) from CB-HSCs compared to control treated recipients, indicating that in vivo human HSC capacity was augmented by GSK-3 inhibitor. To further characterize the effect of GSK-3 on primitive human HSC capacity, progenitor potential was determined using functional clonogenic assays of human hematopoietic colony-forming units (CFU) derived from HSCs (HSC-CFU). Murdoch et al., PNAS 100:3422-3427, 2003. Using fluorescence-activated cell sorting (FACS), human CD45+ hematopoietic cells were isolated from human reconstituted recipient NOD/SCID mice treated with or without GSK-3 inhibitor to quantitate HSC-CFU potential. Both human CB-HSC and M-PB-HSC donor-derived cells isolated from GSK-3 inhibitor treated recipients gave rise to greater numbers of HSC-CFUs (FIG. 2e). Developmental potential of HSC-CFU progenitors (based on subtype analysis of erythroid, granulocyte, macrophage, granulocyte-macrophage colonies) was not altered by GSK-3 inhibitor treatment (data not shown). Combined with effects of GSK-3 inhibitor on reconstituting mouse HSCs (FIG. 1), these data indicate that GSK-3 is a potent regulator of transplanted mammalian HSCs.

FIG. 2 shows that in vivo administration of GSK-3 inhibitor augments human neonatal and adult HSC capacity. (a) Schematic illustration of experimental design to test effects of in vivo administration of GSK-3 inhibitor on the frequency of human hematopoietic progenitor cells and progenitor function after repopulation of human neonatal umbilical cord blood (CB), or adult mobilized peripheral blood (MPB) HSCs in recipient mice. (b) Representative analysis of multilineage human CB-derived hematopoietic repopulation in recipient mice. Repopulating human CD45+ cells were gated (R1) and analyzed for the presence of B cells (CD19,CD20), myeloid (CD15,CD33), and primitive (CD34,CD38) lineages. (c) Representative analysis of the frequency of CD34+ cells within the human CB CD45+ donor-derived graft. (d) Average number of human CB-derived progenitors (CD34+) in recipient mice following in vivo administration of GSK-3 inhibitor or vehicle control. *p<0.05. Error bars represent SEM (n=4). (e) Total human progenitors (CFU) isolated from CB-derived or MPB-derived (inset) reconstituting HSCs after in vivo treatment with GSK-3 inhibitor or vehicle control. Each symbol (●) represents CFU capacity of human cells isolated from a single transplanted mouse. Horizontal lines represent average level of engraftment for each recipient. *p<0.05, n=7.

EXAMPLE 3

Figure 3A:
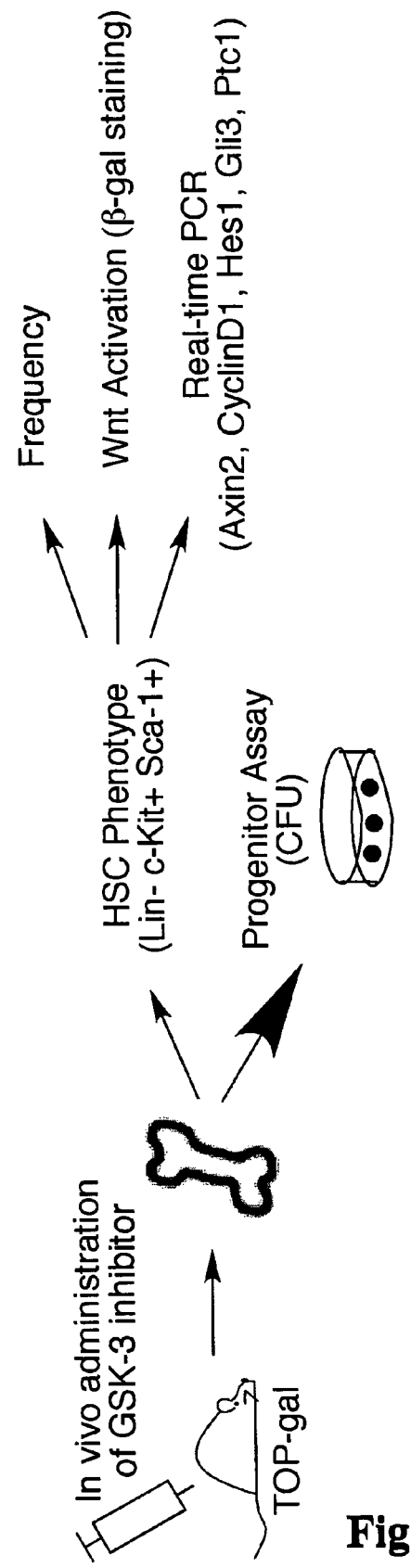
FIGS. 3a, 3b, 3c, 3d, 3e, 3f, 3g, and 3h show that in vivo administration of GSK-3 inhibitor to TOP-gal mice enhances HSC activity and regulates targets of the Wnt, Notch and Hedgehog pathways.
Figure 3B:
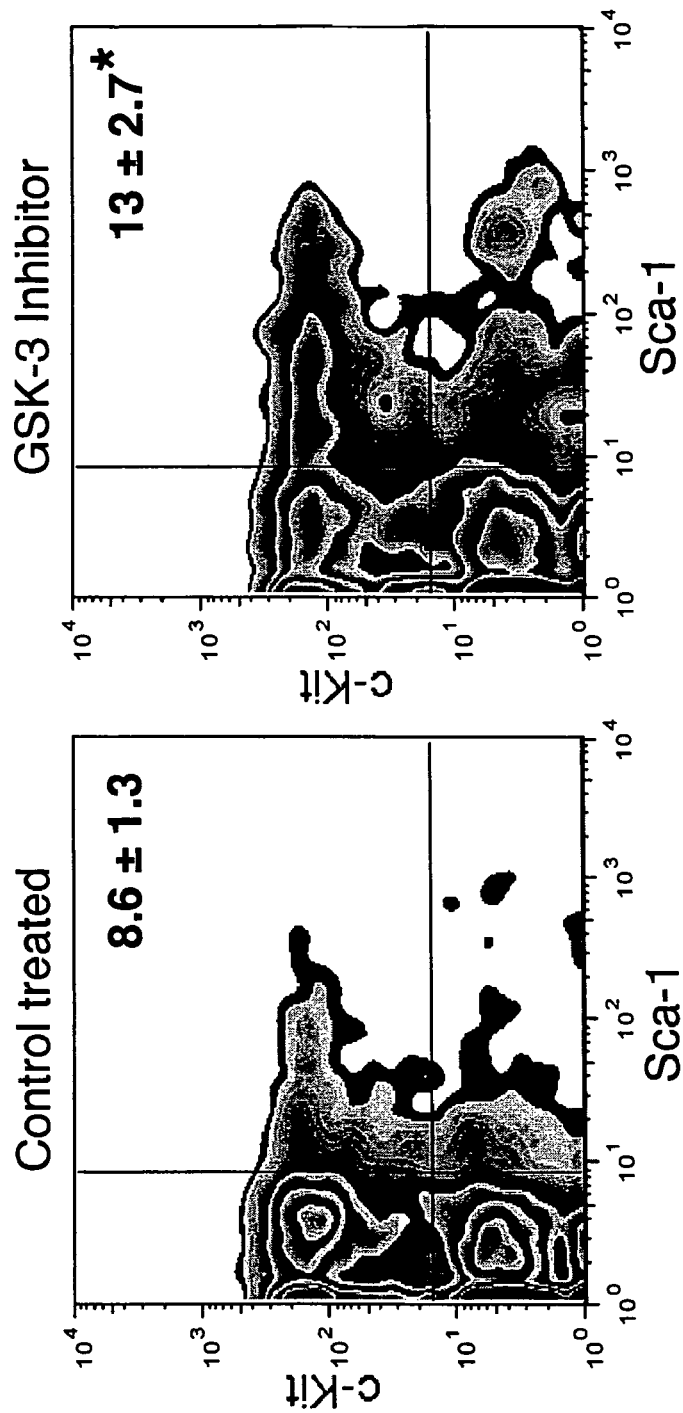
Figure 3C:
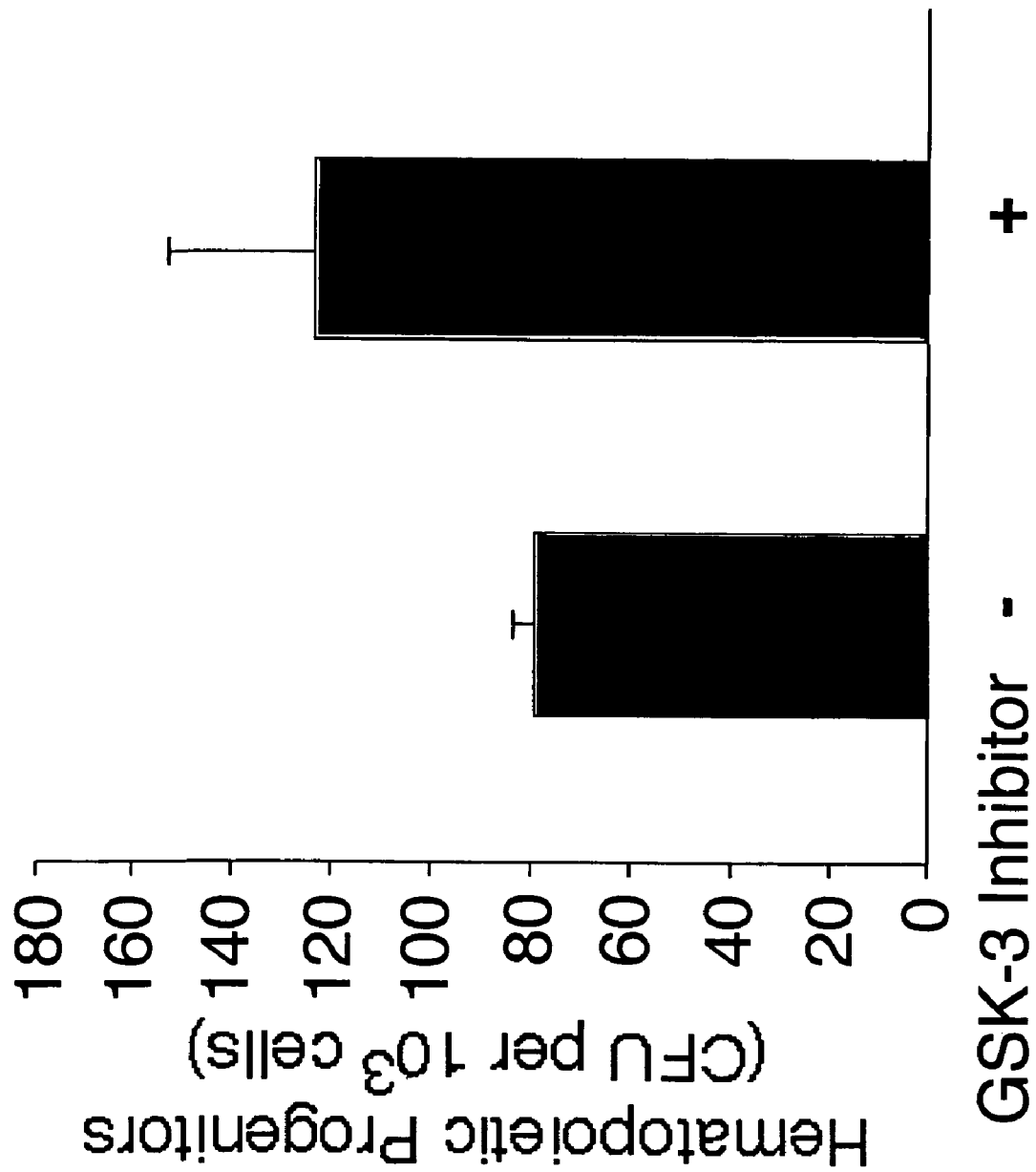

GSK-3 Inhibitor Increases HSC Frequency and Function, and Specifically Modulates Wnt, Hedgehog, and Notch Pathways of HSCs in vivo GSK-3 has been shown to be involved in the Wnt signaling pathway, and has been shown to affect human and mouse HSCs. Behrens et al., Science 280:596-599, 1998; Yost et al., Genes Dev 10:1443-1454, 1996; Murdoch et al., PNAS 100: 3422-3427, 2003; Reya et al., Nature 423:409-14, 2003. Using transgenic mice with a LEF-1/TCF promoter ("TCF optimal promoter") driving expression of β-galactosidase (TOP-gal), the effects of in vivo administration of GSK-3 inhibitor on HSC frequency and function were examined, and impact on the Wnt pathway was examined. DasGupta and Fuchs, Development 126:4557-4568, 1999. Transgenic TOP-gal mice treated 3 times every 12 hours with 30 mg/kg GSK-3 inhibitor demonstrated an increase in the frequency of HSCs (Lin-c-Kit+Sca-1+), compared to control treatment (FIG. 3b). Uchida and Weissman, J Exp Med 175:175-84, 1992. Furthermore, primitive (Lin-) bone marrow cells isolated from GSK-3 inhibitor treated TOP-gal mice revealed a greater than 50% increase in clonogenic progenitor capacity (CFU), as compared to control treated animals (FIG. 3c). These observations indicate that the effect of GSK-3 inhibitor administration in vivo is not limited to transplanted HSCs, but is also capable of directly affecting HSC function in non-ablated hosts where HSCs remain in their native bone marrow environment.

Figure 3D:
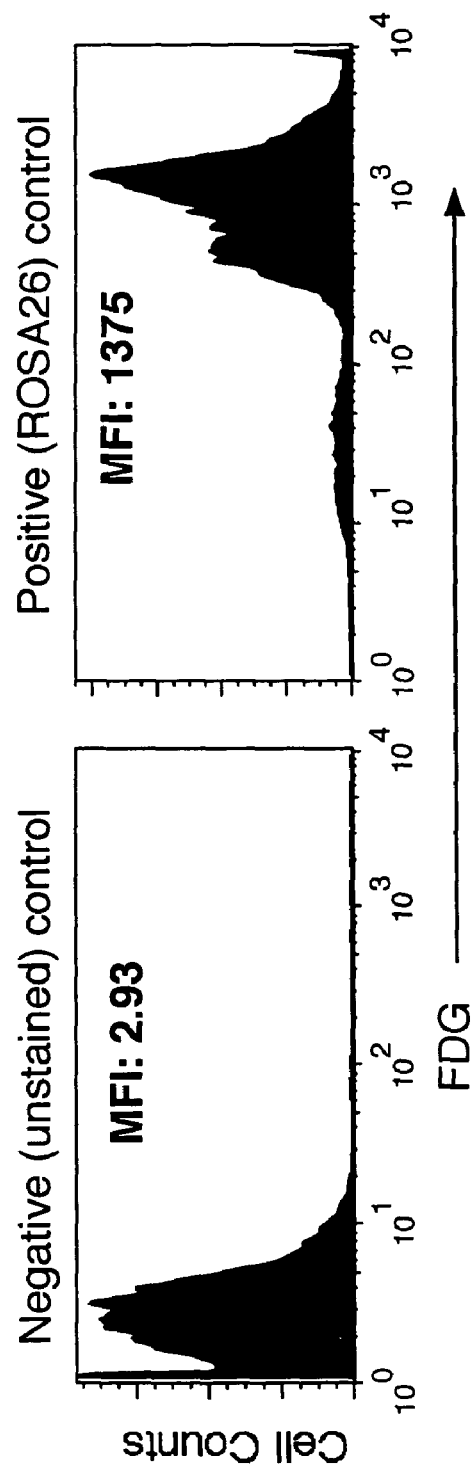
Figure 3E:
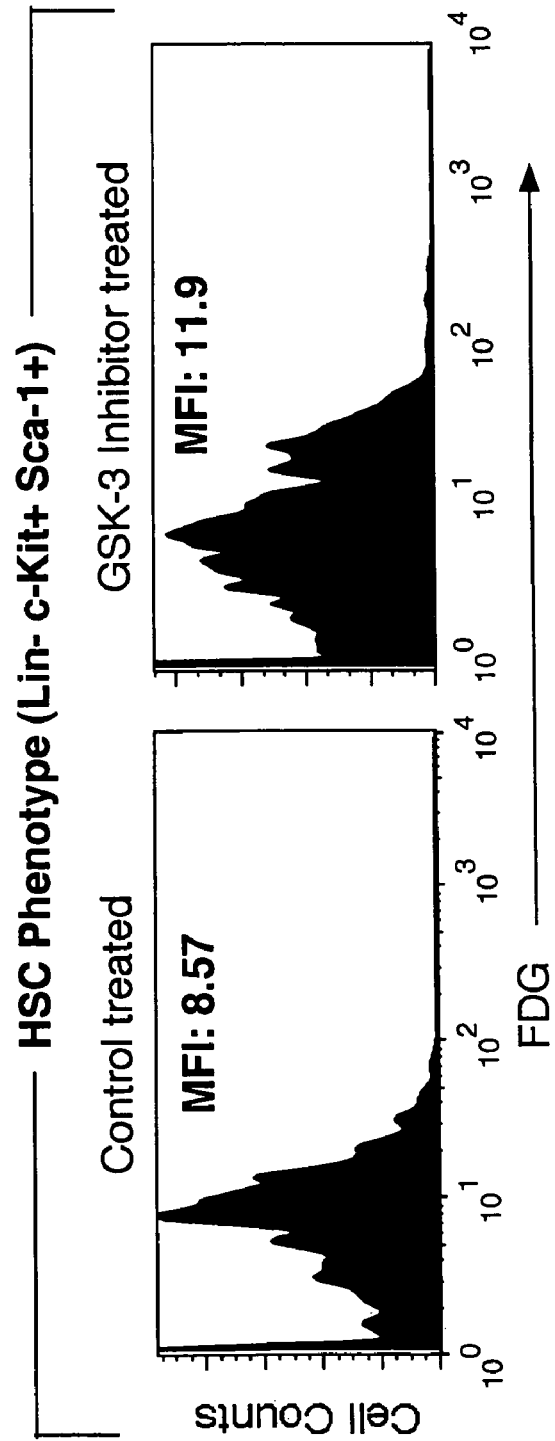
Figure 3F:
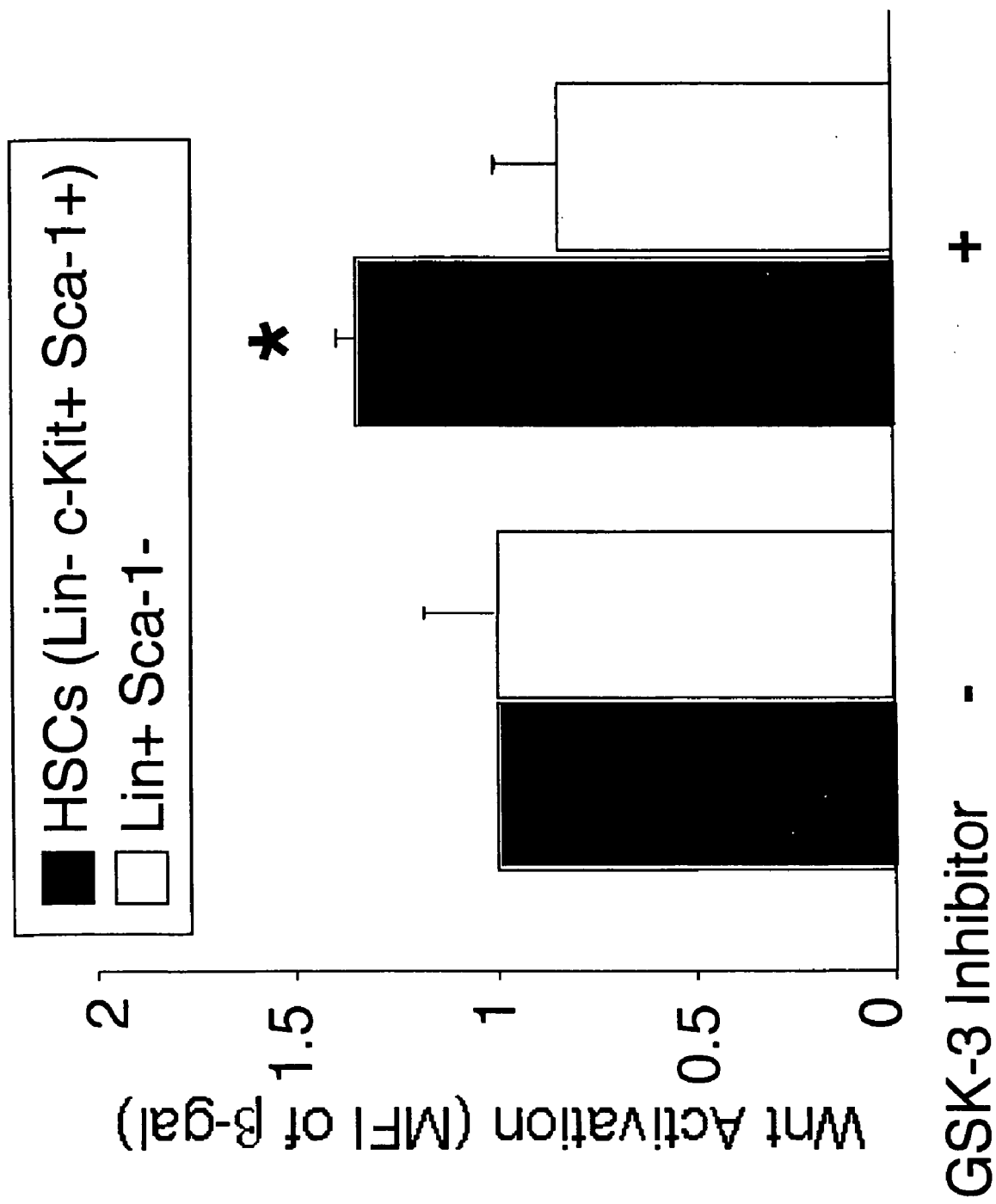
Figure 3G:
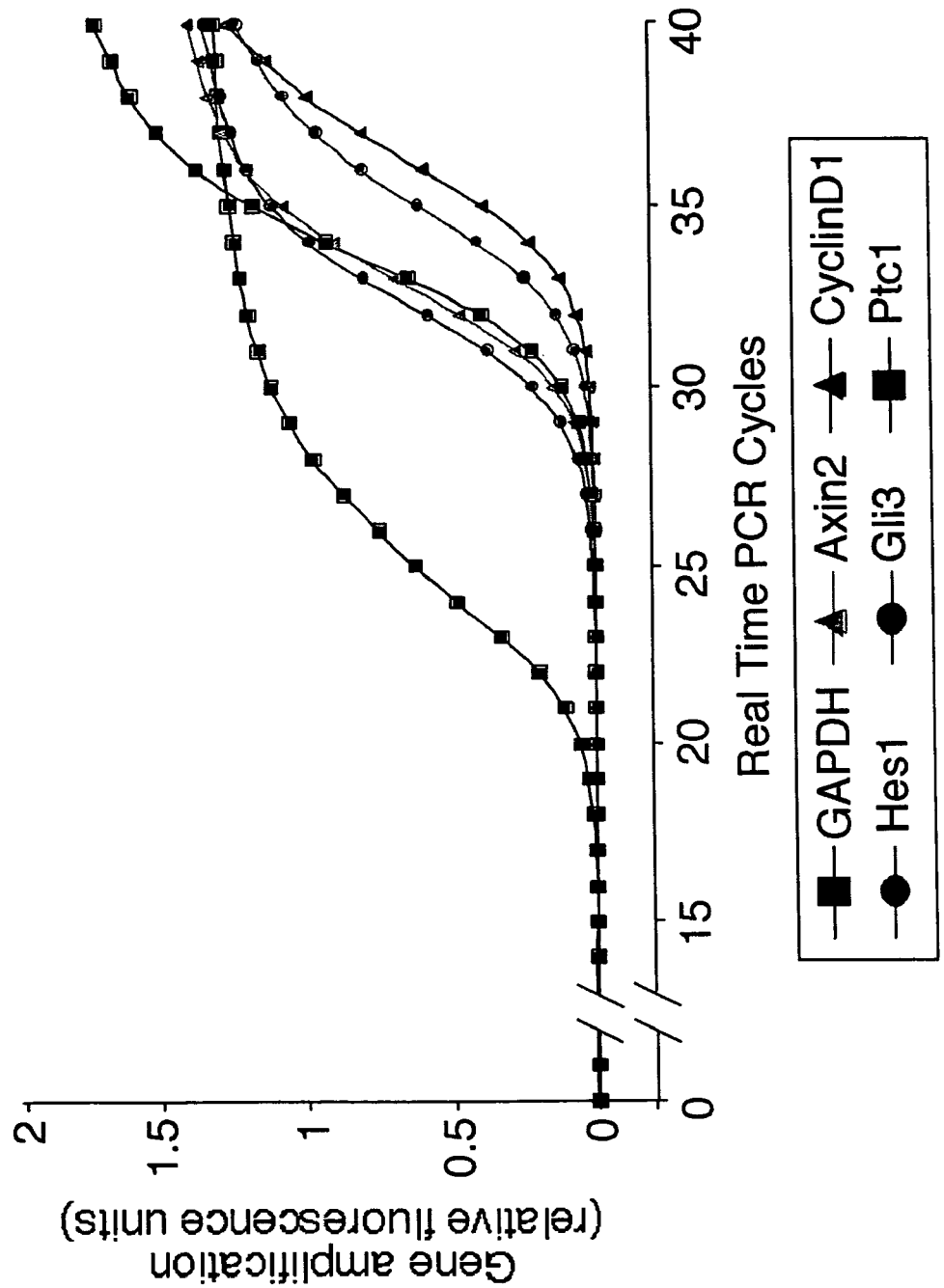

To determine whether Wnt signaling in HSCs was affected by GSK-3 inhibitor administration, the level of β-galactosidase expression was used to assess Wnt activation in treated HSCs isolated from TOP-gal mice using flow cytometry and fluorescein di-β-D-Galactopyranoside (FDG) intracellular staining. Negative and positive staining controls are shown (FIG. 3d). Upon in vivo GSK-3 inhibitor treatment, Wnt signaling in HSCs was increased by up to 28% (FIGS. 3e, f). In contrast, Wnt signaling was not significantly affected in more mature (Lin+Sca-1−) hematopoietic subsets (FIG. 3f), illustrating the specific effect of GSK-3 inhibitor administration on Wnt signaling within HSCs. To further characterize the effects of GSK-3 inhibitor on the Wnt pathway, Wnt-regulated target genes Axin2 and CyclinD1 were examined by quantitative real-time PCR in highly purified HSC isolates (FIG. 3g). Yan et al., *Proc Natl Acad Sci USA* 98:14973-8, 2001; Jho et al., *Mol Cell Biol* 22:1172-83, 2002; Issack and Ziff, *Cell Growth Differ* 9:837-45, 1998. Axin2 was down-regulated 1.5-fold, whereas CyclinD1 was upregulated by 2.5-fold after in vivo GSK-3 inhibitor treatment, compared to control treated purified HSCs (FIG. 3h), further supporting in vivo action of GSK-3 inhibitor treatment on targets of the Wnt pathway in HSCs.

Figure 3H:
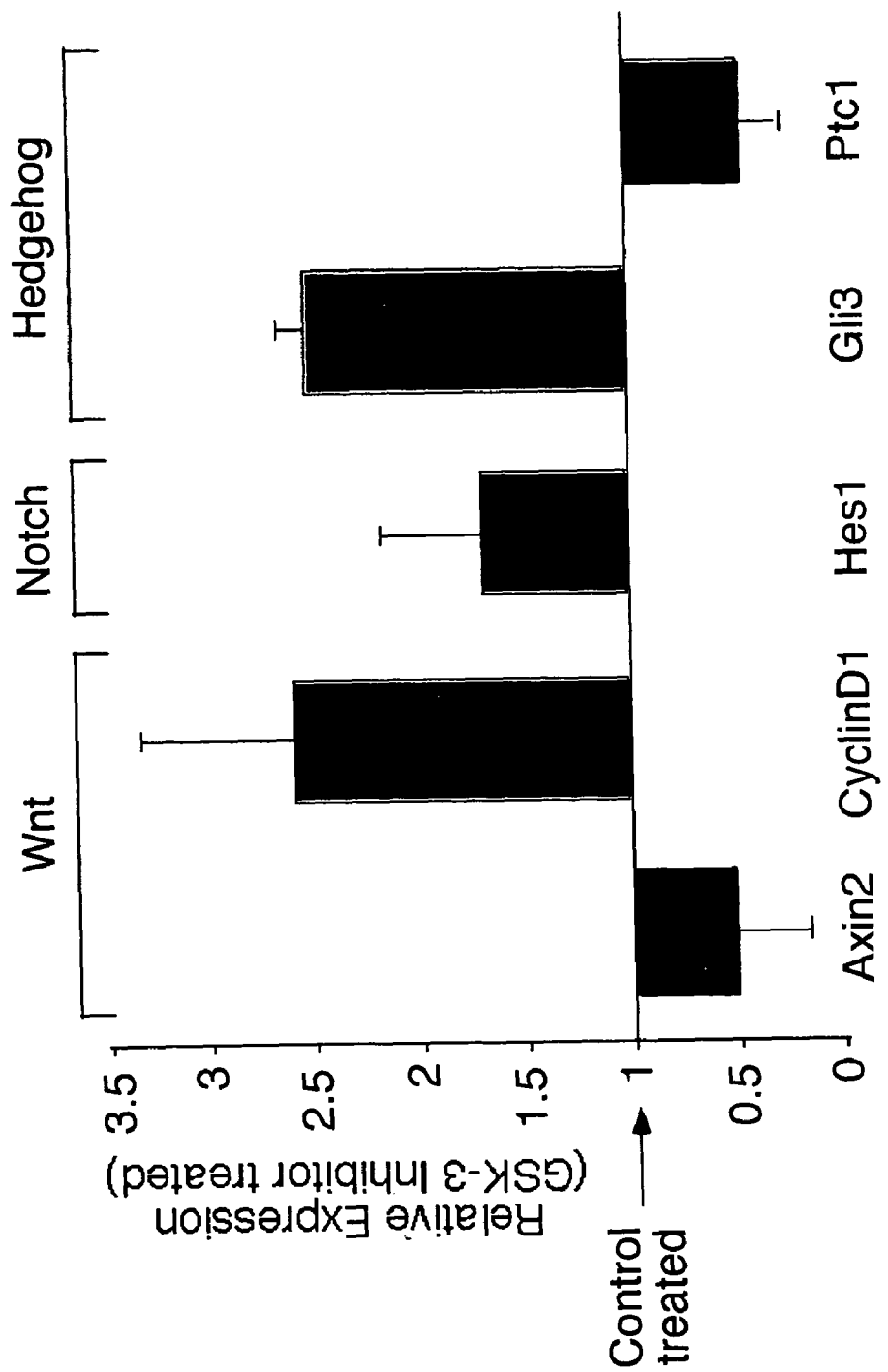

In addition to modulating the Wnt pathway, GSK-3 has been associated with Notch and Hedgehog signaling both also implicated in self-renewal of HSCs. Foltz et al., *Curr Biol* 12:1006-1011, 2002; Espinosa et al., *J Biol Chem* 278:32227-35, 2003; Bhardwaj et al., *Nat Immunol* 2:172-80, 2001; Dyer et al., *Development* 128:1717-30, 2001; Jia et al., *Nature* 416:548-552, 2002; Karanu et al., *J Exp Med* 192:1365-72, 2000; Karanu et al., *Blood* 97:1960-7, 2001; Varnum-Finney et al., *Nat Med* 6:1278-81, 2000. To more broadly investigate the potential effects of GSK-3 inhibition on these pathways, expression of Notch regulated gene target, Hes1, and gene targets of the Hedgehog pathway, Gli3 and Patched1 (Ptc1), were quantitatively examined in purified HSCs derived from GSK-3 inhibitor treated TOP-gal mice. Jarriault et al., *Nature* 377:355-8, 1995; Marigo et al., 180 1:1996; Marigo and Tabin, *Proc Natl Acad Sci USA* 93:9346-9351, 1996. Expression of Hes1 was increased, whereas Gli3 was increased 2.5-fold, and Ptc1 expression downregulated 1.5-fold after GSK-3 inhibitor treatment (FIG. 3h). This profile of gene regulation suggests that GSK-3 inhibition activates the Notch pathway, in contrast to apparent repression of the Hedgehog pathway in HSCs.

FIG. 3 shows that in vivo administration of GSK-3 inhibitor to TOP-gal mice enhances HSC activity and regulates targets of the Wnt, Notch and Hedgehog pathways. (a) Schematic illustration of experimental design utilizing TOP-gal transgenic mice to test effects of in vivo administration of GSK-3 inhibitor on HSC frequency, activation of Wnt signaling, and progenitor function measured by an in vitro hematopoietic colony-forming unit (CFU) assay. (b) Frequency of HSCs following in vivo administration of GSK-3 inhibitor or vehicle control. *$p<0.05$, ±represents SEM (n=3). (c) Hematopoeitic progenitor capacity of primitive (Lin−) hematopoietic cells following in vivo administration of GSK-3 inhibitor or vehicle control. Error bars represent SEM (n=3). (d) Establishing a flow cytometric assay for β-galactosidase using intracellular FDG staining. Histograms showing mean fluorescence intensity (MFI) of FDG for unstained bone marrow cells and stained ROSA26 bone marrow cells. (e) Representative histograms showing Wnt activation in HSCs following in vivo administration of GSK-3 inhibitor or vehicle control, measured by MFI of FDG. (f) Activation of Wnt signaling in HSCs and mature hematopoietic lineages (Lin+Sca-1−), following in vivo administration of GSK-3 inhibitor or vehicle control. *$p<0.05$, error bars represent SEM (n=4). (g) Real-time PCR amplification plots for Axin2, CyclinD1, Hes1, Gli3, Ptc1, and GAPDH from de novo isolated, wild-type mouse HSCs. (h) Relative expression of Axin2, CyclinD1, Hes1, Gli3, and Ptc1 in TOP-gal HSCs following in vivo administration of GSK-3 inhibitor, relative to vehicle control. Replicates were averaged after normalization to levels of the housekeeping gene GAPDH. Error bars represent SEM (n=3).

Figure 4A:
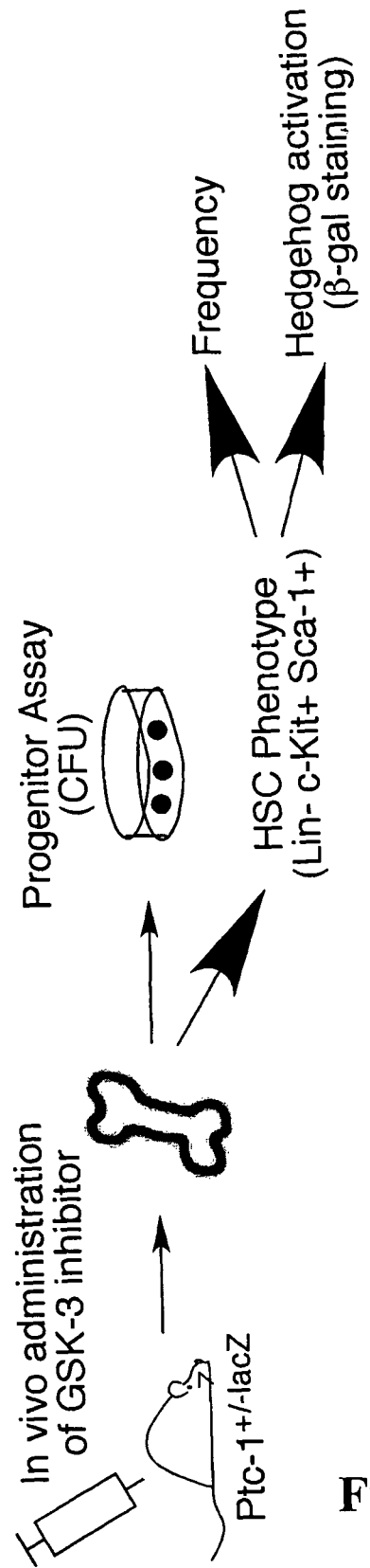
FIGS. 4a, 4b, 4c, and 4d show that in vivo administration of GSK-3 inhibitor to Ptc-1$^{+/-lacZ}$ mice enhances HSC activity and decreases Hedgehog signaling targets.
Figure 4B:
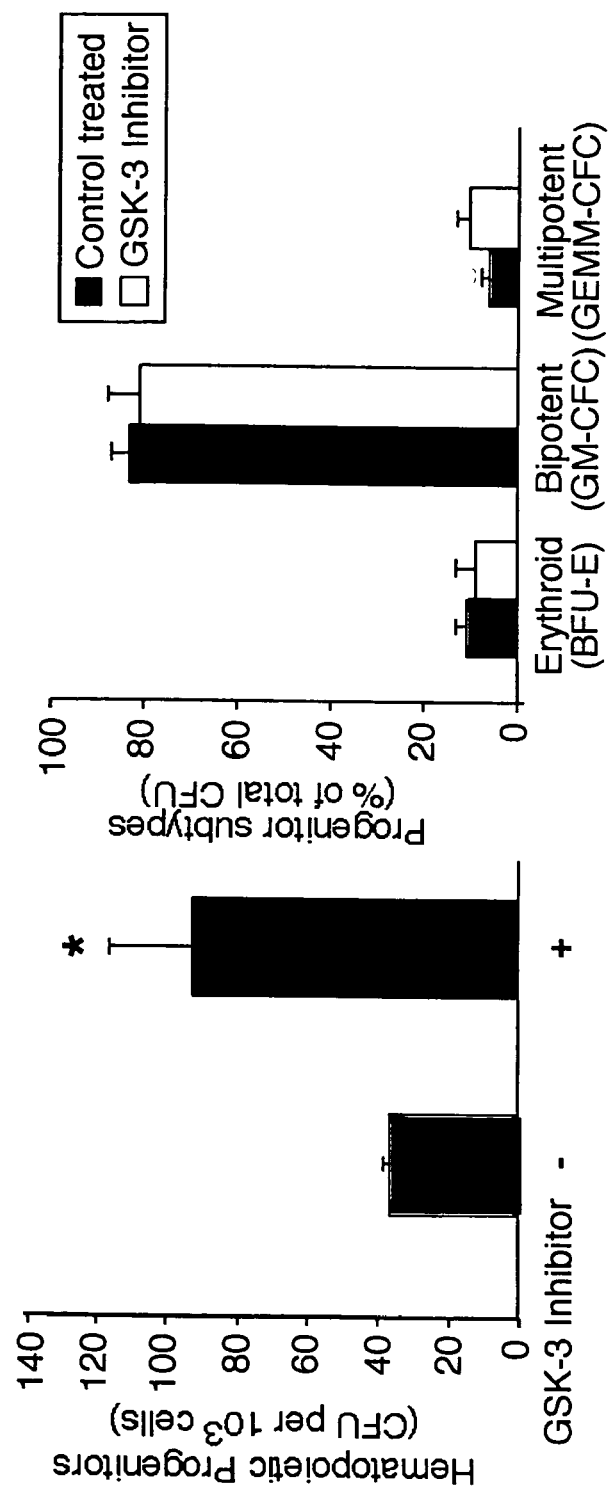
Figure 4C:
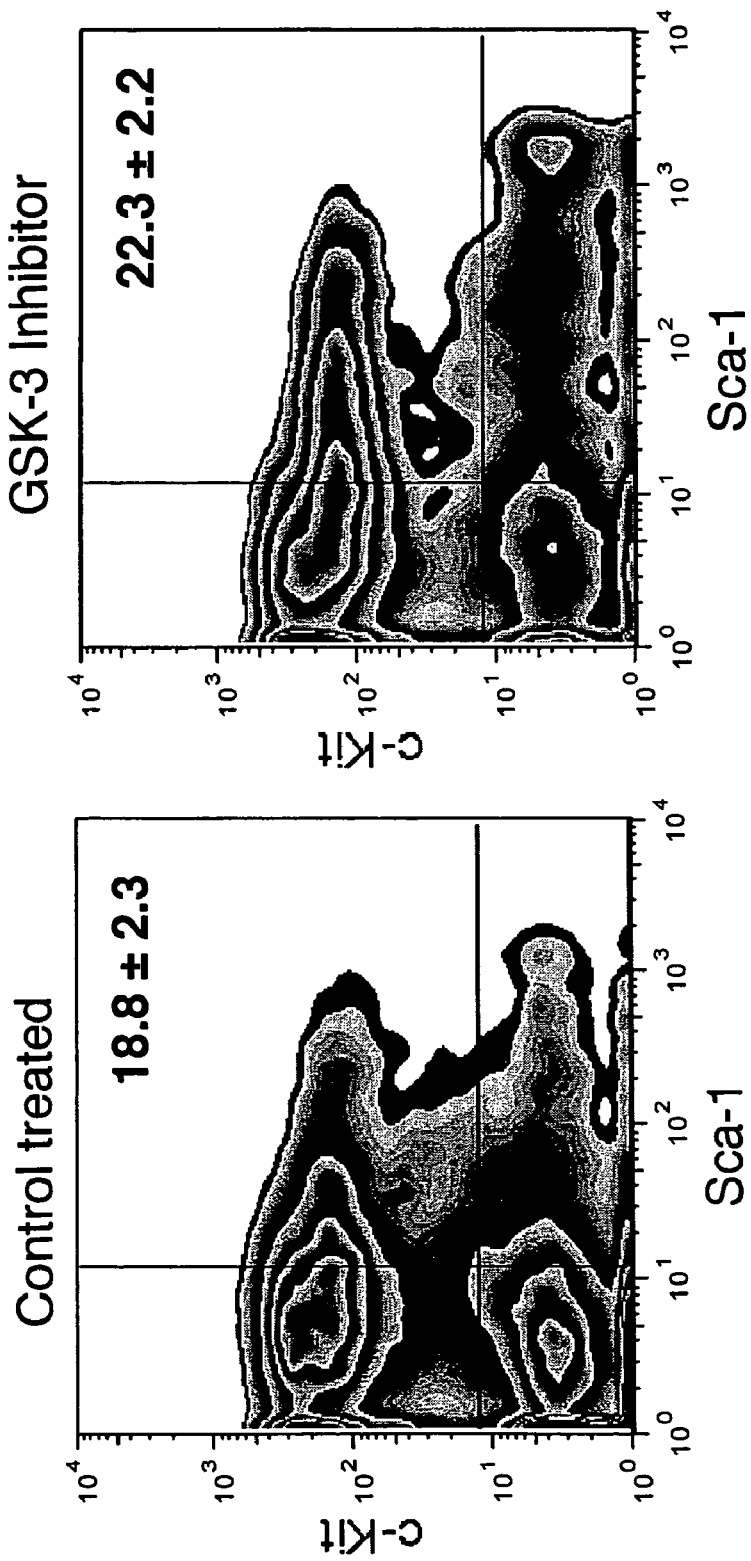
Figure 4D:
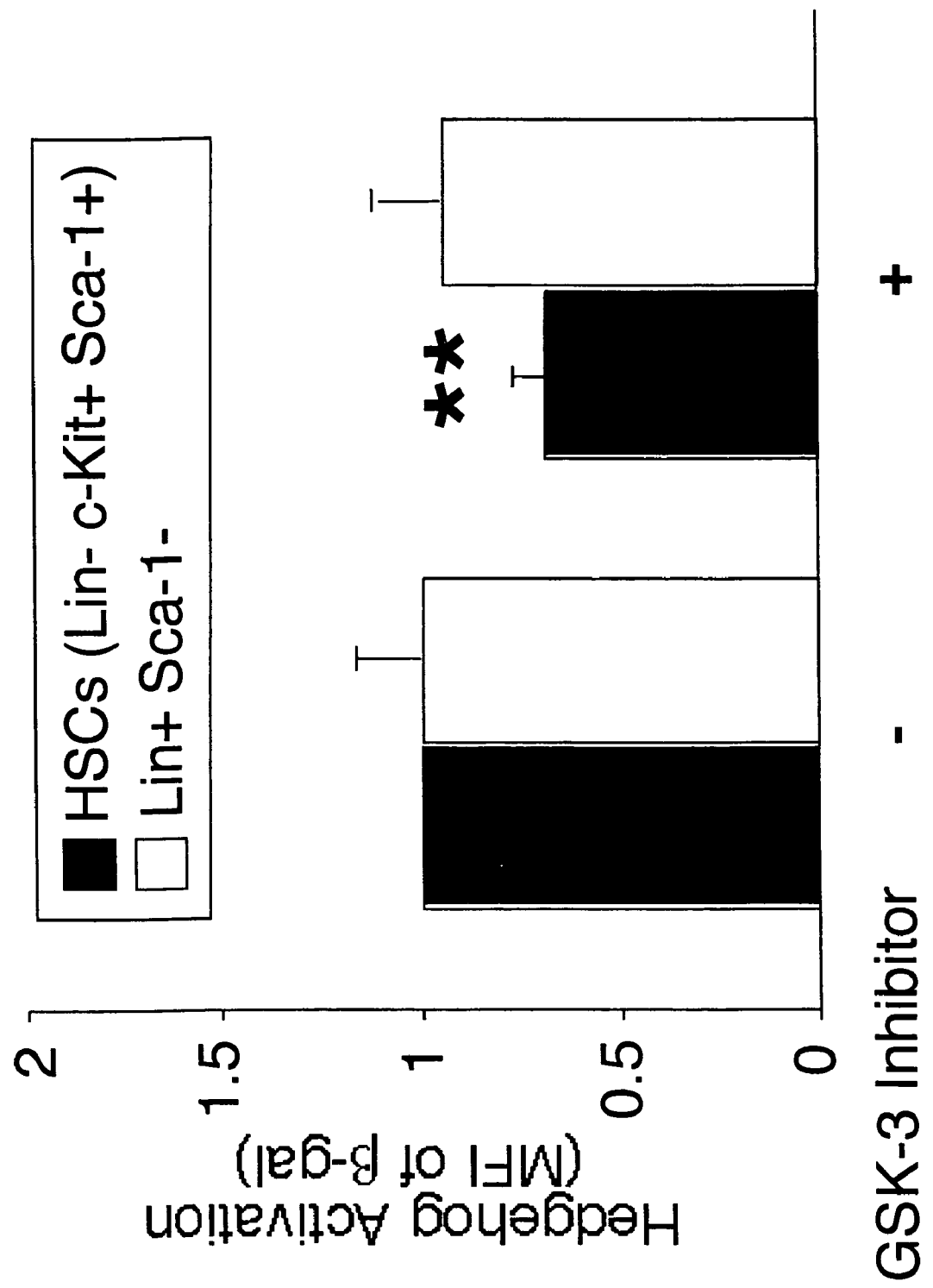

Due to contrasting effects on Notch and Wnt pathways versus the Hedgehog pathway, Hedgehog regulation in vivo using HSCs of transgenic Ptc1$^{+/-lacZ}$ mice having one copy of Patched1 (Ptc1) replaced with a lacZ coding sequence was further characterized (FIG. 4a). Goodrich et al., *Science* 277:1109-1113, 1997. Similar to TOP-gal mice, administration of GSK-3 inhibitor in vivo resulted in a significant increase in hematopoietic progenitors compared to control treated Ptc1$^{+/-lacZ}$ mice (FIG. 4b). The composition of clonogenic progenitors detected (represented by erythroid, bipotent granulocyte-macrophage, and multipotent mixed lineage colony types) was not affected by GSK-3 inhibitor treatment, compared to control treatment (FIG. 4b), indicating that the progenitor potential was not affected by the GSK-3 inhibitor. Administration of GSK-3 inhibitor in vivo resulted in a 16% increase in the frequency of HSCs compared to control treated mice (FIG. 4c). However, the Hedgehog pathway itself was significantly decreased in expanded HSCs derived from mice treated with GSK-3 inhibitor, but was not affected in more abundant and mature (Lin+Sca-1−) hematopoietic cells (FIG. 4d). The specificity of GSK-3 inhibitor regulation of Ptc1$^{+/-lacZ}$ HSCs is similar to that observed in TOP-gal mice used as reporters of Wnt signaling (FIG. 3f). Taken together, these results suggest that in vivo administration of GSK-3 inhibitor modulates downstream Wnt, Hedgehog, and Notch signals in HSCs, and increases frequency and function of HSCs in their native environment.

FIG. 4 shows that in vivo administration of GSK-3 inhibitor to Ptc-1$^{+/-lacZ}$ mice enhances HSC activity and decreases Hedgehog signaling targets. (a) Schematic illustration of experimental design to test effects of in vivo administration of GSK-3 inhibitor to Ptc-1$^{+/-lacZ}$ mice on progenitor function (CFU), frequency of HSCs, and activation of Hedgehog signaling. (b) Hematopoietic progenitor capacity of primitive (Lin−) hematopoietic cells following in vivo administration of GSK-3 inhibitor or vehicle control. *$p<0.05$, error bars represent SEM (n=3). Subtypes of hematopoietic colonies (BFU-E, GM-CFC, GEMM-CFC) are presented as a percentage of total CFU. Error bars represent SEM (n=3). (c) Frequency of HSCs following in vivo administration of GSK-3 inhibitor or vehicle control. ±represents SEM (n=3). (d) Hedgehog activation in HSCs and mature hematopoietic lineages (Lin+Sca-1−), following in vivo administration of GSK-3 inhibitor or vehicle control. **$p<0.01$, error bars represent SEM (n=3).

EXAMPLE 4

Figure 5A:
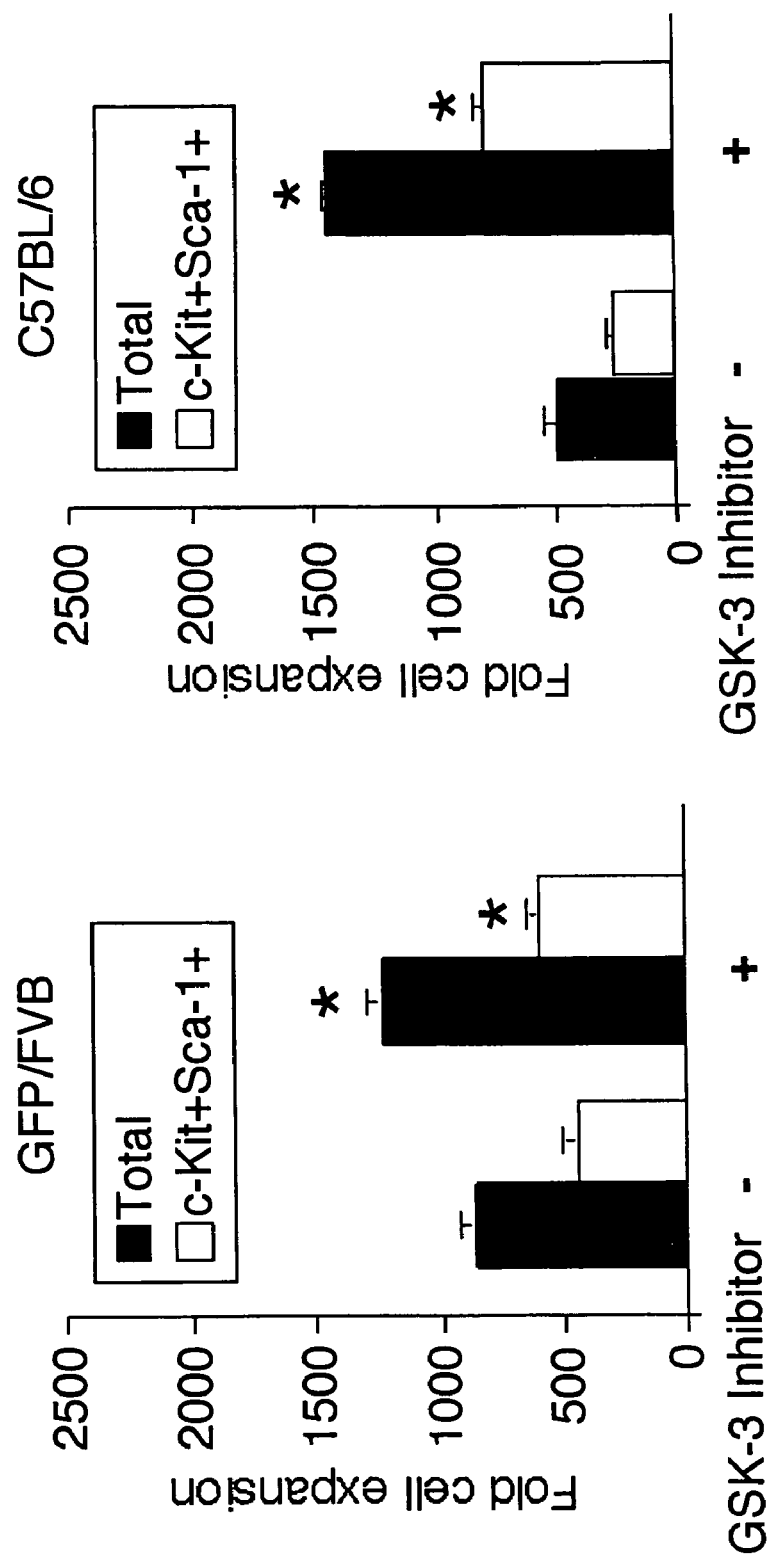
FIGS. 5a, 5b, and 5c show that in vitro effects of GSK-3 inhibitor on purified HSCs.
Figure 5B:
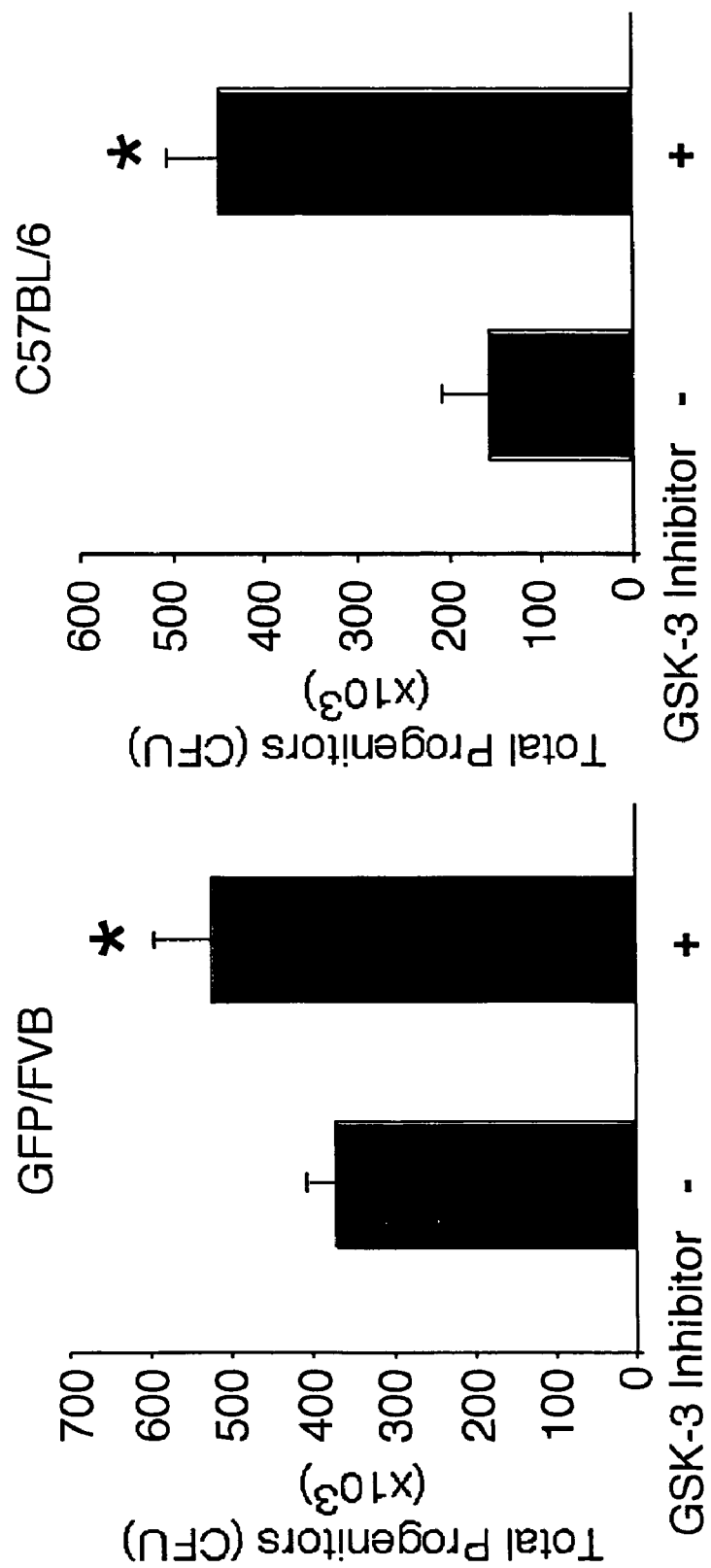

HSC Isolation and In Vitro Culture Demonstrates GSK-3 Inhibitor Acts Directly on HSCs and Modulates Targets of Wnt, Hedgehog, and Notch Pathways Recent studies have characterized the HSC microenvironment, indicating that genetic perturbation of the HSC niche via transgenic systems can have profound effects on HSC regulation. Calvi et al., *Nature* 425:841-6, 2003. Since GSK-3 inhibitor administration affects HSCs in vivo, it is possible that GSK-3 inhibitors act on the HSC microenvironment to elicit their effect on HSC function indirectly via cells in the HSC niche. To address this possibility, HSCs were isolated from GFP/FVB and C57BU6 mice and treated with GSK-3 inhibitor in vitro, thereby removing any potential indirect effects of the bone marrow microenvironment. GSK-3 inhibitor significantly increased the total cell proliferation of purified GFP/FVB HSCs by 1.5-fold, and C57BL/6 HSCs by 3-fold (FIG. 5a), as compared to control treated HSCs. The frequency of expanded cells maintaining HSC phenotype (c-Kit+Sca-1+) was similarly affected (FIG. 5a). In addition, direct treatment of GFP/FVB and C57BL/6 HSCs with GSK-3 inhibitor demonstrated significant increases in total CFU capacity (FIG. 5b), similar to effects of in vivo GSK-3 administration (FIGS. 1-4).

Figure 5C:
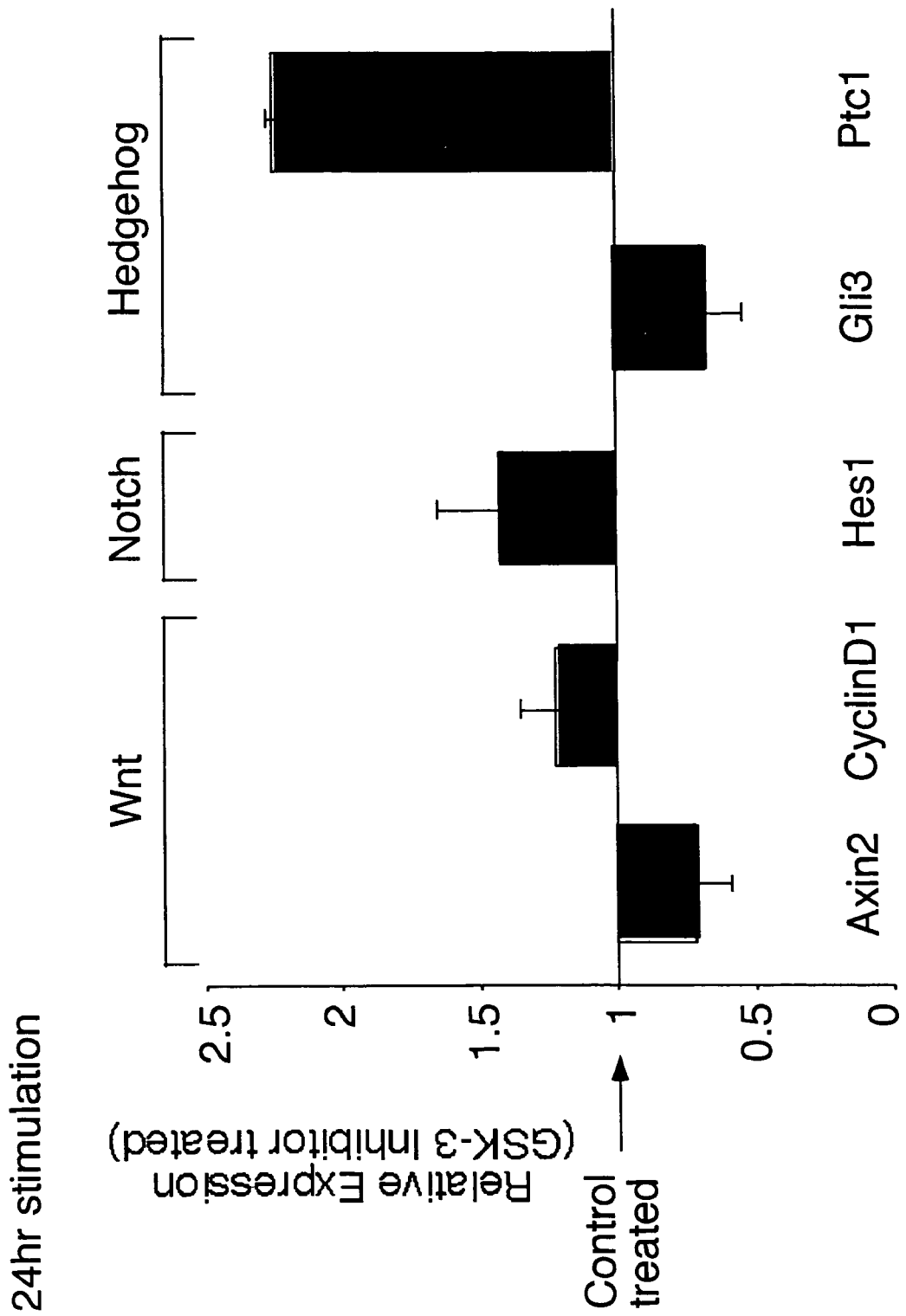

To examine whether Wnt, Notch, and Hedgehog pathways were modulated by GSK-3 inhibitor treatment in the absence of the bone marrow microenvironment, purified HSCs were stimulated with GSK-3 inhibitor for 24 hours, and Wnt, Hedgehog, and Notch gene targets were quantitatively examined. As shown in FIG. 5c, Wnt, Notch, and Hedgehog target genes were modulated by GSK-3 inhibitor addition. These results demonstrate that, similar to in vivo administration of GSK-3 inhibitors, direct in vitro treatment of HSCs with GSK-3 inhibitor augments proliferation and CFU capacity, while modulating Wnt, Hedgehog, and Notch pathways. These data confirm that GSK-3 inhibitors are capable of directly modulating HSC function in the absence of non-HSC elements comprising the bone marrow microenvironment.

FIG. 5 shows that in vitro effects of GSK-3 inhibitor on purified HSCs. (a) Fold cell expansion of HSCs isolated from GFP/FVB and C57BL/6 mice after 9 days in vitro culture with GSK-3 inhibitor or vehicle control. The post-culture frequency of c-Kit+Sca-1+ cells was multiplied by total cell expansion (black bars), and used to calculate fold cell expansion of the c-Kit+Sca-1+ population (white bars). *p<0.05 vs. control culture, error bars represent SEM (n=3) (b) Total number of hematopoietic progenitors in the expanded population after in vitro culture of GFP/FVB and C57BL/6 HSCs with GSK-3 inhibitor. *p<0.05, error bars represent SEM (n=4) (c) Relative expression of Axin2, CyclinD1, Hes1, Gli3, and Ptc1 in GFP/FVB HSCs following 24-hour in vitro stimulation with GSK-3 inhibitor. After GSK-3 inhibitor treatment, expression of Axin2 was downregulated 1.3-fold and CyclinD1 was upregulated 1.2-fold; Hes1 was increased 1.4-fold; Gli3 was downregulated 1.3-fold and Ptc1 upregulated 2.3-fold. Replicates were averaged after normalization to levels of the housekeeping gene GAPDH. Error bars represent SEM (n=2).

EXAMPLE 5

In Vivo Administration of GSK-3 Inhibitor Increases Repopulating Function of Transplanted Wild-Type Mouse HSCs, and Augments Human Neonatal and Adult HSC Capacity In Vivo The present invention demonstrates that in vivo administration of GSK-3 inhibitor increases repopulating function of transplanted wild-type mouse HSCs, and augments human neonatal and adult HSC capacity in vivo. Investigation of the mechanism accounting for this functional response in HSCs revealed that GSK-3 inhibitor modulates gene targets of the Wnt, Hedgehog, and Notch pathways. Furthermore, in vitro culture of purified HSCs with GSK-3 inhibitor increased proliferation and functional capacity of HSCs, and modulated Wnt, Hedgehog, and Notch pathways, providing evidence that GSK-3 inhibitors directly affect HSCs.

Figure 6:
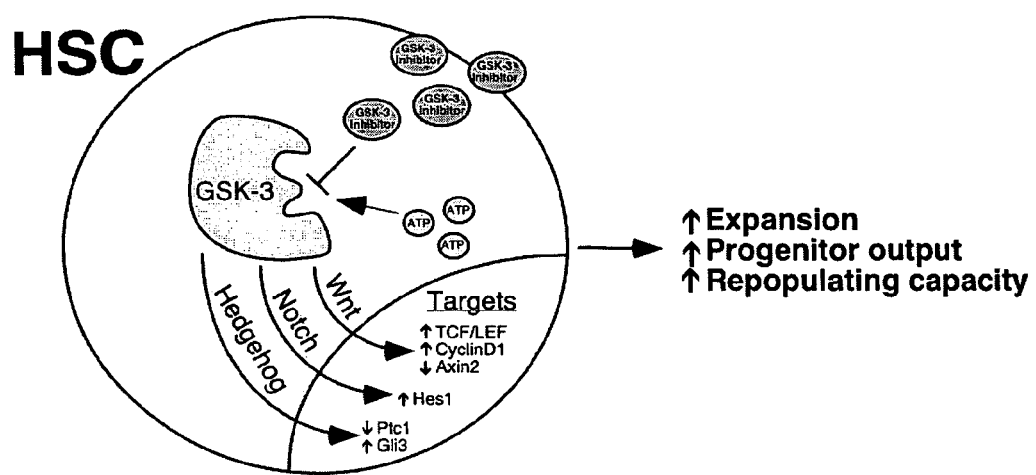
FIG. 6 shows a proposed model for the functional and molecular effects of GSK-3 inhibition on mammalian HSCs.

A working model of the in vivo functional and molecular effects of GSK-3 inhibitors on HSCs is proposed (FIG. 6). Functionally, GSK-3 inhibitor treatment results in an increase in in vivo HSC expansion, hematopoietic progenitor output as measured by CFU assay, and in vivo repopulating capacity of HSCs. At a molecular level, GSK-3 inhibitors modulate downstream targets of the Wnt, Hedgehog, and Notch pathways. The Hedgehog target gene, Ptc1, is downregulated specifically in HSCs following GSK-3 inhibitor treatment, demonstrated by the transgenic Ptc-1$^{+/-lacZ}$ mouse reporter, and confirmed by real-time PCR on isolated HSCs. This indicates that Hedgehog signaling is being repressed in HSCs following GSK-3 inhibitor treatment. In addition, GSK-3 inhibitor treatment increases expression of Hes1 in HSCs, indicative of increased Notch signaling which has previously been shown to immortalize HSCs without inducing transformation. Varnum-Finney et al., Nat Med 6:1278-81, 2000. The effects of GSK-3 inhibitor on Wnt signaling appear to be more complex. Activation of the TCF/LEF reporter in TOP-gal mice was specifically increased in HSCs following GSK-3 inhibitor treatment, indicative of increased Wnt signaling activation. However, there were opposing effects on two established downstream Wnt target genes, CyclinD1 and Axin2. The combination of transcriptional upregulation of CyclinD1 and downregulation of Axin2 suggests that GSK-3 inhibitor regulates HSCs distinctly from Wnt ligands, which would be predicted to upregulate both of these target genes. These findings support that multiple signaling pathways are involved in the regulation of HSC fate decisions and suggest a more universal role for GSK-3 in stem cell regulation, a paradigm supported recently by observations that GSK-3 inhibitors sustain mouse and human embryonic stem cells in vitro. Reya, Recent Prog Horm Res 58:283-295, 2003; Sato et al., Nat Med 10:55-63, 2004.

Many intrinsic regulators of HSC function, including STAT5A and p21, have been identified by gene targeting or overexpression strategies. Schuringa et al., J Exp Med 200: 623-35, 2004; Cheng et al., Science 287:1804-8, 2000. In addition, extrinsic regulators of HSC function have been investigated through ligand treatment or ectopic expression of key upstream regulators of Wnt, Hedgehog, and Notch signaling pathways in HSCs. Murdoch et al., PNAS 100: 3422-3427, 2003; Reya et al., Nature 423:409-14, 2003; Bhardwaj et al., Nat Immunol 2:172-80, 2001; Karanu et al., J Exp Med 192:1365-72, 2000; Karanu et al., Blood 97:1960-7, 2001; Varnum-Finney et al., Nat Med 6:1278-81, 2000. While these studies contribute to our fundamental understanding of HSC biology, these targets cannot be specifically controlled extrinsically for clinical benefit without invasive and complex procedures involving HSC isolation, ex vivo culture, and genetic manipulation. In the context of clinical use, in vivo modulation of HSC function by administration of GSK-3 inhibitors is unique, and not only is capable of acting specifically on HSCs, but is able to modulate downstream components of several of the signaling pathways associated with HSC regulation.

The applicability of GSK-3 inhibitors in a clinical setting to enhance HSC function in vivo offers a further use for these well-developed drugs currently being optimized as treatments for a variety of diseases, including diabetes and Alzheimer's. Cohen and Goedert, Nat Rev Drug Dis 3:479-87, 2004. Direct modulation of HSCs in patients provides a novel approach to traditional HSC-based therapies that allows unique application in cases where HSC numbers are limiting, or in transplant recipients demonstrating poor engraftment. In addition, administration of GSK-3 inhibitors to adult patients transplanted with limited numbers of CB-derived HSCs can provide the necessary augmentation of CB-HSC reconstitution in adults, thereby expanding the use of CB donors to adult recipients without the need for ex vivo expansion or pooling of MHC-disparate CB samples for transplantation. Barker et al., *Blood* Epub ahead of print:2004; Gluckman, *Exp Hematol* 28:1197-205, 2000.

EXAMPLE 6

Use Of Wnt/β-Catenin Signal-, Notch Signal- or Hedgehog Signal Promoting Agents to Inhibit Proliferation and/or Induce Differentiation of Leukemic Stem Cells and to Treat Leukemic Disease Compositions of Wnt/β-catenin signal-, Notch signal- or Hedgehog signal promoting agents, for example, GSK-3 inhibitors, can be used to inhibit stem cell proliferation, for example, leukemic stem cells, and to treat leukemic disease. Compositions of Wnt/β-catenin signal-, Notch signal- or Hedgehog signal promoting agents in combination with compositions including peptides and polypeptides which are inhibitors of stem cell proliferation, for example, polypeptides of α-hemoglobin in combination with opiate compounds. The compositions can be used to treat autoimmune disease, cancer, psoriasis, AIDS, anemia or pain. See U.S. Pat. No. 6,784,155, incorporated herein by reference in its entirety.

In human patients with early acute lymphoblastic leukemia (ALL) or primitive acute myeloid leukemia, the disease is known to originate and be sustained by a transformed hematopoietic stem cell (HSC). This transformed HSC or leukemic HSC possessing cell cycle regulation and differentiation potential is distinct from its normal counterpart in the patients or from HSCs transplanted into the patient from an allogenic source. One or more Wnt/β-catenin signal-, Notch signal- or Hedgehog signal-promoting agents, for example, GSK-3 inhibitors, will inhibit the proliferation of transformed HSC or leukemic HSC by inducing senescence or apoptotic programs, and/or induce differentiation of leukemic stem cells into benign mature blood cells that will terminally differentiate and be lost. This provides a purging strategy to eradicate leukemic stem cells, and/or induce normal HSC to reconstitute a non-cancerous blood system via targeted GSK-3 inhibition.

EXAMPLE 7

Methodology

Mice. GFP/FVB, C57BL/6, Tg(Fos-lacZ)34Efu (TOP-gal), Ptc-1$^{+/-lacZ}$ (Stanford University School of Medicine) and NOD/LtSz-scid/scid (NOD/SCID) mice were used at 8-12 weeks of age. Tsirigotis et al., *Biotechniques* 31:120-126, 128, 130, 2001; DasGupta and Fuchs, *Development* 126:4557-4568, 1999; Goodrich et al., *Science* 277:1109-1113, 1997. Mice were bred and maintained in the animal barrier facility at Robarts Research Institute (London, Ontario, Canada), with the exception of Ptc-1$^{+/-lacZ}$, bred and maintained in conventional housing in the University of Western Ontario animal care facility (London, Ontario, Canada).

GSK-3 Inhibitors. ATP-competitive, selective GSK-3 inhibitors CHIR-911 and CHIR-837 (also referred to as CT-99021 and CT-98023 respectively). Chiron Corporation (Emeryville, Calif.). These inhibitors were purified to >95% by high-performance liquid chromatography. CHIR-911 was formulated in 10% captisol solution for administration in vivo by intraperitoneal injection, with a half-maximal effective concentration [EC$_{50}$] of 766 nM and >10,000 fold selectivity for GSK-3. Ring et al., *Diabetes* 52:588-595, 2003. CHR-837 was formulated in DMSO for in vitro use, with an EC$_{50}$ of 375 nM and >5,000 fold selectivity for GSK-3 Cline et al., *Diabetes* 51:2903-2910, 2002.

Murine HSC isolation. A lineage-depleted (Lin−) population was purified from bone marrow cells using the StemSep™ murine hematopoietic progenitor enrichment kit (StemCell Technologies, Vancouver, BC, Canada). Cells expressing high levels of c-Kit and Sca-1 were further purified by cell sorting using a FACSVantage SE (Becton Dickinson (BD), Franklin Lakes, N.J.).

Human hematopoietic cell purification. Human umbilical cord blood (CB) mononuclear cells (MNCs) were isolated and enriched for a lineage-depleted (Lin−) population as described. Bhatia et al., *Proc Natl Acad Sci USA* 94:5320-5325, 1997. For mobilized peripheral blood (M-PB), the mobilization regimen consisted of 20 µg/kg/d SCF (Amgen, Mississauga, ON, Canada) plus 10 µg/kg/d Neupogen® (G-CSF) administered subcutaneously, from day 1 to completion of apheresis (day 11). Whole blood was harvested at 11 days, and MNCs collected by centrifugation on Ficoll-Paque (Pharmacia, Piscataway, N.J.). The patient had achieved a total cell dose exceeding $2 \times 10^8$ CD34+ cells per L.

In vivo HSC repopulation assay. Purified cell populations were transplanted by tail vein injection into sublethally irradiated (350 rads, 137Cesium) NOD/SCID mice according to standard protocols 26. Mice received intraperitoneal injections of 30 mg/kg body weight CHIR-911 (Chiron Corporation) or vehicle control (10% captisol) twice per week for the duration of the transplant period. Mice that received GFP/FVB BM-derived cells were sacrificed 5 weeks after transplantation, and those transplanted with human cells were sacrificed after 5-6 weeks. Engraftment was assessed by the presence of GFP+ donor mouse cells, or CD45+ donor human cells, in combination with analysis of mature, multilineage hematopoietic cell surface makers, on a FACSCalibur (BD).

Hematopoeitic colony-forming unit (CFU) assays. Mouse clonogenic hematopoietic progenitor assays were performed by plating equal numbers of GSK-3 inhibitor treated, or control treated, cells into MethoCult™ GF M3434 (StemCell Technologies), and scoring colonies after 10-12 days incubation at 37° C. and 5% $CO_2$. Human CFU assays were performed by plating equal numbers of GSK-3 inhibitor treated or control treated cells into MethoCult™ H4434 (StemCell Technologies) containing 50 ng/mL human SCF (Amgen), 10 ng/mL GM-CSF, 10 ng/mL interleukin-3, and 3 U/mL erythropoietin (all R&D Systems, Minneapolis, Minn.). Differential colony counts were assessed following incubation for 10-14 days at 37° C. and 5% $CO_2$ as described previously. Bhatia et al., *Nat Med* 4:1038-45, 1998.

Fluorescein di-β-D-Galactopyranoside (FDG) staining. Primitive (Lin−) hematopoietic cells isolated from TOP-gal or Ptc-1$^{+/-lacZ}$ mice in PBS/5% FBS were incubated 2 min at 37° C. with an equal volume of 2 mM FDG reagent (Marker Gene Technologies Inc., Eugene, Oreg.) in $dH_2O$. FDG loading was terminated by addition of cold PBS/FBS. Cells were then stained with fluorescent-conjugated antibodies against c-Kit and Sca-1, the viability dye 7-AAD (BD), and analyzed on a FACSCalibur (BD).

Real-time PCR analysis. Total RNA was extracted from a minimum of 30,000 de novo isolated HSCs, or cells re-isolated after culture based on expression of high levels of c-Kit and Sca-1, using the RNeasy kit (Qiagen, Mississauga, ON, Canada). First strand cDNA synthesis was performed (First-Strand cDNA Synthesis Kit, Amersham Biosciences, Piscataway, N.J.), and resulting cDNA analyzed for differential gene expression by real-time PCR using SYBRGREEN double-stranded DNA binding dye and the Mx4000TM Multiplex Quantitative PCR System (Stratagene, La Jolla, Calif.). Comparative quantitation of transcripts was assessed relative to the housekeeping gene glyceraldehyde-3-phosphate dehydrogenase (GAPDH). All primer sequences are listed in Table 1. Amplified products were agarose gel purified and sequenced to verify specificity of gene amplification.

TABLE 1

| | Forward Primer (5' to 3') | Reverse Primer (5' to 3') | SEQ ID NO: |
|---|---|---|---|
| GAPDH | TTCACCACCATGGAGAAGGC | GGCATGGACTGTGGTCATGA | 1, 2 |
| Axin2 | AACCTATGCCCGTTTCCTCT | CTGGTCACCCAACAAGGAGT | 3, 4 |
| CyclinD1 | AGTGCGTGCAGAAGGAGATT | CACAACTTCTCGGCAGTCAA | 5, 6 |
| Hes1 | CTACCCCAGCCAGTGTCAAC | ATGCCGGGAGCTATCTTTCT | 7, 8 |
| Gli3 | TGCCCATCAGCTACTCAGTG | TTGTTGCAGAGTGAGGTTGC | 9, 10 |
| Ptc1 | CTCAGGCAATACGAAGCACA | GACAAGGAGCCAGAGTCCAG | 11, 12 |

Serum-free HSC culture. Purified cells were cultured in BIT 9500 (StemCell Technologies), diluted in Iscove's modified Dulbecco's medium (IMDM), and supplemented with β-mercaptoethanol (55 mM), L-glutamine (2 mM, Gibco BRL, Gaithersburg, Md.), 100 ng/mL human IL-6 (R&D Systems), 50 ng/mL mouse SCF (StemCell Technologies), 100 ng/mL mouse IL-11 (StemCell Technologies), and 100 ng/mL human Flt-3 ligand (R&D Systems). Cells were cultured for 9 days with 1 μM CHIR-837 (Chiron Corporation), or vehicle (DMSO) at 37° C. and 5% $CO_2$, and replenished with fresh media every 2 days.

Statistical analysis. Data was analyzed by paired, two-tailed Student t tests, and results considered significant when $P \leq 0.05$. Error bars represent SEM.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed:

1. A method for increasing an endogenous hematopoietic adult stem cell or progenitor cell population in a mammalian subject comprising:
   selecting a mammalian subject in need of an increase in its endogenous hematopoietic adult stem cell or progenitor cell population and
   administering, to the selected mammalian subject, a glycogen synthase kinase-3 (GSK-3) inhibitor in the form of a small molecule, whereby said administering the GSK-3 inhibitor to the selected mammalian subject increases the endogenous hematopoietic adult stem cell or progenitor cell population in the selected mammalian subject compared to the endogenous adult stem cell or progenitor cell population in the selected mammalian subject before treatment.

2. The method of claim 1, wherein the adult hematopoietic stem cell population further comprises adult hematopoietic progenitor cells of erythroid cells, granulocyte cells, macrophage cells, granulocyte-macrophage cells, B cells, T cells, and multipotent mixed lineage colony types.

3. The method of claim 1, wherein said increasing the adult stem cell or progenitor cell population in the selected mammalian subject is a result of increased engraftment, cell proliferation, cell homing, decreased apoptosis, self renewal, or increased cell survival.

4. The method of claim 1, wherein said administering is carried out at a dose of 0.0001 to 100 mg/kg of subject body weight.

5. The method of claim 1, wherein said administering is carried out by intravesicular, intrathecal, parenteral, topical, intravenous, oral, inhalant, subcutaneous, intraarterial, intracranial, intraperitoneal, intranasal, or intramuscular administration.

6. The method of claim 1 further comprising:
   administering stem cells or progenitor cells to the selected mammalian subject.

7. The method of claim 6, wherein stem cells are administered.

8. The method of claim 6, wherein progenitor cells are administered.

9. The method of claim 1, wherein the adult progenitor cell population is increased.

10. The method of claim 1, wherein the adult stem cell population is increased.

11. The method of claim 1, wherein said method activates the Wnt/β-catenin pathway in hematopoietic progenitor/stem cells of the subject.

12. The method of claim 1, wherein said method increases proliferation of the adult hematopoietic endogenous stem or progenitor cell population in the selected mammalian subject.

13. The method of claim 1, wherein the mammalian subject has an immune related disease.

14. The method of claim 13, wherein the immune related disease is selected from the group consisting of graft vs. host disease, immunodeficiency disease, hematopoietic malignancy, hematopoietic failure, and hematopoietic stem cell transplantation.

15. The method of claim 14, wherein the hematopoietic malignancy is selected from the group consisting of chronic myeloid leukemia, acute myeloid leukemia, non-Hodgkins's lymphoma, multiple myeloma, chronic lymphocytic leukemia, Hodgkin's disease, and myelodysplastic syndrome.

16. The method of claim 13, wherein the immunodeficiency disease is selected from the group consisting of primary immunodeficiency, hemoglobinopathy, and single gene disorders.

17. The method of claim 6, wherein the source of the administered stem cells or progenitor cells is selected from the group consisting of umbilical cord blood cells, bone marrow cells, and peripheral blood cells.

* * * * *